United States Patent
Koepke et al.

(10) Patent No.: US 11,555,209 B2
(45) Date of Patent: Jan. 17, 2023

(54) MICROORGANISMS AND METHODS FOR THE BIOLOGICAL PRODUCTION OF ETHYLENE GLYCOL

(71) Applicant: LanzaTech, Inc., Skokie, IL (US)

(72) Inventors: Michael Koepke, Skokie, IL (US); Rasmus Jensen, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

(21) Appl. No.: 16/226,603

(22) Filed: Dec. 19, 2018

(65) Prior Publication Data
US 2019/0185888 A1    Jun. 20, 2019

Related U.S. Application Data

(60) Provisional application No. 62/683,454, filed on Jun. 11, 2018, provisional application No. 62/607,446, filed on Dec. 19, 2017.

(51) Int. Cl.
| | | |
|---|---|---|
| *C12P 7/18* | (2006.01) | |
| *C12N 1/20* | (2006.01) | |
| *C12N 9/10* | (2006.01) | |
| *C12N 9/88* | (2006.01) | |
| *C12N 9/02* | (2006.01) | |
| *C12N 15/52* | (2006.01) | |

(52) U.S. Cl.
CPC .......... *C12P 7/18* (2013.01); *C12N 1/20* (2013.01); *C12N 9/0008* (2013.01); *C12N 9/1025* (2013.01); *C12N 9/1096* (2013.01); *C12N 9/88* (2013.01); *C12N 15/52* (2013.01); *C12Y 102/01003* (2013.01); *C12Y 102/01021* (2013.01); *C12Y 203/03001* (2013.01); *C12Y 206/01044* (2013.01); *C12Y 401/03001* (2013.01)

(58) Field of Classification Search
None
See application file for complete search history.

(56) References Cited

U.S. PATENT DOCUMENTS

| | | |
|---|---|---|
| 2,218,234 A | 10/1940 | Fisher |
| 5,552,023 A | 9/1996 | Zhou |
| (Continued) | | |

FOREIGN PATENT DOCUMENTS

| | | |
|---|---|---|
| WO | 2014004625 | 1/2014 |
| WO | 2017156166 | 9/2017 |

OTHER PUBLICATIONS

Alkim et al., "Optimization of ethylene glycol production from (D)-xylose via a synthetic pathway implemented in *Escherichia coli*," Microbial Cell Factories 14:127 (2015).
(Continued)

*Primary Examiner* — Richard C Ekstrom
(74) *Attorney, Agent, or Firm* — Stephen M. Chong

(57) ABSTRACT

The invention provides genetically engineered microorganisms and methods for the biological production of ethylene glycol and precursors of ethylene glycol. In particular, the microorganism of the invention produces ethylene glycol or a precursor of ethylene glycol through one or more of 5,10-methylenetetrahydrofolate, oxaloacetate, citrate, malate, and glycine. The invention further provides compositions comprising ethylene glycol or polymers of ethylene glycol such as polyethylene terephthalate.

18 Claims, 15 Drawing Sheets

Specification includes a Sequence Listing.

(56) References Cited

U.S. PATENT DOCUMENTS

| | | | |
|---|---|---|---|
| 5,593,886 | A | 1/1997 | Gaddy |
| 6,368,819 | B1 | 4/2002 | Gaddy |
| 7,704,723 | B2 | 4/2010 | Huhnke |
| 7,951,980 | B2 | 5/2011 | Reimann |
| 7,972,824 | B2 | 7/2011 | Simpson |
| 8,222,013 | B2 | 7/2012 | Simpson |
| 8,293,509 | B2 | 10/2012 | Simpson |
| 8,323,950 | B2* | 12/2012 | Burk .................... C12N 9/0008 435/252.3 |
| 8,445,244 | B2* | 5/2013 | Burgard .................... C12P 7/16 435/183 |
| 8,658,408 | B2 | 2/2014 | Simpson |
| 8,658,845 | B2 | 2/2014 | Oroskar |
| 8,900,836 | B2 | 12/2014 | Simpson |
| 9,068,202 | B2 | 6/2015 | Tran |
| 9,284,564 | B2 | 3/2016 | Mueller |
| 9,347,076 | B2 | 5/2016 | Liew |
| 9,359,611 | B2 | 6/2016 | Koepke |
| 9,410,130 | B2 | 8/2016 | Koepke |
| 9,738,875 | B2 | 8/2017 | Koepke |
| 9,890,384 | B2 | 2/2018 | Mueller |
| 9,920,335 | B2 | 3/2018 | Medoff et al. |
| 9,994,878 | B2 | 6/2018 | Koepke |
| 10,174,303 | B2 | 1/2019 | Behrendorff et al. |
| 10,494,600 | B2 | 12/2019 | Heijstra |
| 10,590,406 | B2 | 3/2020 | Koepke |
| 10,913,958 | B2 | 2/2021 | Koepke |
| 2010/0151543 | A1 | 6/2010 | Reeves |
| 2011/0312049 | A1 | 12/2011 | Osterhout et al. |
| 2012/0045807 | A1 | 2/2012 | Simpson |
| 2013/0157322 | A1 | 6/2013 | Simpson |
| 2013/0330809 | A1 | 12/2013 | Mueller et al. |
| 2015/0147794 | A1* | 5/2015 | Chung .................... C12N 9/92 435/158 |
| 2016/0177353 | A1* | 6/2016 | Yu .................... C12N 1/12 435/123 |
| 2017/0121717 | A1* | 5/2017 | Stephanopoulos .................... C12Y 207/01047 |
| 2019/0185888 | A1* | 6/2019 | Koepke .................... C12P 7/18 |
| 2020/0048665 | A1 | 2/2020 | Simpson |

OTHER PUBLICATIONS

Islam et al., "Exploring biochemical pathways for mono-ethylene glycol (MEG) synthesis from synthesis gas," Metabolic Engineering 41:173-180 (2017).
Pereira et al., "Efficient utilization of pentoses for bioproduction of the renewable two-carbon compounds ethylene glycol and glycolate," Metabolic Engineering 34: 80-87 (2016).
Uranukul et al., Biosynthesis of monoethylene glycol in *Saccharomyces cerevisiae* utilizing native glycolytic enzymes, Metabolic Engineering, 51:20-31 (2018).
Written Opinion of the International Searching Authority for International Application No. PCT/US2018/066619, dated Apr. 18, 2019 (pp. 1-6).
Scheffen et al., "A new-to-nature carboxylation module to improve natural and synthetic CO2 fixation," Nature Catalysis | www.nature.com/natcatal, https://doi.org/10.1038/s41929-020-00557-y, Published: Jan. 4, 2021, 13 pages.
Extended European Search Report issued in corresponding European Patent Application No. 18891435.2, dated Oct. 27, 2021, 8 pages.
Ye Zhang et al: "Production of C2-C4 diols from renewable bioresources: new metabolic pathways and metabolic engineering strategies", Biotechnology for Biofuels, vol. 10, No. 1, Dec. 1, 2017 (Dec. 1, 2017), p. 299.
Bourgade et al., "Design, Analysis, and Implementation of a Novel Biochemical Pathway for Ethylene Glycol Production in Clostridium autoethanogenum," ACS Synth Biol. May 11, 2022, pp. A-K. doi: 10.1021/acssynbio.1c00624.
Khusnutdinova et al., "Exploring bacterial carboxylate reductases for the reduction of bifunctional carboxylic acids," Biotechnol J. Nov. 2017 ; 12(11): . doi:10.1002/biot.201600751. pp. 1-25.
Abrini, Arch Microbiol, 161: 345-351, 1994.
Atul, Chem Eng Sci, 59: 2881-2890, 2004.
Chiba, Section 18: Diet Formulation and Common Feed Ingredients, Animal Nutrition Handbook, 3rd revision, pp. 575-633, 2014.
Chinn, Recovery of Glycols, Sugars, and Related Multiple —OH Compounds from Dilute-Aqueous Solution by Regenerable Adsorption onto Activated Carbons, University of California Berkeley, 1999.
Dhale, Atul, et al., Chem Eng Sci, 59: 2881-2890, 2004.
Drake, Acetogenic Prokaryotes, In: The Prokaryotes, 3rd edition, p. 354, New York, NY, 2006.
Ebrahim., COBRApy: Constraints-Based Reconstruction and Analysis for Python, BMC Syst Biol, 7: 74, 2013.
Flamholz, E. Noor, A. Bar-Even, R. Milo (2012) eQuilibrator—the biochemical thermodynamics calculator, Nucleic Acids Res 40:D770-5.
Herzberger et al., Chem Rev., 116(4): 2170-2243 (2016).
Hungate, "Chapter IV A Roll Tube Method for Cultivation of Strict Anaerobes," Methods in Microbiology, vol. 3, Part B, 1969, pp. 117-132.
Jensen, Optlang: An Algebraic Modeling Language for Mathematical Optimization, The Journal of Open Source Software, 2. doi:10.21105/joss.00139, 2017.
Köpke, Curr Opin Biotechnol, 22: 320-325, 2011.
Maia, Proceedings of the Genetic and Evolutionary Computation Conference Companion on—GECCO '17, New York, New York, ACM Press, 1661-1668, 2017.
Marcellin, Green Chem, 18: 3020-3028, 2016.
Noor et al. "An integrated open framework for thermodynamics of reactions that combines accuracy and coverage" vol. 28 No. 15, 2012, pp. 2037-2044. doi:10.1093/bioinformatics/bts317.
Noor et al. "Consistent Estimation of Gibbs Energy Using Component Contributions" Jul. 2013, vol. 9, Issue 7, e1003098.
Noor et al. "Pathway Thermodynamics Highlights Kinetic Obstacles in Central Metabolism" PLOS Computational Biology, Feb. 2014, vol. 10, Issue 2, e1003483.
Perez, Biotechnol Bioeng, 110:1066-1077, 2012.
Ragsdale, Biochim Biophys Acta, 1784: 1873-1898, 2008.
Tanner, Int J System Bacteriol, 43:232-236, 1993.
Tirado-Acevedo, Production of bioethanol from synthesis gas using Clostridium Ijungdahlii, PhD thesis, North Carolina State University, 2010.
Williams et al., "Conjugative plasmid transfer from *Escherichia coli* to Clostridium acetobutylicum," J Gen Microbiol. May 1990; 136(5): 819-26.doi:10.1099/00221287-136-5-819. 1990.
Wolfe, "Microbial Formation of Methane," Advances in Microbial Physiology, vol. 6, 1971, pp. 107-146.
Xiao et al., Ind Eng Chem Res. 54(22): 5862-5869 (2015).

\* cited by examiner

SEQUENCE LISTING

```
<160> NUMBER OF SEQ ID NOS: 82

<210> SEQ ID NO 1
<211> LENGTH: 1101
<212> TYPE: DNA
<213> ORGANISM: Artificial Sequence
<220> FEATURE:
<223> OTHER INFORMATION: Codon-adapted nucleotide sequence

<400> SEQUENCE: 1
atggtacatt atggattaaa gggaataact tgtgtagaaa cttctatatc tcatatagat      60
ggagaaaagg gaaggcttat atacagagga catcatgcta aggacatagc actaaatcat     120
agctttgaag aggctgctta tttaatctta tttggaaagc tcccaagtac agaagagctt     180
caagtcttca aagacaaatt ggcagcagaa agaaatttac cagaacatat agaaagactt     240
attcaatcct taccaaataa tatggatgat atgtcagttt taagaactgt tgtaagtgca     300
cttggtgaaa atacctatac atttcatcct aaaacagaag aggctataag acttatagca     360
ataactcctt ccataattgc ttatagaaaa agatggacaa gaggtgaaca agcaatagca     420
ccatcatcac aatatggaca tgttgaaaat tattattaca tgcttacagg agaacagcct     480
agtgaggcta agaaaaaagc acttgaaacc tatatgatat tagctacaga acatggcatg     540
```

-continued

```
aatgcttcta cttttctgc aagagtaact ttaagcactg aatcagattt agtatcagca      600
gtaacagcag cattaggtac tatgaaggga ccactacatg gcggcgctcc ctctgcagtt      660
acaaagatgt tagaagacat aggagaaaag gaacatgcag aggcttatct aaaagaaaaa      720
cttgaaaagg gagagagact catgggtttt ggacatagag tatacaagac taaagatcct      780
agagcagaag cattaagaca aaaggcagaa gaagtggcag gaaatgatag agatcttgat      840
cttgcattgc acgttgaagc agaggctata agattacttg aaatatataa accaggaaga      900
aaactttata ctaatgttga attttatgca gctgctgtta tgagggctat agactttgac      960
gatgaattat ttactcctac tttttccgct tctcgtatgg ttggatggtg tgcgcatgtg     1020
cttgaacagg cagagaataa catgattttt agaccatctg cacaatatac aggtgctatc     1080
ccagaagaag tactttctta a                                                1101
```

<210> SEQ ID NO 2
<211> LENGTH: 366
<212> TYPE: PRT
<213> ORGANISM: Bacillus subtilis

<400> SEQUENCE: 2

```
Met Val His Tyr Gly Leu Lys Gly Ile Thr Cys Val Glu Thr Ser Ile
  1               5                  10                  15

Ser His Ile Asp Gly Glu Lys Gly Arg Leu Ile Tyr Arg Gly His His
                 20                  25                  30

Ala Lys Asp Ile Ala Leu Asn His Ser Phe Glu Glu Ala Ala Tyr Leu
             35                  40                  45

Ile Leu Phe Gly Lys Leu Pro Ser Thr Glu Glu Leu Gln Val Phe Lys
 50                  55                  60

Asp Lys Leu Ala Ala Glu Arg Asn Leu Pro Glu His Ile Glu Arg Leu
 65                  70                  75                  80

Ile Gln Ser Leu Pro Asn Asn Met Asp Asp Met Ser Val Leu Arg Thr
                 85                  90                  95

Val Val Ser Ala Leu Gly Glu Asn Thr Tyr Thr Phe His Pro Lys Thr
            100                 105                 110

Glu Glu Ala Ile Arg Leu Ile Ala Ile Thr Pro Ser Ile Ile Ala Tyr
        115                 120                 125

Arg Lys Arg Trp Thr Arg Gly Glu Gln Ala Ile Ala Pro Ser Ser Gln
    130                 135                 140

Tyr Gly His Val Glu Asn Tyr Tyr Met Leu Thr Gly Glu Gln Pro
145                 150                 155                 160

Ser Glu Ala Lys Lys Lys Ala Leu Glu Thr Tyr Met Ile Leu Ala Thr
                165                 170                 175

Glu His Gly Met Asn Ala Ser Thr Phe Ser Ala Arg Val Thr Leu Ser
            180                 185                 190

Thr Glu Ser Asp Leu Val Ser Ala Val Thr Ala Ala Leu Gly Thr Met
        195                 200                 205

Lys Gly Pro Leu His Gly Gly Ala Pro Ser Ala Val Thr Lys Met Leu
    210                 215                 220

Glu Asp Ile Gly Glu Lys Glu His Ala Glu Ala Tyr Leu Lys Glu Lys
225                 230                 235                 240

Leu Glu Lys Gly Glu Arg Leu Met Gly Phe Gly His Arg Val Tyr Lys
                245                 250                 255

Thr Lys Asp Pro Arg Ala Glu Ala Leu Arg Gln Lys Ala Glu Glu Val
            260                 265                 270
```

```
Ala Gly Asn Asp Arg Asp Leu Asp Leu Ala Leu His Val Glu Ala Glu
        275                 280                 285

Ala Ile Arg Leu Leu Glu Ile Tyr Lys Pro Gly Arg Lys Leu Tyr Thr
    290                 295                 300

Asn Val Glu Phe Tyr Ala Ala Val Met Arg Ala Ile Asp Phe Asp
305                 310                 315                 320

Asp Glu Leu Phe Thr Pro Thr Phe Ser Ala Ser Arg Met Val Gly Trp
                325                 330                 335

Cys Ala His Val Leu Glu Gln Ala Glu Asn Asn Met Ile Phe Arg Pro
            340                 345                 350

Ser Ala Gln Tyr Thr Gly Ala Ile Pro Glu Glu Val Leu Ser
        355                 360                 365

<210> SEQ ID NO 3
<211> LENGTH: 1362
<212> TYPE: DNA
<213> ORGANISM: Artificial Sequence
<220> FEATURE:
<223> OTHER INFORMATION: Codon-adapted nucleotide sequence

<400> SEQUENCE: 3
atgaaaaaat gttcttacga ctataaatta ataatgtaa atgatcctaa cttctataaa      60
gatatattcc cttatgaaga agtacctaaa atagtattta ataatattca attaccaatg    120
gatctgcctg ataacatata cataactgat actaccttcc gtgatggaca acaatcaatg    180 cctcctttata caagtagaga aatagtaagg atttttgatt atttgcatga attagacaac    240
aattcaggaa taataaaaca aacagaattt ttttatata ccaaaaaaga tagaaaagca     300
gctgaagttt gtatggaaag aggatacgag ttccctgaag ttacttcttg gattagggca    360
gataaagagg acttaaaatt agttaaggat atgggcataa aggaaacagg tatgttaatg    420
agttgttcag actatcacat atttaagaaa ttaaaaatga caagaaaaga gacaatggat    480
atgtatcttg atttagctag agaggctcta aataatggta ttagacctag atgtcattta    540
gaagatatta caagagcaga tttttatgga tttgtagtac cttttgtaaa tgaacttatg    600
aaaatgagca agaggcaaa catcccaata aaaataaggg cttgtgatac tcttggatta    660
ggggtacctt ataatggagt tgaaatacca agatctgtac agggaataat tcatggtttg    720
agaaacatat gtgaagttcc ttctgaatct attgaatggc atggacataa tgatttctat    780
ggagtagtaa ctaactcctc cacggcatgg ctatatggag caagcagcat aaacacttcc    840
ttcttgggaa taggagaaag aacaggaaac tgtccacttg aagcaatgat atttgaatat    900
gctcaaataa aggaaatac taaaaatatg aaacttcatg taataacgga gcttgctcaa    960
tattttgaaa aggaaataaa atattctgta cctgttagaa ctccttttgt tggaactgat   1020
tttaatgtaa caagggctgg catacatgca gatggtatcc taaaagatga gaaatatat    1080 aatatttttg atacagataa gatactggga aggcctgtag tagtagctgt tcccagtat    1140 tcaggaaggg ctggaatagc agcatgggtg aacacttatt ataggcttaa agatgaagat   1200
aaagttaata aaaatgacag cagaatagat caaattaaaa tgtgggtaga tgagcaatac   1260
cgcgctggta ggacatcagt aattggaaac aatgaactag aacttttagt ttcaaaagta   1320
atgccagaag taatagaaaa aacagaagaa agggcttctt aa                       1362

<210> SEQ ID NO 4
<211> LENGTH: 453
<212> TYPE: PRT
```

<213> ORGANISM: Clostridium kluyveri

<400> SEQUENCE: 4

Met Lys Lys Cys Ser Tyr Asp Tyr Lys Leu Asn Asn Val Asn Asp Pro
1               5                   10                  15

Asn Phe Tyr Lys Asp Ile Phe Pro Tyr Glu Glu Val Pro Lys Ile Val
            20                  25                  30

Phe Asn Asn Ile Gln Leu Pro Met Asp Leu Pro Asp Asn Ile Tyr Ile
            35                  40                  45

Thr Asp Thr Thr Phe Arg Asp Gly Gln Gln Ser Met Pro Pro Tyr Thr
        50                  55                  60

Ser Arg Glu Ile Val Arg Ile Phe Asp Tyr Leu His Glu Leu Asp Asn
65                  70                  75                  80

Asn Ser Gly Ile Ile Lys Gln Thr Glu Phe Phe Leu Tyr Thr Lys Lys
                85                  90                  95

Asp Arg Lys Ala Ala Glu Val Cys Met Glu Arg Gly Tyr Glu Phe Pro
            100                 105                 110

Glu Val Thr Ser Trp Ile Arg Ala Asp Lys Glu Asp Leu Lys Leu Val
        115                 120                 125

Lys Asp Met Gly Ile Lys Glu Thr Gly Met Leu Met Ser Cys Ser Asp
130                 135                 140

Tyr His Ile Phe Lys Lys Leu Lys Met Thr Arg Lys Glu Thr Met Asp
145                 150                 155                 160

Met Tyr Leu Asp Leu Ala Arg Glu Ala Leu Asn Asn Gly Ile Arg Pro
                165                 170                 175

Arg Cys His Leu Glu Asp Ile Thr Arg Ala Asp Phe Tyr Gly Phe Val
            180                 185                 190

Val Pro Phe Val Asn Glu Leu Met Lys Met Ser Lys Glu Ala Asn Ile
        195                 200                 205

Pro Ile Lys Ile Arg Ala Cys Asp Thr Leu Gly Leu Gly Val Pro Tyr
210                 215                 220

Asn Gly Val Glu Ile Pro Arg Ser Val Gln Gly Ile Ile His Gly Leu
225                 230                 235                 240

Arg Asn Ile Cys Glu Val Pro Ser Glu Ser Ile Glu Trp His Gly His
                245                 250                 255

Asn Asp Phe Tyr Gly Val Val Thr Asn Ser Ser Thr Ala Trp Leu Tyr
            260                 265                 270

Gly Ala Ser Ser Ile Asn Thr Ser Phe Leu Gly Ile Gly Glu Arg Thr
        275                 280                 285

Gly Asn Cys Pro Leu Glu Ala Met Ile Phe Glu Tyr Ala Gln Ile Lys
290                 295                 300

Gly Asn Thr Lys Asn Met Lys Leu His Val Ile Thr Glu Leu Ala Gln
305                 310                 315                 320

Tyr Phe Glu Lys Glu Ile Lys Tyr Ser Val Pro Val Arg Thr Pro Phe
                325                 330                 335

Val Gly Thr Asp Phe Asn Val Thr Arg Ala Gly Ile His Ala Asp Gly
            340                 345                 350

Ile Leu Lys Asp Glu Glu Ile Tyr Asn Ile Phe Asp Thr Asp Lys Ile
        355                 360                 365

Leu Gly Arg Pro Val Val Val Ala Val Ser Gln Tyr Ser Gly Arg Ala
    370                 375                 380

Gly Ile Ala Ala Trp Val Asn Thr Tyr Tyr Arg Leu Lys Asp Glu Asp
385                 390                 395                 400

```
Lys Val Asn Lys Asn Asp Ser Arg Ile Asp Gln Ile Lys Met Trp Val
            405                 410                 415

Asp Glu Gln Tyr Arg Ala Gly Arg Thr Ser Val Ile Gly Asn Asn Glu
        420                 425                 430

Leu Glu Leu Leu Val Ser Lys Val Met Pro Glu Val Ile Glu Lys Thr
    435                 440                 445

Glu Glu Arg Ala Ser
    450

<210> SEQ ID NO 5
<211> LENGTH: 1359
<212> TYPE: DNA
<213> ORGANISM: Artificial Sequence
<220> FEATURE:
<223> OTHER INFORMATION: Codon-adapted nucleotide sequence

<400> SEQUENCE: 5
atgtcaataa acaacatagg tcctttact  aaatcccact tagatatgtg tattaaaaac      60
aattcaattg atgatgcctt gtatgaaaag tatggagtaa agagatcact tagagatctt    120
aatggtattg aataaaatgc tgggataaca aatgtcagtt tgtcaaagtc ttttactaca    180
gatgaaaatg gtaacagagt accttgtgca ggagagttat attatagagg atacgagatt    240
catgatctta taagggatt  ttttttggac aatagatttg gatttgagga atgtacttat    300
ttgttacttt ttggcgtact tcctgacgaa aaagaacttc aaaatttcaa acaagtctta    360
aatatctctt acgatttacc tcatcatttt atacaagatg ttataatgaa atctcctaca    420
gcagacataa tagctaatat gactaaatcc acgcttgcac taggttccta tgataaaaag    480
atgggagata actcacttga aaatgtcctt caacaatgta ttcaattaat atctatgttt    540
ccaaggcttg ctgtatactc ctatcagggt tatagacatt atgaattagg taaatcttgc    600
tatatacaca aacctcttcc agaattaagt tttgcagaaa atatattatc aactcttaga    660
tcaaatagaa aatatacaag attggaagca agagtacttg atcttgccct agttttacac    720
atggaacatg gcggcggctc aaattctact tttactacaa gggtagttac ttcatcagga    780
agtgatacgt atgcaactat ggcagcagca ttatgttcat taaaaggacc tttaaatggc    840
ggcggcgatt atcaagtaat gggtatgatg aagaatataa gagataatgt aagtgatata    900
actgacgaag aagaagttgg tgaatatatt agaaaaattg taaccgtgaa agcgtatgat    960
aaaacaggaa tagtatacgg aatgggtcat ccattctata gcatatctga cccaagggct   1020
ttagagttca agaaatatgt aaaattactt gcagcagaaa aaggaatgga tgaagaatat   1080
gcattatatg aaatgataga aaggattgca ccagaaatta tcgcagaaga aggaagata    1140 tataaaggag tatgtattaa tatagattat tattctggtt tgctttataa aatgttaaag   1200
atcccagcag agatgtttac tccattattt gctattgcca gagttgtagg atggtcggca   1260
catagaatgg aagaacttgt aaattcttac aaaatcataa gacctgctta tacatctata   1320
gcagagataa aggaatacgt acctataaat gaaagataa                           1359

<210> SEQ ID NO 6
<211> LENGTH: 452
<212> TYPE: PRT
<213> ORGANISM: Clostridium sp. L2-50

<400> SEQUENCE: 6

Met Ser Ile Asn Asn Ile Gly Pro Phe Thr Lys Ser His Leu Asp Met
1               5                   10                  15
```

-continued

```
Cys Ile Lys Asn Asn Ser Ile Asp Asp Ala Leu Tyr Glu Lys Tyr Gly
                 20                  25                  30

Val Lys Arg Ser Leu Arg Asp Leu Asn Gly Ile Gly Ile Asn Ala Gly
             35                  40                  45

Ile Thr Asn Val Ser Leu Ser Lys Ser Phe Thr Thr Asp Glu Asn Gly
         50                  55                  60

Asn Arg Val Pro Cys Ala Gly Glu Leu Tyr Tyr Arg Gly Tyr Glu Ile
 65                  70                  75                  80

His Asp Leu Ile Lys Gly Phe Phe Leu Asp Asn Arg Phe Gly Phe Glu
                 85                  90                  95

Glu Cys Thr Tyr Leu Leu Leu Phe Gly Val Leu Pro Asp Glu Lys Glu
            100                 105                 110

Leu Gln Asn Phe Lys Gln Val Leu Asn Ile Ser Tyr Asp Leu Pro His
            115                 120                 125

His Phe Ile Gln Asp Val Ile Met Lys Ser Pro Thr Ala Asp Ile Ile
            130                 135                 140

Ala Asn Met Thr Lys Ser Thr Leu Ala Leu Gly Ser Tyr Asp Lys Lys
145                 150                 155                 160

Met Gly Asp Asn Ser Leu Glu Asn Val Leu Gln Gln Cys Ile Gln Leu
                165                 170                 175

Ile Ser Met Phe Pro Arg Leu Ala Val Tyr Ser Tyr Gln Gly Tyr Arg
            180                 185                 190

His Tyr Glu Leu Gly Lys Ser Cys Tyr Ile His Lys Pro Leu Pro Glu
            195                 200                 205

Leu Ser Phe Ala Glu Asn Ile Leu Ser Thr Leu Arg Ser Asn Arg Lys
210                 215                 220

Tyr Thr Arg Leu Glu Ala Arg Val Leu Asp Leu Ala Leu Val Leu His
225                 230                 235                 240

Met Glu His Gly Gly Gly Ser Asn Ser Thr Phe Thr Arg Val Val
                245                 250                 255

Thr Ser Ser Gly Ser Asp Thr Tyr Ala Thr Met Ala Ala Ala Leu Cys
            260                 265                 270

Ser Leu Lys Gly Pro Leu Asn Gly Gly Asp Tyr Gln Val Met Gly
            275                 280                 285

Met Met Lys Asn Ile Arg Asp Asn Val Ser Asp Ile Thr Asp Glu Glu
290                 295                 300

Glu Val Gly Glu Tyr Ile Arg Lys Ile Val Asn Arg Glu Ala Tyr Asp
305                 310                 315                 320

Lys Thr Gly Ile Val Tyr Gly Met Gly His Pro Phe Tyr Ser Ile Ser
            325                 330                 335

Asp Pro Arg Ala Leu Glu Phe Lys Lys Tyr Val Lys Leu Leu Ala Ala
            340                 345                 350

Glu Lys Gly Met Asp Glu Glu Tyr Ala Leu Tyr Glu Met Ile Glu Arg
            355                 360                 365

Ile Ala Pro Glu Ile Ile Ala Glu Glu Arg Lys Ile Tyr Lys Gly Val
            370                 375                 380

Cys Ile Asn Ile Asp Tyr Tyr Ser Gly Leu Leu Tyr Lys Met Leu Lys
385                 390                 395                 400

Ile Pro Ala Glu Met Phe Thr Pro Leu Phe Ala Ile Ala Arg Val Val
                405                 410                 415

Gly Trp Ser Ala His Arg Met Glu Glu Leu Val Asn Ser Tyr Lys Ile
            420                 425                 430

Ile Arg Pro Ala Tyr Thr Ser Ile Ala Glu Ile Lys Glu Tyr Val Pro
```

```
            435                 440                 445
Ile Asn Glu Arg
    450
```

<210> SEQ ID NO 7
<211> LENGTH: 1119
<212> TYPE: DNA
<213> ORGANISM: Artificial Sequence
<220> FEATURE:
<223> OTHER INFORMATION: Codon-adapted nucleotide sequence

<400> SEQUENCE: 7

| | | | | | |
|---|---|---|---|---|---|
| atgacagcaa | caaggggcct | tgaaggggta | gtagcgacta | ctagtagtgt | aagttcaatt       60 |
| atagatgata | ctttgactta | tgttggatat | gatatagatg | atcttacgga | aaatgcaagc      120 |
| tttgaagaaa | taatatattt | attgtggcat | ttgagattac | aaacaaaaa  | ggaattagaa      180 |
| gaattaaaac | aacaattagc | caaagaggca | gctgttcctc | aggaaataat | agaacatttc      240 |
| aaatcctata | gcttagaaaa | tgttcatcct | atggctgcac | ttagaactgc | tatatccctc      300 |
| ttaggtcttt | tggattctga | ggcagatact | atgaatccag | aggctaacta | tagaaaagca      360 |
| ataagattac | aggctaaagt | cccaggatta | gttgcagcat | tttcaagaat | acgaaaagga      420 |
| ttagaaccag | tagagccaag | agaagattac | ggaatagcag | agaattttt  | gtatactttg      480 |
| aatggcgaag | agcctagtcc | aatagaagtt | gaagcattta | taaagcact  | tatacttcat      540 |
| gctgaccatg | aacttaacgc | atctacattt | acagctagag | tttgtgtagc | cactctttct      600 |
| gatatttatt | ccggcattac | tgctgcaatt | ggggctctta | agggacctct | acatggcggc      660 |
| gccaacgagg | gtgtaatgaa | gatgttaaca | gagattggag | aggttgaaaa | tgctgaacct      720 |
| tatataagag | ccaaacttga | aaaaaaggaa | aaaataatgg | gatttggtca | tagagtatac      780 |
| aaacatggag | atcctagagc | aaaacatctt | aaagaaatgt | caaagagact | tacaaattta      840 |
| acaggtgaat | caaaatggta | tgaaatgagt | attcgtattg | aagatatagt | tacgtcagag      900 |
| aagaaacttc | cccctaatgt | agattttac  | agtgcatctg | tttatcattc | gcttggaatc      960 |
| gatcacgatt | tatttacgcc | tatatttgct | gtaagtagaa | tgagcggatg | gttagctcat     1020 |
| attctcgaac | agtacgacaa | taacagactt | ataagaccac | gtgctgatta | tacaggtcct     1080 |
| gacaaacaaa | aatttgtacc | tatagaagaa | agagcataa  |            |                 1119 |

<210> SEQ ID NO 8
<211> LENGTH: 372
<212> TYPE: PRT
<213> ORGANISM: Bacillus subtilis

<400> SEQUENCE: 8

```
Met Thr Ala Thr Arg Gly Leu Glu Gly Val Val Ala Thr Thr Ser Ser
1               5                   10                  15

Val Ser Ser Ile Ile Asp Asp Thr Leu Thr Tyr Val Gly Tyr Asp Ile
            20                  25                  30

Asp Asp Leu Thr Glu Asn Ala Ser Phe Glu Glu Ile Ile Tyr Leu Leu
        35                  40                  45

Trp His Leu Arg Leu Pro Asn Lys Lys Glu Leu Glu Glu Leu Lys Gln
    50                  55                  60

Gln Leu Ala Lys Glu Ala Ala Val Pro Gln Glu Ile Ile Glu His Phe
65                  70                  75                  80

Lys Ser Tyr Ser Leu Glu Asn Val His Pro Met Ala Ala Leu Arg Thr
                85                  90                  95
```

```
Ala Ile Ser Leu Leu Gly Leu Leu Asp Ser Glu Ala Asp Thr Met Asn
            100                 105                 110

Pro Glu Ala Asn Tyr Arg Lys Ala Ile Arg Leu Gln Ala Lys Val Pro
        115                 120                 125

Gly Leu Val Ala Ala Phe Ser Arg Ile Arg Lys Gly Leu Glu Pro Val
    130                 135                 140

Glu Pro Arg Glu Asp Tyr Gly Ile Ala Glu Asn Phe Leu Tyr Thr Leu
145                 150                 155                 160

Asn Gly Glu Glu Pro Ser Pro Ile Glu Val Glu Ala Phe Asn Lys Ala
            165                 170                 175

Leu Ile Leu His Ala Asp His Glu Leu Asn Ala Ser Thr Phe Thr Ala
        180                 185                 190

Arg Val Cys Val Ala Thr Leu Ser Asp Ile Tyr Ser Gly Ile Thr Ala
    195                 200                 205

Ala Ile Gly Ala Leu Lys Gly Pro Leu His Gly Gly Ala Asn Glu Gly
210                 215                 220

Val Met Lys Met Leu Thr Glu Ile Gly Glu Val Glu Asn Ala Glu Pro
225                 230                 235                 240

Tyr Ile Arg Ala Lys Leu Glu Lys Lys Glu Lys Ile Met Gly Phe Gly
            245                 250                 255

His Arg Val Tyr Lys His Gly Asp Pro Arg Ala Lys His Leu Lys Glu
        260                 265                 270

Met Ser Lys Arg Leu Thr Asn Leu Thr Gly Glu Ser Lys Trp Tyr Glu
    275                 280                 285

Met Ser Ile Arg Ile Glu Asp Ile Val Thr Ser Glu Lys Lys Leu Pro
290                 295                 300

Pro Asn Val Asp Phe Tyr Ser Ala Ser Val Tyr His Ser Leu Gly Ile
305                 310                 315                 320

Asp His Asp Leu Phe Thr Pro Ile Phe Ala Val Ser Arg Met Ser Gly
            325                 330                 335

Trp Leu Ala His Ile Leu Glu Gln Tyr Asp Asn Asn Arg Leu Ile Arg
        340                 345                 350

Pro Arg Ala Asp Tyr Thr Gly Pro Asp Lys Gln Lys Phe Val Pro Ile
    355                 360                 365

Glu Glu Arg Ala
    370

<210> SEQ ID NO 9
<211> LENGTH: 1785
<212> TYPE: DNA
<213> ORGANISM: Artificial Sequence
<220> FEATURE:
<223> OTHER INFORMATION: Codon-adapted nucleotide sequence

<400> SEQUENCE: 9
atgcaaatta tggaagaaga aggaagattt gaagcagaag tggcagaagt agaaagttgg      60
tggggaacag agcgttttag gcttactaaa aggccttata cggcaaggga cgttgtactt     120
ttaagaggaa ccttgagaca gtcttatgcc agtggcgaga tggctaagaa attatggaga     180
actttaaaag cgcatcaggc tggcggcact gcttcaagaa cttttggtgc tttagatcca     240
gttcaagtta caatgatggc taagcaccta gatactattt atgtaagcgg atggcagtgt     300
tcatctacac acacatcaac aaatgaacct ggcccagatc ttgcagacta tccttatgat     360
actgtgccaa ataaggtaga acatcttttt tttgctcaat tatatcatga ccgcaagcaa     420
agagaggcaa gaatgagtct tccgcgagca gaaagagccc gtgctcctta tgtagatttt     480
```

```
ttaaaaccta taatagcaga tggagatact ggatttggcg gcgccacagc tacagttaaa    540
ctttgtaaac ttttttgtaga gagaggtgct gcgggagttc accttgagga tcaatcatct    600
gttacaaaaa aatgtggaca catggctgga aaagttttag tggcagtttc agagcatgtt    660
aataggcttg tagctgctag acttcaattt gacgttatgg gcgtggagac agttttagtg    720
gcaaggacag atgcagtagc agctacactt atacaaacta atgtagatgc cagggatcac    780
caattcatag taggagccac aaatccagga ttgagaggtc agtctcttgc agctgtatta    840
tctgctggta tgtcagctgg taagagcgga agagaattgc aagcaatcga agatgaatgg    900
ctagcagcag cacaattaaa gactttttagc gaatgtgtac gagatgctat tgcaggacta    960
ggcgtggcag caaaggaaaa gcaaagaaga ctccaagaat gggacagggc aacaggcggc   1020
tatgatagat gtgtaagcaa tgatcaagca agagatatcg cagcatccct ggagtaact   1080 tctgtattct gggattggga tttgcctaga actagagaag gttttttacag attcagaggc   1140 tcagtagctg ccgcagtagt tagaggcaga gcatttgctc cacatgcaga tgtattatgg   1200
atggaaacat cttcaccaaa tgtggcagaa tgtactgcat tttcagaagg agttaaggca   1260
gcatgtccag aagcaatgct cgcgtataat ttgtcaccat cctttaactg ggacgcaagt   1320
ggcatgacag atgcagaaat ggcagcattt attccatctg tagctagatt gggatatgta   1380
tggcaattta taactcttgc tggttttcat gctgatgcct tggttacaga tacttttgct   1440
agggattttg ctagaagagg tatgttagct tatgttgaaa gaatacagag agaagaaaga   1500
ataaatggtg tagaaactct tgaacatcaa aaatggtcag gagcaaattt ttacgaccgt   1560
gtgttgaaag cagtacaagg cggcataagc agtactgcag ctatgggaaa aggtaaagta   1620
cctcacttcc cagcattctt tttttgctta gaaaaaaata agccatcatt cgttcacagt   1680
tttgatgtag tactttttac aggtgttaca gaggaacaat tcaaagatcc aaggcctgcc   1740
actggttcaa gtggacttca ggttatggcc aaatcacgta tttaa               1785
```

<210> SEQ ID NO 10
<211> LENGTH: 594
<212> TYPE: PRT
<213> ORGANISM: Zea mays

<400> SEQUENCE: 10

```
Met Gln Ile Met Glu Glu Glu Gly Arg Phe Glu Ala Glu Val Ala Glu
1               5                   10                  15

Val Glu Ser Trp Trp Gly Thr Glu Arg Phe Arg Leu Thr Lys Arg Pro
            20                  25                  30

Tyr Thr Ala Arg Asp Val Val Leu Leu Arg Gly Thr Leu Arg Gln Ser
        35                  40                  45

Tyr Ala Ser Gly Glu Met Ala Lys Lys Leu Trp Arg Thr Leu Lys Ala
    50                  55                  60

His Gln Ala Gly Gly Thr Ala Ser Arg Thr Phe Gly Ala Leu Asp Pro
65                  70                  75                  80

Val Gln Val Thr Met Met Ala Lys His Leu Asp Thr Ile Tyr Val Ser
                85                  90                  95

Gly Trp Gln Cys Ser Ser Thr His Thr Ser Thr Asn Glu Pro Gly Pro
            100                 105                 110

Asp Leu Ala Asp Tyr Pro Tyr Asp Thr Val Pro Asn Lys Val Glu His
        115                 120                 125

Leu Phe Phe Ala Gln Leu Tyr His Asp Arg Lys Gln Arg Glu Ala Arg
    130                 135                 140
```

```
Met Ser Leu Pro Arg Ala Glu Arg Ala Arg Ala Pro Tyr Val Asp Phe
145                 150                 155                 160

Leu Lys Pro Ile Ile Ala Asp Gly Asp Thr Gly Phe Gly Gly Ala Thr
                165                 170                 175

Ala Thr Val Lys Leu Cys Lys Leu Phe Val Glu Arg Gly Ala Ala Gly
            180                 185                 190

Val His Leu Glu Asp Gln Ser Ser Val Thr Lys Lys Cys Gly His Met
        195                 200                 205

Ala Gly Lys Val Leu Val Ala Val Ser Glu His Val Asn Arg Leu Val
    210                 215                 220

Ala Ala Arg Leu Gln Phe Asp Val Met Gly Val Glu Thr Val Leu Val
225                 230                 235                 240

Ala Arg Thr Asp Ala Val Ala Ala Thr Leu Ile Gln Thr Asn Val Asp
                245                 250                 255

Ala Arg Asp His Gln Phe Ile Val Gly Ala Thr Asn Pro Gly Leu Arg
            260                 265                 270

Gly Gln Ser Leu Ala Ala Val Leu Ser Ala Gly Met Ser Ala Gly Lys
        275                 280                 285

Ser Gly Arg Glu Leu Gln Ala Ile Glu Asp Glu Trp Leu Ala Ala
    290                 295                 300

Gln Leu Lys Thr Phe Ser Glu Cys Val Arg Asp Ala Ile Ala Gly Leu
305                 310                 315                 320

Gly Val Ala Ala Lys Glu Lys Gln Arg Arg Leu Gln Glu Trp Asp Arg
                325                 330                 335

Ala Thr Gly Gly Tyr Asp Arg Cys Val Ser Asn Asp Gln Ala Arg Asp
            340                 345                 350

Ile Ala Ala Ser Leu Gly Val Thr Ser Val Phe Trp Asp Trp Asp Leu
        355                 360                 365

Pro Arg Thr Arg Glu Gly Phe Tyr Arg Phe Arg Gly Ser Val Ala Ala
    370                 375                 380

Ala Val Val Arg Gly Arg Ala Phe Ala Pro His Ala Asp Val Leu Trp
385                 390                 395                 400

Met Glu Thr Ser Ser Pro Asn Val Ala Glu Cys Thr Ala Phe Ser Glu
                405                 410                 415

Gly Val Lys Ala Ala Cys Pro Glu Ala Met Leu Ala Tyr Asn Leu Ser
            420                 425                 430

Pro Ser Phe Asn Trp Asp Ala Ser Gly Met Thr Asp Ala Glu Met Ala
        435                 440                 445

Ala Phe Ile Pro Ser Val Ala Arg Leu Gly Tyr Val Trp Gln Phe Ile
    450                 455                 460

Thr Leu Ala Gly Phe His Ala Asp Ala Leu Val Thr Asp Thr Phe Ala
465                 470                 475                 480

Arg Asp Phe Ala Arg Arg Gly Met Leu Ala Tyr Val Glu Arg Ile Gln
                485                 490                 495

Arg Glu Glu Arg Ile Asn Gly Val Glu Thr Leu Glu His Gln Lys Trp
            500                 505                 510

Ser Gly Ala Asn Phe Tyr Asp Arg Val Leu Lys Ala Val Gln Gly Gly
        515                 520                 525

Ile Ser Ser Thr Ala Ala Met Gly Lys Gly Lys Val Pro His Phe Pro
    530                 535                 540

Ala Phe Phe Phe Cys Leu Glu Lys Asn Lys Pro Ser Phe Val His Ser
545                 550                 555                 560
```

```
Phe Asp Val Val Leu Phe Thr Gly Val Thr Glu Glu Gln Phe Lys Asp
                565                 570                 575

Pro Arg Pro Ala Thr Gly Ser Ser Gly Leu Gln Val Met Ala Lys Ser
            580                 585                 590

Arg Ile

<210> SEQ ID NO 11
<211> LENGTH: 1305
<212> TYPE: DNA
<213> ORGANISM: Artificial Sequence
<220> FEATURE:
<223> OTHER INFORMATION: Codon-adapted nucleotide sequence

<400> SEQUENCE: 11
atgaaaacaa gaactcaaca aatagaagaa ttacaaaaag aatggacgca accaagatgg      60
gaaggtatta cgaggcctta ttctgcagaa gatgtagtaa aattaagagg ttctgtaaat     120
ccagaatgta ctcttgccca gcttggagca gctaaaatgt ggagactttt gcacggtgaa     180
tcaaagaagg gttatataaa ctctcttggc gctttaacag cggccaggc acttcaacag      240 gctaaggcag aatagaagc agtttatctt tctggatggc aagtagcagc agatgcaaat     300
ttagcagcat caatgtatcc tgatcagagc ttatacccag caattcagt cccagctgta     360 gtagagagaa taaataatac ctttagaagg gcagatcaaa ttcaatggtc tgctggtatt     420
gaaccaggtg atccaagata cgtggattat ttttgccaa ttgtagcaga tgctgaggct     480
ggttttggcg gcgtattaaa tgcatttgaa ttaatgaaag caatgataga ggctggtgct     540
gcagctgtcc attttgaaga tcagttagct tcagttaaga aatgtggaca catgggcggc     600
aaggtattag ttccaaccca agaagcaata caaaaattag tggcagctag acttgcagct     660
gatgtaacag gtgtgcctac attactagtt gcaagaacag atgcagatgc tgcagatctt     720
attactagtg actgtgatcc ttatgattca gaatttatta caggagaaag aaccagtgag     780 ggattttta gaactcatgc aggaataaga caggctatat caagaggatt agcttatgct     840
ccttatgcag atcttgttg tgtgaaaaca tctacaccag atctcgaact tgcccgtaga     900
tttgcccagg caatacatgc taagtatcca ggaaaattat tagcgtacaa ttgttctcct     960
tcatttaatt ggcagaagaa cttagatgac aaaacaatag caagttttca gcaacaatta    1020
tcagatatgg gatacaaatt tcagttcata acattagctg gaatacatag tatgtggttt    1080
aatatgtttg atcttgcaaa tgcttatgca caaggagaag gcatgaagca ttatgtagaa    1140
aaagtacaac agccagaatt tgcagctgcc aaggatggat atactttcgt ttctcatcaa    1200
caagaggttg gaactggata ttttgataag gttacaacaa ttatacaggg cggcacatcg    1260
tctgttactg cactaacagg ttcaactgaa gaatctcaat tttaa                    1305

<210> SEQ ID NO 12
<211> LENGTH: 434
<212> TYPE: PRT
<213> ORGANISM: Escherichia coli

<400> SEQUENCE: 12

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45
```

Gly Ala Ala Lys Met Trp Arg Leu Leu His Gly Glu Ser Lys Lys Gly
50                  55                  60

Tyr Ile Asn Ser Leu Gly Ala Leu Thr Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Glu Arg Ile Asn Asn Thr Phe
        115                 120                 125

Arg Arg Ala Asp Gln Ile Gln Trp Ser Ala Gly Ile Glu Pro Gly Asp
130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe

<210> SEQ ID NO 13
<211> LENGTH: 1218
<212> TYPE: DNA
<213> ORGANISM: Artificial Sequence

```
<220> FEATURE:
<223> OTHER INFORMATION: Codon-adapted nucleotide sequence

<400> SEQUENCE: 13
atgacagtta ctccacattt atttataccg ggcccaacaa acataccaga tgcagtacgt      60
atggcaatga atatacctat ggaagacatg cgttcaccag agttcccaaa atttacatta     120
cctttatttg aggatttaaa aaaagcattt aagatgaaag atggaagagt ttttatattt     180
ccatcttcag gaacaggcgc atgggaatca gctgtagaaa acactcttgc cactggagat     240
aaggttttaa tgtcaagatt tggacaattt tctttgctat gggtagatat gtgtgaaaga     300
ttgggattaa aagttgaagt atgtgatgaa gaatggggaa caggagtgcc agtagaaaaa     360
tatgctgata tacttgctaa agataaaaat catgaaataa aggctgtttt tgtaactcac     420
aatgaaacag caacaggtgt ttcttcagat gtggctggtg taagaaaagc acttgacgca     480
gcaaagcatc cagcactttt gatggtggat ggagtatcat cagttggttc tcttgatatg     540
agaatgggtg aatggggagt tgattgctgt gtatctggaa gccaaaaggg ttttatgctt     600
cctacaggtt tgggcatttt agctgtgtca cagaaggcat tagatattaa taaatcaaag     660
aatggcagaa tgaatagatg ctttttttcc tttgaggata tgataaaaac taatgatcag     720
ggttttttc cttataccc cgccactcaa ttattgagag gattaagaac ttctctcgat      780
cttttgttcg cagaaggact agataatgta tttgcaagac atactagatt agctagtgga     840
gttagggctg ccgtagatgc atggggatta aaattgtgtg caaagaaacc taaatggtat     900
tccgatactg tatcagcaat tttagttcca gaaggtattg attccaatgc tataacaaaa     960
acagcttatt atagatataa tacaagtttt ggtcttggat taaataaggt tgcaggaaaa    1020
gtattcagaa taggccattt aggtatgtta gatgaagtaa tgataggcgg cgctttattt    1080
gcagcagaga tggcacttaa agataatgga gtaaatctaa aattaggatc tggaacaggt    1140
gcagctgctg aatattttag taaaaatgct acaaagtctg ctactgcttt aactccaaaa    1200
caagcaaaag cggcataa                                                  1218

<210> SEQ ID NO 14
<211> LENGTH: 405
<212> TYPE: PRT
<213> ORGANISM: Hyphomicrobium methylovorum

<400> SEQUENCE: 14

Met Thr Val Thr Pro His Leu Phe Ile Pro Gly Pro Thr Asn Ile Pro
1               5                   10                  15

Asp Ala Val Arg Met Ala Met Asn Ile Pro Met Glu Asp Met Arg Ser
                20                  25                  30

Pro Glu Phe Pro Lys Phe Thr Leu Pro Leu Phe Glu Asp Leu Lys Lys
            35                  40                  45

Ala Phe Lys Met Lys Asp Gly Arg Val Phe Ile Phe Pro Ser Ser Gly
        50                  55                  60

Thr Gly Ala Trp Glu Ser Ala Val Glu Asn Thr Leu Ala Thr Gly Asp
65                  70                  75                  80

Lys Val Leu Met Ser Arg Phe Gly Gln Phe Ser Leu Leu Trp Val Asp
                85                  90                  95

Met Cys Glu Arg Leu Gly Leu Lys Val Glu Val Cys Asp Glu Glu Trp
            100                 105                 110

Gly Thr Gly Val Pro Val Glu Lys Tyr Ala Asp Ile Leu Ala Lys Asp
        115                 120                 125
```

Lys Asn His Glu Ile Lys Ala Val Phe Val Thr His Asn Glu Thr Ala
            130                 135                 140

Thr Gly Val Ser Ser Asp Val Ala Gly Val Arg Lys Ala Leu Asp Ala
145                 150                 155                 160

Ala Lys His Pro Ala Leu Leu Met Val Asp Gly Val Ser Ser Val Gly
                165                 170                 175

Ser Leu Asp Met Arg Met Gly Glu Trp Gly Val Asp Cys Cys Val Ser
            180                 185                 190

Gly Ser Gln Lys Gly Phe Met Leu Pro Thr Gly Leu Gly Ile Leu Ala
        195                 200                 205

Val Ser Gln Lys Ala Leu Asp Ile Asn Lys Ser Lys Asn Gly Arg Met
210                 215                 220

Asn Arg Cys Phe Phe Ser Phe Glu Asp Met Ile Lys Thr Asn Asp Gln
225                 230                 235                 240

Gly Phe Phe Pro Tyr Thr Pro Ala Thr Gln Leu Leu Arg Gly Leu Arg
                245                 250                 255

Thr Ser Leu Asp Leu Leu Phe Ala Glu Gly Leu Asp Asn Val Phe Ala
            260                 265                 270

Arg His Thr Arg Leu Ala Ser Gly Val Arg Ala Ala Val Asp Ala Trp
        275                 280                 285

Gly Leu Lys Leu Cys Ala Lys Glu Pro Lys Trp Tyr Ser Asp Thr Val
290                 295                 300

Ser Ala Ile Leu Val Pro Glu Gly Ile Asp Ser Asn Ala Ile Thr Lys
305                 310                 315                 320

Thr Ala Tyr Tyr Arg Tyr Asn Thr Ser Phe Gly Leu Gly Leu Asn Lys
                325                 330                 335

Val Ala Gly Lys Val Phe Arg Ile Gly His Leu Gly Met Leu Asp Glu
            340                 345                 350

Val Met Ile Gly Gly Ala Leu Phe Ala Ala Glu Met Ala Leu Lys Asp
        355                 360                 365

Asn Gly Val Asn Leu Lys Leu Gly Ser Gly Thr Gly Ala Ala Ala Glu
370                 375                 380

Tyr Phe Ser Lys Asn Ala Thr Lys Ser Ala Thr Ala Leu Thr Pro Lys
385                 390                 395                 400

Gln Ala Lys Ala Ala
                405

<210> SEQ ID NO 15
<211> LENGTH: 1185
<212> TYPE: DNA
<213> ORGANISM: Artificial Sequence
<220> FEATURE:
<223> OTHER INFORMATION: Codon-adapted nucleotide sequence

<400> SEQUENCE: 15
atgcaattta ggccttttaa tccaccagtt agaactctta tgggaccagg accaagcgat       60
gtacacccaa gaatattaga ggctatgagc cgtcctacaa taggacattt ggatcctgct      120
tttatacaga tgatggaaga agtaaaaact ttacttcagt atgcatttca aactaaaaat      180
gaacttacta tgccagtaag tgccccaggc tctgcaggca tggaaacatg ctttgccaac      240
ttagtagaac aggtgatca ggttatagtt tgccagaatg gtgtatttgg cggcagaatg      300
aaagaaaatg tagaaagatg tggcggcata cctataatgg ttgaagatac ttggggagag      360
gctgttgatc cagataaatt ggagactgca ttaaaggcta atccagaggc ttgtatagtg      420
gcatttgttc atgctgaaac tagtactggt gcacaaagtg atgctgaaac attggtaaaa      480

```
ttagctcatc agtatgattg tcttactata gttgatgctg ttacatcact tggcggcact      540
ccaataaagg tagatgaatg ggaaatagat gctatttata gtggaactca gaaatgcctt      600
tcatgtactc caggactttc accagtaagt ttcaatgaaa gggctcttga aaaaattagg      660
aacagaaaac aaaaagttca gtcgtggttt atggatttaa atctagttat gggatattgg      720
ggcggcggcg caaagcgtgc ttatcatcat acagcaccaa ttaatgcttt atatggactt      780
catgaggcac ttttgatgct tcaggaagag ggattagaga acgcatgggc aaggcaccaa      840
aaaaatcatc ttgctttacg ggctggactg gaagcaatgg gcctcacttt tatagtaaat      900
gaaggagata gactgcctca gttaaatgct gtatctatac cagagggagt tgatgatggt      960
gctgttagat caaggcttct aaacgaatat aacttagaaa ttggtgctgg gttaggtgct     1020
ttagctggga aggtatggag aataggctta atgggtcatg caagtagagc agaaaatatt     1080
ctcttatgca aagttcatt agaggctata ttaagtgaga tgggtgctga catatctcaa     1140
ggtgtggcta ttccagcaat gcagaaggca cttgcgcaag cataa                     1185
```

<210> SEQ ID NO 16
<211> LENGTH: 394
<212> TYPE: PRT
<213> ORGANISM: Sedimenticola thiotaurini

<400> SEQUENCE: 16

```
Met Gln Phe Arg Pro Phe Asn Pro Pro Val Arg Thr Leu Met Gly Pro
1               5                   10                  15

Gly Pro Ser Asp Val His Pro Arg Ile Leu Glu Ala Met Ser Arg Pro
            20                  25                  30

Thr Ile Gly His Leu Asp Pro Ala Phe Ile Gln Met Met Glu Glu Val
        35                  40                  45

Lys Thr Leu Leu Gln Tyr Ala Phe Gln Thr Lys Asn Glu Leu Thr Met
    50                  55                  60

Pro Val Ser Ala Pro Gly Ser Ala Gly Met Glu Thr Cys Phe Ala Asn
65                  70                  75                  80

Leu Val Glu Pro Gly Asp Gln Val Ile Val Cys Gln Asn Gly Val Phe
                85                  90                  95

Gly Gly Arg Met Lys Glu Asn Val Glu Arg Cys Gly Gly Ile Pro Ile
            100                 105                 110

Met Val Glu Asp Thr Trp Gly Glu Ala Val Asp Pro Asp Lys Leu Glu
        115                 120                 125

Thr Ala Leu Lys Ala Asn Pro Glu Ala Cys Ile Val Ala Phe Val His
    130                 135                 140

Ala Glu Thr Ser Thr Gly Ala Gln Ser Asp Ala Glu Thr Leu Val Lys
145                 150                 155                 160

Leu Ala His Gln Tyr Asp Cys Leu Thr Ile Val Asp Ala Val Thr Ser
                165                 170                 175

Leu Gly Gly Thr Pro Ile Lys Val Asp Glu Trp Glu Ile Asp Ala Ile
            180                 185                 190

Tyr Ser Gly Thr Gln Lys Cys Leu Ser Cys Thr Pro Gly Leu Ser Pro
        195                 200                 205

Val Ser Phe Asn Glu Arg Ala Leu Glu Lys Ile Arg Asn Arg Lys Gln
    210                 215                 220

Lys Val Gln Ser Trp Phe Met Asp Leu Asn Leu Val Met Gly Tyr Trp
225                 230                 235                 240

Gly Gly Gly Ala Lys Arg Ala Tyr His His Thr Ala Pro Ile Asn Ala
```

```
                   245                 250                 255
Leu Tyr Gly Leu His Glu Ala Leu Leu Met Leu Gln Glu Glu Gly Leu
            260                 265                 270

Glu Asn Ala Trp Ala Arg His Gln Lys Asn His Leu Ala Leu Arg Ala
        275                 280                 285

Gly Leu Glu Ala Met Gly Leu Thr Phe Ile Val Asn Glu Gly Asp Arg
    290                 295                 300

Leu Pro Gln Leu Asn Ala Val Ser Ile Pro Glu Gly Val Asp Asp Gly
305                 310                 315                 320

Ala Val Arg Ser Arg Leu Leu Asn Glu Tyr Asn Leu Glu Ile Gly Ala
                325                 330                 335

Gly Leu Gly Ala Leu Ala Gly Lys Val Trp Arg Ile Gly Leu Met Gly
            340                 345                 350

His Ala Ser Arg Ala Glu Asn Ile Leu Leu Cys Ile Ser Ser Leu Glu
        355                 360                 365

Ala Ile Leu Ser Glu Met Gly Ala Asp Ile Ser Gln Gly Val Ala Ile
    370                 375                 380

Pro Ala Met Gln Lys Ala Leu Ala Gln Ala
385                 390

<210> SEQ ID NO 17
<211> LENGTH: 1185
<212> TYPE: DNA
<213> ORGANISM: Artificial Sequence
<220> FEATURE:
<223> OTHER INFORMATION: Codon-adapted nucleotide sequence

<400> SEQUENCE: 17
atgcggactc attcatttca cccaccagtt agaactctta tgggaccagg accttctgat      60
gtaaatccaa gagtacttga ggcaatgtca cgacctacaa ttggacactt agatcctgta    120
tttgtagata tgatggaaga attaaagagt ttgcttcaat atgcatttca aacaggaaat    180
caattaacta tgcctgtaag tggacctggc tcagctggaa tggaaacatg ttttgttaat    240
ctagttgaac ctggagataa agtaatagtt tgtcaaaatg gagtatttgg cggcaggatg    300
aaagaaaatg tagaaagatg tggcggcaca gcagtcatgg tggaagatgc atggggttcc    360
gcagttgacc cacaaaaact aaagatgca cttcaggcac atcctgatgc taaattagtt    420
gcttttgttc atgctgaaac tagtacagga gcacaaagcg atgcaaaggc tttagtagaa    480
attgctcata gacatgactg cttagtaatt gtggatacag ttacctcatt aggcggcact    540
cctgtaaaag tagatgaatg gggaatagat gcagtttatt caggaaccca aaaatgctta    600
tcatgtaccc caggtctttc accagtatct ttctctgaaa gggctatgga agaataaaa    660 cataggaaaa ctaaagtaca gtcttggttt atggatttaa atcttgttat ggctattgg    720 ggatcaggag caaaagggc ttatcatcat actgctccta taaatgcatt gtacggtctt    780
cacgaagcat tagttatact tcaagaagag gggttagaaa atgcatgggc aagacatgct    840
catgctcata gagcactatt agctggtatt gaagcaatgg gattaaaatt tgtagtaaag    900
gaagatgaac ggttaccgca attaaatgct gtaggtattc cagaaggcgt agatgatgca    960
gctgtgcgtg cccagctcct tcaagattat aaccacgaaa taggtgctgg tcttggacct   1020
atggcaggaa aaatctggag aataggtctt atgggctatg gtgctaatcc taaaaatgta   1080
cttttctgct taggagcatt agaggatgta ctttcgcgca tgagggctcc tatagaaaga   1140
ggtgctgctc ttccagcagc tcatgctgca cttggcgctg cataa                   1185
```

```
<210> SEQ ID NO 18
<211> LENGTH: 394
<212> TYPE: PRT
<213> ORGANISM: Thermithiobacillus tepidarius

<400> SEQUENCE: 18

Met Arg Thr His Ser Phe His Pro Pro Val Arg Thr Leu Met Gly Pro
1               5                   10                  15

Gly Pro Ser Asp Val Asn Pro Arg Val Leu Glu Ala Met Ser Arg Pro
            20                  25                  30

Thr Ile Gly His Leu Asp Pro Val Phe Val Asp Met Met Glu Glu Leu
        35                  40                  45

Lys Ser Leu Leu Gln Tyr Ala Phe Gln Thr Gly Asn Gln Leu Thr Met
    50                  55                  60

Pro Val Ser Gly Pro Gly Ser Ala Gly Met Glu Thr Cys Phe Val Asn
65                  70                  75                  80

Leu Val Glu Pro Gly Asp Lys Val Ile Val Cys Gln Asn Gly Val Phe
                85                  90                  95

Gly Gly Arg Met Lys Glu Asn Val Glu Arg Cys Gly Gly Thr Ala Val
            100                 105                 110

Met Val Glu Asp Ala Trp Gly Ser Ala Val Asp Pro Gln Lys Leu Lys
        115                 120                 125

Asp Ala Leu Gln Ala His Pro Asp Ala Lys Leu Val Ala Phe Val His
    130                 135                 140

Ala Glu Thr Ser Thr Gly Ala Gln Ser Asp Ala Lys Ala Leu Val Glu
145                 150                 155                 160

Ile Ala His Arg His Asp Cys Leu Val Ile Val Asp Thr Val Thr Ser
                165                 170                 175

Leu Gly Gly Thr Pro Val Lys Val Asp Glu Trp Gly Ile Asp Ala Val
            180                 185                 190

Tyr Ser Gly Thr Gln Lys Cys Leu Ser Cys Thr Pro Gly Leu Ser Pro
        195                 200                 205

Val Ser Phe Ser Glu Arg Ala Met Glu Arg Ile Lys His Arg Lys Thr
    210                 215                 220

Lys Val Gln Ser Trp Phe Met Asp Leu Asn Leu Val Met Gly Tyr Trp
225                 230                 235                 240

Gly Ser Gly Ala Lys Arg Ala Tyr His His Thr Ala Pro Ile Asn Ala
                245                 250                 255

Leu Tyr Gly Leu His Glu Ala Leu Val Ile Leu Gln Glu Glu Gly Leu
            260                 265                 270

Glu Asn Ala Trp Ala Arg His Ala His Ala His Arg Ala Leu Leu Ala
        275                 280                 285

Gly Ile Glu Ala Met Gly Leu Lys Phe Val Val Lys Glu Asp Glu Arg
    290                 295                 300

Leu Pro Gln Leu Asn Ala Val Gly Ile Pro Glu Gly Val Asp Asp Ala
305                 310                 315                 320

Ala Val Arg Ala Gln Leu Leu Gln Asp Tyr Asn His Glu Ile Gly Ala
                325                 330                 335

Gly Leu Gly Pro Met Ala Gly Lys Ile Trp Arg Ile Gly Leu Met Gly
            340                 345                 350

Tyr Gly Ala Asn Pro Lys Asn Val Leu Phe Cys Leu Gly Ala Leu Glu
        355                 360                 365

Asp Val Leu Ser Arg Met Arg Ala Pro Ile Glu Arg Gly Ala Ala Leu
    370                 375                 380
```

Pro Ala Ala His Ala Ala Leu Gly Ala Ala
385                 390

<210> SEQ ID NO 19
<211> LENGTH: 1125
<212> TYPE: DNA
<213> ORGANISM: Artificial Sequence
<220> FEATURE:
<223> OTHER INFORMATION: Codon-adapted nucleotide sequence

<400> SEQUENCE: 19

```
atgagaactc catttattat gaccccagga ccaacacaag ttcatgaaga agtaagaaag     60
gctatgtcca gagaagcaac taatcctgat ttagatgaaa atttctacga gttctataaa    120
aatacctgta ataagataaa aagattatta atacagaaa tcaggtatt aattcttgat     180
ggcgaaggta ttttaggttt ggaagcagct tgtgcaagct taactgaaca aggagataga    240
gtactttgta tagataatgg tatttttgga aagggttttg gtgattttc taaaatgtat     300
ggcggcgaag ttgtatactt cgagtctgat tatagaaagg gtatagatgt agaaaaactt    360
gaagagttcc ttaaaagaga ttctaacttc aaatacgcga cactagtaca ctgtgaaaca    420
ccagcgggta taactaatcc tatagataag atatgtactt tattaaataa atatggtgtg    480
ctttcagtag tagatagtgt aagttcagta ggcggcgatg aaataaatgt agatgagtgg    540
aaaatagata tagctttagg cggctctcaa aagtgtatat cagcgccatc aggattaact    600
ttcctttcaa tttcagaaaa agcaatggat actatgataa atagaaaaac tcctatagca    660
gcatttatt gtaatcttac aatttggaaa ggttggtatg aagaaagtg gttcccttat     720
actcagccaa ttaatgcaat atatgcactt gattgtgctt tagatagact tttagaaaca    780
gattatataa atagcataa aacaatagct aatgctacaa gagaagccct tgtaaaaagt    840
ggacttgaat tgtatccttt agattcctat tcaaatactg taactacttt tcttgtacca    900
gaaggaataa attttgaaga tgtatttgaa gatatgatga agatcacaa cataatgata    960
ggcggcgctt ttgattattt aaaaggaaaa gttattagaa taggacacat gggcgaaaac   1020
tgctatgaag aaaaaatata tataactttta aaggcacttg atacagttt aaaaaaatat    1080
ggagcaaaac taaacggaga gatttacaag cactttgtag attag                    1125
```

<210> SEQ ID NO 20
<211> LENGTH: 374
<212> TYPE: PRT
<213> ORGANISM: Clostridium acidi-urici

<400> SEQUENCE: 20

Met Arg Thr Pro Phe Ile Met Thr Pro Gly Pro Thr Gln Val His Glu
1               5                   10                  15

Glu Val Arg Lys Ala Met Ser Arg Glu Ala Thr Asn Pro Asp Leu Asp
            20                  25                  30

Glu Asn Phe Tyr Glu Phe Tyr Lys Asn Thr Cys Asn Lys Ile Lys Arg
        35                  40                  45

Leu Leu Asn Thr Glu Asn Gln Val Leu Ile Leu Asp Gly Glu Gly Ile
    50                  55                  60

Leu Gly Leu Glu Ala Ala Cys Ala Ser Leu Thr Glu Gln Gly Asp Arg
65                  70                  75                  80

Val Leu Cys Ile Asp Asn Gly Ile Phe Gly Lys Gly Phe Gly Asp Phe
                85                  90                  95

Ser Lys Met Tyr Gly Gly Glu Val Val Tyr Phe Glu Ser Asp Tyr Arg

|  | 100 |  | 105 |  | 110 |  |  |
|---|---|---|---|---|---|---|---|

Lys Gly Ile Asp Val Glu Lys Leu Glu Glu Phe Leu Lys Arg Asp Ser
                115                        120                        125

Asn Phe Lys Tyr Ala Thr Leu Val His Cys Glu Thr Pro Ala Gly Ile
   130                        135                        140

Thr Asn Pro Ile Asp Lys Ile Cys Thr Leu Leu Asn Lys Tyr Gly Val
145                     150                       155                        160

Leu Ser Val Val Asp Ser Val Ser Ser Val Gly Gly Asp Glu Ile Asn
                165                        170                       175

Val Asp Glu Trp Lys Ile Asp Ile Ala Leu Gly Gly Ser Gln Lys Cys
              180                       185                        190

Ile Ser Ala Pro Ser Gly Leu Thr Phe Leu Ser Ile Ser Glu Lys Ala
           195                       200                       205

Met Asp Thr Met Ile Asn Arg Lys Thr Pro Ile Ala Ala Phe Tyr Cys
   210                        215                        220

Asn Leu Thr Ile Trp Lys Gly Trp Tyr Glu Glu Lys Trp Phe Pro Tyr
225                     230                       235                        240

Thr Gln Pro Ile Asn Ala Ile Tyr Ala Leu Asp Cys Ala Leu Asp Arg
              245                       250                        255

Leu Leu Glu Thr Asp Tyr Ile Asn Arg His Lys Thr Ile Ala Asn Ala
           260                       265                       270

Thr Arg Glu Ala Leu Val Lys Ser Gly Leu Glu Leu Tyr Pro Leu Asp
   275                        280                        285

Ser Tyr Ser Asn Thr Val Thr Thr Phe Leu Val Pro Glu Gly Ile Asn
   290                        295                        300

Phe Glu Asp Val Phe Glu Asp Met Met Lys Asp His Asn Ile Met Ile
305                     310                       315                        320

Gly Gly Ala Phe Asp Tyr Leu Lys Gly Lys Val Ile Arg Ile Gly His
           325                       330                       335

Met Gly Glu Asn Cys Tyr Glu Glu Lys Ile Tyr Ile Thr Leu Lys Ala
              340                       345                        350

Leu Asp Thr Val Leu Lys Lys Tyr Gly Ala Lys Leu Asn Gly Glu Ile
           355                       360                       365

Tyr Lys His Phe Val Asp
   370

```
<210> SEQ ID NO 21
<211> LENGTH: 1155
<212> TYPE: DNA
<213> ORGANISM: Artificial Sequence
<220> FEATURE:
<223> OTHER INFORMATION: Codon-adapted nucleotide sequence

<400> SEQUENCE: 21
atgggaaaat ttttaaaaaa gcactatata atggcgccag acctacacc agtaccaaat      60 gatatattaa ctgaaggggc taagaaaact atacaccatc gcacgcccca atttgtatct     120
ataatggaag agacactgga atcagccaaa tatatcttcc aaactaagca caatgtttat     180
gcatttgcat ctacaggtac aggtgctatg gaagcagcag ttgctaactt ggtaagtcca     240
ggtgacaagg ttatagtagt agttgcagga aaatttgggg agagatggag agaactttgt     300
caggcttatg gtgctgatat agtagagatt gccttggagt ggggagatgc tgttactcct     360
gaacaaattg aagaagcctt aaataaaaat cctgatgcta agtagtatt tacaacttat     420 tctgaaacat caactggaac agttatagat cttgaaggaa tagctagagt tactaaagaa     480
```

```
aaagatgtgg ttctggttac agatgcagtt tcggcattag gtgctgagcc attaaaaatg      540
gatgaatggg gagtagactt agtggttaca ggttctcaaa agggacttat gcttccacca      600
ggacttgcat taataagctt aaatgataaa gcatggggat tagtagaaaa atccagatca      660
ccaagatatt actttgatct tagagcatac agaaaaagct atccagataa cccatacaca      720
ccagcagtaa atatgatata tatgctgaga aaggctcttc agatgataaa ggaagaaggt      780
attgaaaatg tatgggaaag gcatagaata ctgggtgatg ctaccagagc agcagttaaa      840
gcattagggt tagaattact gtcaaagcgt ccgggaaatg tagttacagc tgtaaaagtt      900
ccagaaggta ttgatggtaa acaaatacct aaaataatga gagataaata tggagttacc      960
attgcaggcg gccaggctaa attaaaaggt aaaattttcc gtattgccca tttaggatat     1020
atgagtccat ttgatactat cactgctata tctgcattag aacttacatt aaaggaactt     1080
ggatatgaat ttgaattagg agttggagta aaggctgcag aggcagtatt tgctaaagaa     1140
tttataggag aataa                                                      1155
```

<210> SEQ ID NO 22
<211> LENGTH: 384
<212> TYPE: PRT
<213> ORGANISM: Thermotoga maritima

<400> SEQUENCE: 22

```
Met Gly Lys Phe Leu Lys Lys His Tyr Ile Met Ala Pro Gly Pro Thr
1               5                  10                  15

Pro Val Pro Asn Asp Ile Leu Thr Glu Gly Ala Lys Glu Thr Ile His
            20                  25                  30

His Arg Thr Pro Gln Phe Val Ser Ile Met Glu Glu Thr Leu Glu Ser
        35                  40                  45

Ala Lys Tyr Ile Phe Gln Thr Lys His Asn Val Tyr Ala Phe Ala Ser
    50                  55                  60

Thr Gly Thr Gly Ala Met Glu Ala Ala Val Ala Asn Leu Val Ser Pro
65                  70                  75                  80

Gly Asp Lys Val Ile Val Val Ala Gly Lys Phe Gly Glu Arg Trp
                85                  90                  95

Arg Glu Leu Cys Gln Ala Tyr Gly Ala Asp Ile Val Glu Ile Ala Leu
            100                 105                 110

Glu Trp Gly Asp Ala Val Thr Pro Glu Gln Ile Glu Glu Ala Leu Asn
        115                 120                 125

Lys Asn Pro Asp Ala Lys Val Val Phe Thr Thr Tyr Ser Glu Thr Ser
    130                 135                 140

Thr Gly Thr Val Ile Asp Leu Glu Gly Ile Ala Arg Val Thr Lys Glu
145                 150                 155                 160

Lys Asp Val Val Leu Val Thr Asp Ala Val Ser Ala Leu Gly Ala Glu
                165                 170                 175

Pro Leu Lys Met Asp Glu Trp Gly Val Asp Leu Val Val Thr Gly Ser
            180                 185                 190

Gln Lys Gly Leu Met Leu Pro Pro Gly Leu Ala Leu Ile Ser Leu Asn
        195                 200                 205

Asp Lys Ala Trp Gly Leu Val Glu Lys Ser Arg Ser Pro Arg Tyr Tyr
    210                 215                 220

Phe Asp Leu Arg Ala Tyr Arg Lys Ser Tyr Pro Asp Asn Pro Tyr Thr
225                 230                 235                 240

Pro Ala Val Asn Met Ile Tyr Met Leu Arg Lys Ala Leu Gln Met Ile
                245                 250                 255
```

```
Lys Glu Glu Gly Ile Glu Asn Val Trp Glu Arg His Arg Ile Leu Gly
            260                 265                 270

Asp Ala Thr Arg Ala Ala Val Lys Ala Leu Gly Leu Glu Leu Leu Ser
        275                 280                 285

Lys Arg Pro Gly Asn Val Val Thr Ala Val Lys Val Pro Glu Gly Ile
    290                 295                 300

Asp Gly Lys Gln Ile Pro Lys Ile Met Arg Asp Lys Tyr Gly Val Thr
305                 310                 315                 320

Ile Ala Gly Gly Gln Ala Lys Leu Lys Gly Lys Ile Phe Arg Ile Ala
                325                 330                 335

His Leu Gly Tyr Met Ser Pro Phe Asp Thr Ile Thr Ala Ile Ser Ala
            340                 345                 350

Leu Glu Leu Thr Leu Lys Glu Leu Gly Tyr Glu Phe Glu Leu Gly Val
        355                 360                 365

Gly Val Lys Ala Ala Glu Ala Val Phe Ala Lys Glu Phe Ile Gly Glu
    370                 375                 380

<210> SEQ ID NO 23
<211> LENGTH: 1230
<212> TYPE: DNA
<213> ORGANISM: Artificial Sequence
<220> FEATURE:
<223> OTHER INFORMATION: Codon-adapted nucleotide sequence

<400> SEQUENCE: 23
atgaatttaa  gagaaactgc  actgaaattt  cataaagata  acgaaggtaa  aatagcacta      60
aaatgcaaag  ttccagtaaa  aaataaagaa  gatttgacac  ttgcctatac  accaggagtt     120
gctgaacctt  gtctagaaat  aaataagaat  cctgaatgca  tatatgatta  tacatctaaa     180
ggtaactggg  tagcagtagt  aacaaatgga  accgcagtat  taggcttagg  aaatattggt     240
gctgggctg   gtcttccagt  tatggaaggt  aaatctgtcc  ttttcaaaac  ttttgctggt     300
gtagatgcat  ttccaatctg  cttggaatca  aaagatataa  atgaaatagt  agctgcagta     360
aaattaatgg  aacctacatt  tggcggcata  aatttagagg  atataaaggc  accagaatgt     420
tttgaaatag  aatcaaaact  taagagggtc  tgtaatatac  agtattccat  gatgatcag     480
catggtactg  cagttgtatc  ttctgcatgt  cttataaatg  cactaaaaat  agtaaataag     540
aaatttgagg  acctaaaaat  agtagtaaat  ggtgcgggtg  ctgctggaac  agctattact     600
aaattactta  taaaaatggg  tacaaaaaat  gtaatacttt  gtgacactaa  gggcgctatt     660
tataagagaa  ggcctatagg  catgaataag  ttcaaagatg  aaatggctga  ataacaaat     720
ccaaatcttc  aaaaaggcac  actagcagat  gtattaaaag  gtgctgatgt  cttccttgga     780
gtttctgctg  caaattgtgt  tacagaagaa  atggtaaaat  caatgaataa  ggattcaata     840
ataatggcaa  tggctaatcc  aaacccagaa  atattaccag  atttagctat  aaaggctggt     900
gctaaagtag  tatgtactgg  acggagtgac  tttcctaacc  aagtaaacaa  tgttttagct     960
tttcccggta  tatttagagg  agcgttggat  gtaagagcat  cagaaataaa  tgatgaaatg    1020
aaaattgctg  ctgcttatgc  tatagcagaa  ttagtttcag  aagaagaatt  aaaacctgat    1080
tatattatac  caaatgcatt  tgatttgaga  atagctccta  agtagcagc   ttatgtagca    1140
aaagcagcaa  tagatacagg  agtggcaaga  agaaagatg   ttacaccaga  aatggttgaa    1200
aagcacacaa  aaactttgct  tggcatttaa                                       1230

<210> SEQ ID NO 24
```

<211> LENGTH: 409
<212> TYPE: PRT
<213> ORGANISM: Clostridium autoethanogenum

<400> SEQUENCE: 24

| Met | Asn | Leu | Arg | Glu | Thr | Ala | Leu | Lys | Phe | His | Lys | Asp | Asn | Glu | Gly |
|---|---|---|---|---|---|---|---|---|---|---|---|---|---|---|---|
| 1 | | | | 5 | | | | | 10 | | | | | 15 | |

| Lys | Ile | Ala | Leu | Lys | Cys | Lys | Val | Pro | Val | Lys | Asn | Lys | Glu | Asp | Leu |
| | | | 20 | | | | | 25 | | | | | 30 | | |

| Thr | Leu | Ala | Tyr | Thr | Pro | Gly | Val | Ala | Glu | Pro | Cys | Leu | Glu | Ile | Asn |
| | | 35 | | | | | 40 | | | | | 45 | | | |

| Lys | Asn | Pro | Glu | Cys | Ile | Tyr | Asp | Tyr | Thr | Ser | Lys | Gly | Asn | Trp | Val |
| 50 | | | | | 55 | | | | | 60 | | | | | |

| Ala | Val | Val | Thr | Asn | Gly | Thr | Ala | Val | Leu | Gly | Leu | Gly | Asn | Ile | Gly |
| 65 | | | | | 70 | | | | | 75 | | | | | 80 |

| Ala | Gly | Ala | Gly | Leu | Pro | Val | Met | Glu | Gly | Lys | Ser | Val | Leu | Phe | Lys |
| | | | | 85 | | | | | 90 | | | | | 95 | |

| Thr | Phe | Ala | Gly | Val | Asp | Ala | Phe | Pro | Ile | Cys | Leu | Glu | Ser | Lys | Asp |
| | | | 100 | | | | | 105 | | | | | 110 | | |

| Ile | Asn | Glu | Ile | Val | Ala | Ala | Val | Lys | Leu | Met | Glu | Pro | Thr | Phe | Gly |
| | | | 115 | | | | | 120 | | | | | 125 | | |

| Gly | Ile | Asn | Leu | Glu | Asp | Ile | Lys | Ala | Pro | Glu | Cys | Phe | Glu | Ile | Glu |
| 130 | | | | | 135 | | | | | 140 | | | | | |

| Ser | Lys | Leu | Lys | Glu | Val | Cys | Asn | Ile | Pro | Val | Phe | His | Asp | Asp | Gln |
| 145 | | | | | 150 | | | | | 155 | | | | | 160 |

| His | Gly | Thr | Ala | Val | Ser | Ser | Ala | Cys | Leu | Ile | Asn | Ala | Leu | Lys |
| | | | | 165 | | | | | 170 | | | | | 175 |

| Ile | Val | Asn | Lys | Lys | Phe | Glu | Asp | Leu | Lys | Ile | Val | Val | Asn | Gly | Ala |
| | | | 180 | | | | | 185 | | | | | 190 | | |

| Gly | Ala | Ala | Gly | Thr | Ala | Ile | Thr | Lys | Leu | Leu | Ile | Lys | Met | Gly | Thr |
| | | | 195 | | | | | 200 | | | | | 205 | | |

| Lys | Asn | Val | Ile | Leu | Cys | Asp | Thr | Lys | Gly | Ala | Ile | Tyr | Lys | Arg | Arg |
| | 210 | | | | | 215 | | | | | 220 | | | | |

| Pro | Ile | Gly | Met | Asn | Lys | Phe | Lys | Asp | Glu | Met | Ala | Glu | Ile | Thr | Asn |
| 225 | | | | | 230 | | | | | 235 | | | | | 240 |

| Pro | Asn | Leu | Gln | Lys | Gly | Thr | Leu | Ala | Asp | Val | Leu | Lys | Gly | Ala | Asp |
| | | | | 245 | | | | | 250 | | | | | 255 | |

| Val | Phe | Leu | Gly | Val | Ser | Ala | Ala | Asn | Cys | Val | Thr | Glu | Glu | Met | Val |
| | | | 260 | | | | | 265 | | | | | 270 | | |

| Lys | Ser | Met | Asn | Lys | Asp | Ser | Ile | Ile | Met | Ala | Met | Ala | Asn | Pro | Asn |
| | | 275 | | | | | 280 | | | | | 285 | | | |

| Pro | Glu | Ile | Leu | Pro | Asp | Leu | Ala | Ile | Lys | Ala | Gly | Ala | Lys | Val | Val |
| | 290 | | | | | 295 | | | | | 300 | | | | |

| Cys | Thr | Gly | Arg | Ser | Asp | Phe | Pro | Asn | Gln | Val | Asn | Asn | Val | Leu | Ala |
| 305 | | | | | 310 | | | | | 315 | | | | | 320 |

| Phe | Pro | Gly | Ile | Phe | Arg | Gly | Ala | Leu | Asp | Val | Arg | Ala | Ser | Glu | Ile |
| | | | | 325 | | | | | 330 | | | | | 335 | |

| Asn | Asp | Glu | Met | Lys | Ile | Ala | Ala | Ala | Tyr | Ala | Ile | Ala | Glu | Leu | Val |
| | | | 340 | | | | | 345 | | | | | 350 | | |

| Ser | Glu | Glu | Leu | Lys | Pro | Asp | Tyr | Ile | Ile | Pro | Asn | Ala | Phe | Asp |
| | | | 355 | | | | | 360 | | | | | 365 | |

| Leu | Arg | Ile | Ala | Pro | Lys | Val | Ala | Ala | Tyr | Val | Ala | Lys | Ala | Ala | Ile |
| | 370 | | | | | 375 | | | | | 380 | | | | |

| Asp | Thr | Gly | Val | Ala | Arg | Lys | Lys | Asp | Val | Thr | Pro | Glu | Met | Val | Glu |

```
385                 390                 395                 400
Lys His Thr Lys Thr Leu Leu Gly Ile
            405

<210> SEQ ID NO 25
<211> LENGTH: 1173
<212> TYPE: DNA
<213> ORGANISM: Artificial Sequence
<220> FEATURE:
<223> OTHER INFORMATION: Codon-adapted nucleotide sequence

<400> SEQUENCE: 25
atgaatgtaa aagaaaaatc acttaagctg catagagaaa acatggaac aatagaaata      60 gtaggaacaa tgcctttaag aaatggtgat gatcttgcag tagcttatac tcctggagta    120
gctggtcctt gcttagaaat agctaaggat gaagaaaagg cttatgaata ctataaaa      180 ggaaaaacag ttgctgtagt tactaatggt acagctgttc ttggacttgg aaatatagga    240
cctgctgcag gacttcctgt tgtagaagga aaggctttac ttttgaaaag atttgcaaat    300
gtaaatgcta tacctatatg tgtagattct acagatccag atgatatcgt taatacaata    360
aaaaatatag ctccaggatt tggcggcata catctggaag atataaaggc tccagaatgt    420
ttctacatag aagataaact taaggaagaa ttagatatac ctatatacca tgatgatcaa    480
catggtactg ccatcgctgt tttagctgga ttgtataatg cattaaaaat agttaacaaa    540
gatatatcag atataaaagt tgtaataaat ggtgctggtg ctagtggtat agctacagca    600
aaacttctca tatctgcagg agtaaaaaat attgtccttt gtgacattaa tggaatagtt    660
tatgaaggtg acaattgctt aaatgagcct cagaaacaaa tagcaaaagt aactaacaga    720
ggactggcaa agggaacatt aaaagatgct atgaaaaatg cagatgtatt cattggagtt    780
tctgctggta atgtggtaac tggagaaatg gttgaaggta tgaataaaga ttctataata    840
tttgctttag ctaatcctac accagaaatt atgcctgaag aagcaaaaaa ggctggtgct    900
aaagttatag caacaggaag atctgatttt ccaaaccaaa ttaacaatgt tcttgtattc    960
cctggtatct tcaaaggtgc tctttcagta agggctaagg aaatatgtga cgaaatgaaa   1020
atagcagctg caagggact agcaaatcta gtaagaagg acgagcttaa tgaagaatat   1080
ataataccat cagttttcaa tagaaatgta tgtgatgcag tttccaaggc tgttatggat   1140
gtagcacaaa aaataataa atttactgca taa                                1173

<210> SEQ ID NO 26
<211> LENGTH: 390
<212> TYPE: PRT
<213> ORGANISM: Clostridium autoethanogenum

<400> SEQUENCE: 26

Met Asn Val Lys Glu Lys Ser Leu Lys Leu His Arg Glu Lys His Gly
1               5                   10                  15

Thr Ile Glu Ile Val Gly Thr Met Pro Leu Arg Asn Gly Asp Asp Leu
            20                  25                  30

Ala Val Ala Tyr Thr Pro Gly Val Ala Gly Pro Cys Leu Glu Ile Ala
        35                  40                  45

Lys Asp Glu Glu Lys Ala Tyr Glu Tyr Thr Ile Lys Gly Lys Thr Val
    50                  55                  60

Ala Val Val Thr Asn Gly Thr Ala Val Leu Gly Leu Gly Asn Ile Gly
65                  70                  75                  80

Pro Ala Ala Gly Leu Pro Val Val Glu Gly Lys Ala Leu Leu Leu Lys
```

```
            85                  90                  95
Arg Phe Ala Asn Val Asn Ala Ile Pro Ile Cys Val Asp Ser Thr Asp
            100                 105                 110

Pro Asp Asp Ile Val Asn Thr Ile Lys Asn Ile Ala Pro Gly Phe Gly
            115                 120                 125

Gly Ile His Leu Glu Asp Ile Lys Ala Pro Glu Cys Phe Tyr Ile Glu
            130                 135                 140

Asp Lys Leu Lys Glu Glu Leu Asp Ile Pro Ile Tyr His Asp Asp Gln
145                 150                 155                 160

His Gly Thr Ala Ile Ala Val Leu Ala Gly Leu Tyr Asn Ala Leu Lys
            165                 170                 175

Ile Val Asn Lys Asp Ile Ser Asp Ile Lys Val Val Ile Asn Gly Ala
            180                 185                 190

Gly Ala Ser Gly Ile Ala Thr Ala Lys Leu Leu Ile Ser Ala Gly Val
            195                 200                 205

Lys Asn Ile Val Leu Cys Asp Ile Asn Gly Ile Val Tyr Glu Gly Asp
            210                 215                 220

Asn Cys Leu Asn Glu Pro Gln Lys Gln Ile Ala Lys Val Thr Asn Arg
225                 230                 235                 240

Gly Leu Ala Lys Gly Thr Leu Lys Asp Ala Met Lys Asn Ala Asp Val
            245                 250                 255

Phe Ile Gly Val Ser Ala Gly Asn Val Val Thr Gly Glu Met Val Glu
            260                 265                 270

Gly Met Asn Lys Asp Ser Ile Ile Phe Ala Leu Ala Asn Pro Thr Pro
            275                 280                 285

Glu Ile Met Pro Glu Glu Ala Lys Lys Ala Gly Ala Lys Val Ile Ala
            290                 295                 300

Thr Gly Arg Ser Asp Phe Pro Asn Gln Ile Asn Asn Val Leu Val Phe
305                 310                 315                 320

Pro Gly Ile Phe Lys Gly Ala Leu Ser Val Arg Ala Lys Glu Ile Cys
            325                 330                 335

Asp Glu Met Lys Ile Ala Ala Lys Gly Leu Ala Asn Leu Val Lys
            340                 345                 350

Lys Asp Glu Leu Asn Glu Glu Tyr Ile Ile Pro Ser Val Phe Asn Arg
            355                 360                 365

Asn Val Cys Asp Ala Val Ser Lys Ala Val Met Asp Val Ala Gln Lys
            370                 375                 380

Asn Asn Lys Phe Thr Ala
385                 390

<210> SEQ ID NO 27
<211> LENGTH: 2187
<212> TYPE: DNA
<213> ORGANISM: Artificial Sequence
<220> FEATURE:
<223> OTHER INFORMATION: Codon-adapted nucleotide sequence

<400> SEQUENCE: 27
atgactaact atgaaaaggt aggtaaatta caagtagcaa cggaattata taactttgta      60
aaggaagaag tttaccagg acttgaaata caaaatgagc aattctggac aaattttgat     120
tcgcttattc atgaacttgc cccagaaaat aaggcacttt tggaaaaaag ggacgagctt     180
cagaagacca tatcagaatg gcatcaaaat aataaggag aaatagattt tgctaaatac      240
aaagagttct tacaagaaat aggatatctt gaaccagttc cagaagattt caaagttact     300
```

```
acagctaatg tagacaatga agtggctaat caggctggtt ctcaattagt tgtacctata    360
gataatgcaa gatatgctct aaacgctgct aatgcccgct ggggatcact ttatgatgca    420
ttatatggta gtgacgttat aagcgatgag gctggagcag aggctggtgt ccagtataat    480
cctataagag gtcaaaaggt aatagatttt gcaaaaaatt tattagatca agcagctcct    540
cttgcagaag gttctcatgc tgatgtaacc gcctacaaaa ttgttgaagg aaaacttcag    600
gttactttgg aatctggtaa tactgcttta cttcaagatg aatccaaatt tgtaggatat    660
aatggaagtg aggatgcacc gacggcagta ctccttgtaa caacgggct tcatattgaa    720
atagcaatag ataaaaataa tcctatagga aatctgaca aggctggtgt taaggacctt    780
gttttagagg ctgcactttc gactttaatg gactgtgagg attcaattgc tgcagtagat    840
gcagaggata agtaggcgt atatagaaat tggcttggac ttatgaaagg agatttagaa    900
agcacttta agagaggatc aaaaactgtt acaagaaagc tgaacgctga cagaacctat    960
acaggtgatg gtaaacaatt aactctcagg ggacgtagtc ttatgtttgt gagaaatgtg   1020
ggacatttaa tgactaacaa tgctatattg gatgaaaacg gaaatgaagt tccagaaggt   1080
atcttagatg gagtattaac aagtcttata gcaactcata atttcaaaga aaatgcagag   1140
ttcaaaaaca gccttcacaa gagtatatat attgttaaac caaaaatgca ttcaccagca   1200
gaagcagctt ttgctaataa gttatttgat agaatagaag atttacttgg agtagaaaga   1260
aatactatta aaattggtgt tatggatgaa gaaagaagaa tgtcattaaa tttaaagtct   1320
gcaataaatg aagttaaaga aagaatagct tttattaata caggattcct tgatagaact   1380
ggagatgaaa tacacacttc tatggaagca ggacctgtaa ttagaaaggc tgacatgaag   1440
acttcagaat ggctttcttc ttatgaatca gctaatgtag ctgtaggaat aggagcagga   1500
ttaccaggac atgcacagat tggaaaggga atgtgggcaa tgccagacct tatggcagca   1560
atgcttgaac aaaaaatagc acatcctaag gctggggctt caacagcatg ggttccttct   1620
ccaactgcag ctatattgca tgcccttcac tatcatgagg taaacgttaa agaagttcag   1680
gctggtattg atagttctat agattataga gatggaatat tagatatacc tcttgctcca   1740
aatgcagact ggagcgctga ggaagttcag tctgaattag acaacaatgc acaaggaata   1800
cttggatatg ttgtgcgctg gattgatcaa ggtgtaggat gcagcactgt accagatatt   1860
aatgatgttg gtcttatgga agatagggct actctccgta tttcaagtca gcatatagct   1920
aattggctta gacatggtgt gtgtactaaa gaacaggtag aggaaacttt agagagaatg   1980
gctaaagttg tagaccaaca aaatgcagat gatgaacttt atcaaccaat ggcaccaaac   2040
tacgacgatt caattgcatt ccaggctgca tcagacttaa tttttcaaagg agcagagcaa   2100
cctagtgggt atactgagcc aatcctacat gcaagaagaa tagaagcaaa ggctaaggct   2160
aaacaaaaag caacagtaca gaattag                                      2187
```

<210> SEQ ID NO 28
<211> LENGTH: 728
<212> TYPE: PRT
<213> ORGANISM: Sporosarcina sp. P30

<400> SEQUENCE: 28

```
Met Thr Asn Tyr Glu Lys Val Gly Lys Leu Gln Val Ala Thr Glu Leu
1               5                   10                  15

Tyr Asn Phe Val Lys Glu Glu Val Leu Pro Gly Leu Glu Ile Gln Asn
            20                  25                  30

Glu Gln Phe Trp Thr Asn Phe Asp Ser Leu Ile His Glu Leu Ala Pro
```

```
                    35                  40                  45
Glu Asn Lys Ala Leu Leu Glu Lys Arg Asp Glu Leu Gln Lys Thr Ile
 50                  55                  60
Ser Glu Trp His Gln Asn Asn Lys Gly Glu Ile Asp Phe Ala Lys Tyr
 65                  70                  75                  80
Lys Glu Phe Leu Gln Glu Ile Gly Tyr Leu Glu Pro Val Pro Glu Asp
                     85                  90                  95
Phe Lys Val Thr Thr Ala Asn Val Asp Asn Glu Val Ala Asn Gln Ala
                    100                 105                 110
Gly Ser Gln Leu Val Val Pro Ile Asp Asn Ala Arg Tyr Ala Leu Asn
                115                 120                 125
Ala Ala Asn Ala Arg Trp Gly Ser Leu Tyr Asp Ala Leu Tyr Gly Ser
            130                 135                 140
Asp Val Ile Ser Asp Glu Ala Gly Ala Glu Ala Gly Val Gln Tyr Asn
145                 150                 155                 160
Pro Ile Arg Gly Gln Lys Val Ile Asp Phe Ala Lys Asn Leu Leu Asp
                165                 170                 175
Gln Ala Ala Pro Leu Ala Glu Gly Ser His Ala Asp Val Thr Ala Tyr
                180                 185                 190
Lys Ile Val Glu Gly Lys Leu Gln Val Thr Leu Glu Ser Gly Asn Thr
                195                 200                 205
Ala Leu Leu Gln Asp Glu Ser Lys Phe Val Gly Tyr Asn Gly Ser Glu
            210                 215                 220
Asp Ala Pro Thr Ala Val Leu Leu Val Asn Asn Gly Leu His Ile Glu
225                 230                 235                 240
Ile Ala Ile Asp Lys Asn Asn Pro Ile Gly Lys Ser Asp Lys Ala Gly
                245                 250                 255
Val Lys Asp Leu Val Leu Glu Ala Ala Leu Ser Thr Leu Met Asp Cys
                260                 265                 270
Glu Asp Ser Ile Ala Ala Val Asp Ala Glu Asp Lys Val Gly Val Tyr
            275                 280                 285
Arg Asn Trp Leu Gly Leu Met Lys Gly Asp Leu Glu Ser Thr Phe Lys
290                 295                 300
Arg Gly Ser Lys Thr Val Thr Arg Lys Leu Asn Ala Asp Arg Thr Tyr
305                 310                 315                 320
Thr Gly Asp Gly Lys Gln Leu Thr Leu Arg Gly Arg Ser Leu Met Phe
                325                 330                 335
Val Arg Asn Val Gly His Leu Met Thr Asn Asn Ala Ile Leu Asp Glu
                340                 345                 350
Asn Gly Asn Glu Val Pro Glu Gly Ile Leu Asp Gly Val Leu Thr Ser
                355                 360                 365
Leu Ile Ala Thr His Asn Phe Lys Glu Asn Ala Glu Phe Lys Asn Ser
            370                 375                 380
Leu His Lys Ser Ile Tyr Ile Val Lys Pro Lys Met His Ser Pro Ala
385                 390                 395                 400
Glu Ala Ala Phe Ala Asn Lys Leu Phe Asp Arg Ile Glu Asp Leu Leu
                405                 410                 415
Gly Val Glu Arg Asn Thr Ile Lys Ile Gly Val Met Asp Glu Glu Arg
                420                 425                 430
Arg Met Ser Leu Asn Leu Lys Ser Ala Ile Asn Glu Val Lys Glu Arg
            435                 440                 445
Ile Ala Phe Ile Asn Thr Gly Phe Leu Asp Arg Thr Gly Asp Glu Ile
450                 455                 460
```

His Thr Ser Met Glu Ala Gly Pro Val Ile Arg Lys Ala Asp Met Lys
465                 470                 475                 480

Thr Ser Glu Trp Leu Ser Ser Tyr Glu Ser Ala Asn Val Ala Val Gly
            485                 490                 495

Ile Gly Ala Gly Leu Pro Gly His Ala Gln Ile Gly Lys Gly Met Trp
        500                 505                 510

Ala Met Pro Asp Leu Met Ala Ala Met Leu Glu Gln Lys Ile Ala His
    515                 520                 525

Pro Lys Ala Gly Ala Ser Thr Ala Trp Val Pro Ser Pro Thr Ala Ala
530                 535                 540

Ile Leu His Ala Leu His Tyr His Glu Val Asn Val Lys Glu Val Gln
545                 550                 555                 560

Ala Gly Ile Asp Ser Ser Ile Asp Tyr Arg Asp Gly Ile Leu Asp Ile
            565                 570                 575

Pro Leu Ala Pro Asn Ala Asp Trp Ser Ala Glu Val Gln Ser Glu
        580                 585                 590

Leu Asp Asn Asn Ala Gln Gly Ile Leu Gly Tyr Val Arg Trp Ile
    595                 600                 605

Asp Gln Gly Val Gly Cys Ser Thr Val Pro Asp Ile Asn Asp Val Gly
610                 615                 620

Leu Met Glu Asp Arg Ala Thr Leu Arg Ile Ser Ser Gln His Ile Ala
625                 630                 635                 640

Asn Trp Leu Arg His Gly Val Cys Thr Lys Glu Gln Val Glu Thr
            645                 650                 655

Leu Glu Arg Met Ala Lys Val Val Asp Gln Gln Asn Ala Asp Glu
        660                 665                 670

Leu Tyr Gln Pro Met Ala Pro Asn Tyr Asp Asp Ser Ile Ala Phe Gln
    675                 680                 685

Ala Ala Ser Asp Leu Ile Phe Lys Gly Ala Glu Gln Pro Ser Gly Tyr
690                 695                 700

Thr Glu Pro Ile Leu His Ala Arg Arg Ile Glu Ala Lys Ala Lys Ala
705                 710                 715                 720

Lys Gln Lys Ala Thr Val Gln Asn
            725

<210> SEQ ID NO 29
<211> LENGTH: 2181
<212> TYPE: DNA
<213> ORGANISM: Artificial Sequence
<220> FEATURE:
<223> OTHER INFORMATION: Codon-adapted nucleotide sequence

<400> SEQUENCE: 29
atggaaaatt atgtaaaagt aggctcatta caagtagcaa gtgaacttta tgaatttatt      60
aactcagagg ctctacctgg aagtgatttg gaaccagaga aattttggag tggatttgaa     120
aaattagttc atgatcttac tcctaaaaat aagcaacttc ttgcccgtag agatgaaata     180
caaagtaaaa taaatacttg gcacagagag aacaatcaat cctttaactt cgaaacttat     240
aagagtttcc tagaagaaat aggatattta gaaacagaag tagaggattt tgatataaaa     300
acagaaggtg tagatgatga aatagctgta caggctggtc cacagcttgt agtacctgta     360
aacaatgcaa gatatgcaat aaatgctgca aatgctagat ggggttcact atatgatgct     420
ttatatggta cagatgctat aagtgaagaa ggcggcgcca cacgtgcagg cggctataat     480
cctgttagag gagaaaaggt aatagatttt gcaagagaat ttttagatca agcagtccct     540

```
cttaatggtt tttcccacaa agaagcaaca agttatttag tagtagatgg aaaacttaca      600
gttaagctga aaaatggaga atctacagga ttaaagaatg aggaaaaatt tgcaggatat      660
cagggtgcac cggaacaacc ttctgcagtt cttttaaaga caatggcct tcactttgaa      720 attcaaatag atagatctca tccaatagga caaactgatg aagcgggagt taagatttg      780 ttacttgaat ctgctgtaac tactataatg gactgtgaag attctgttac tgcagtagat      840
gcagaagaca agttttagt ttatagaaat tggcttggat taatgaaagg ggatttggaa      900
gcatctttct caaagggtaa taaatcaatg atgagaaaat taaatgcaga cagaaaatac      960
tcctctccaa ctggcggcga attaagtttg aagggaagaa gtttgttatt tgtaagaaat     1020
gttggccatc ttatgtctat aaatgcaata cttgatcaag acggtgaaga aatacaggaa     1080
ggtattttag acactgttat gacatcgctt atagctaaac atacattact tggaaacggt     1140
tcataccaaa atacttcaaa gggttctgtt tatatagtta aacctaagat gcatggttct     1200
gaagaagtag catttgcaaa tgaattattt gatagagtag aagatttact tgaattacag     1260
agaaatacat tgaaaatagg agtaatggat gaagaaagaa ggacatctct aaacttaaaa     1320
gcatgtatta gacaagttaa agatcgtatt gtatttataa atacaggatt ccttgacagg     1380
acaggtgatg agattcatac aagtatggaa gcaggacctg tagtaagaaa aaatgaaatg     1440
aaatcttcaa aatggcttca agcctatgaa caaagtaatg ttattgctgg attatcatca     1500
ggatttcaag acaggcaca aataggaaaa ggaatgtggg ctatgccaga tttaatgaaa     1560
gagatgatgg aacagaagat aggacatcta aaaactggtg ctaatactgc ctgggttcca     1620
agccctacag cggctacatt gcatgcactt cattatcatc aagttgacat tacaaaagtt     1680
caagatgaac gtgccaacga taaaagagat ttaagagatg atattttaga atttccagta     1740
gtaactaatc cacagtggac gcccgaagaa atacagaatg aattagataa taatgcacaa     1800
tccatacttg gatacgttgt tagatgggtt gaacagggag ttggttgttc aaaagtacct     1860
gacataaaca atgttggatt aatggaagac agggctacat taagaataag cagtcagcat     1920
gtagctaatt ggcttcatca tggaatatgt aagaaggaac aagttattga aacacttcaa     1980
aggatggcaa aggttgtaga tgaacaaaat gctggaaatt tggcttatag gcctatggca     2040
gcaaattatg atgactcagt agcatttcag gctgcctgtg atttaatttt acaaggatat     2100
gatcagccat ctggatacac agagcctata ctacacagaa ggcgtataga ggctaaggct     2160
aaatttgcaa ttaaacaata a                                               2181
```

<210> SEQ ID NO 30
<211> LENGTH: 726
<212> TYPE: PRT
<213> ORGANISM: Bacillus sp. cl95

<400> SEQUENCE: 30

Met Glu Asn Tyr Val Lys Val Gly Ser Leu Gln Val Ala Ser Glu Leu
1               5                   10                  15

Tyr Glu Phe Ile Asn Ser Glu Ala Leu Pro Gly Ser Asp Leu Glu Pro
            20                  25                  30

Glu Lys Phe Trp Ser Gly Phe Glu Lys Leu Val His Asp Leu Thr Pro
        35                  40                  45

Lys Asn Lys Gln Leu Leu Ala Arg Arg Asp Glu Ile Gln Ser Lys Ile
    50                  55                  60

Asn Thr Trp His Arg Glu Asn Asn Gln Ser Phe Asn Phe Glu Thr Tyr
65                  70                  75                  80

Lys Ser Phe Leu Glu Glu Ile Gly Tyr Leu Glu Thr Glu Val Glu Asp
                85                  90                  95
Phe Asp Ile Lys Thr Glu Gly Val Asp Asp Glu Ile Ala Val Gln Ala
            100                 105                 110
Gly Pro Gln Leu Val Val Pro Val Asn Asn Ala Arg Tyr Ala Ile Asn
        115                 120                 125
Ala Ala Asn Ala Arg Trp Gly Ser Leu Tyr Asp Ala Leu Tyr Gly Thr
    130                 135                 140
Asp Ala Ile Ser Glu Glu Gly Ala Thr Arg Ala Gly Gly Tyr Asn
145                 150                 155                 160
Pro Val Arg Gly Glu Lys Val Ile Asp Phe Ala Arg Glu Phe Leu Asp
                165                 170                 175
Gln Ala Val Pro Leu Asn Gly Phe Ser His Lys Glu Ala Thr Ser Tyr
            180                 185                 190
Leu Val Val Asp Gly Lys Leu Thr Val Lys Leu Lys Asn Gly Glu Ser
        195                 200                 205
Thr Gly Leu Lys Asn Glu Glu Lys Phe Ala Gly Tyr Gln Gly Ala Pro
    210                 215                 220
Glu Gln Pro Ser Ala Val Leu Leu Lys Asn Asn Gly Leu His Phe Glu
225                 230                 235                 240
Ile Gln Ile Asp Arg Ser His Pro Ile Gly Gln Thr Asp Glu Ala Gly
                245                 250                 255
Val Lys Asp Leu Leu Leu Glu Ser Ala Val Thr Thr Ile Met Asp Cys
            260                 265                 270
Glu Asp Ser Val Thr Ala Val Asp Ala Glu Asp Lys Val Leu Val Tyr
        275                 280                 285
Arg Asn Trp Leu Gly Leu Met Lys Gly Asp Leu Glu Ala Ser Phe Ser
    290                 295                 300
Lys Gly Asn Lys Ser Met Met Arg Lys Leu Asn Ala Asp Arg Lys Tyr
305                 310                 315                 320
Ser Ser Pro Thr Gly Gly Glu Leu Ser Leu Lys Gly Arg Ser Leu Leu
                325                 330                 335
Phe Val Arg Asn Val Gly His Leu Met Ser Ile Asn Ala Ile Leu Asp
            340                 345                 350
Gln Asp Gly Glu Glu Ile Gln Glu Gly Ile Leu Asp Thr Val Met Thr
        355                 360                 365
Ser Leu Ile Ala Lys His Thr Leu Leu Gly Asn Gly Ser Tyr Gln Asn
    370                 375                 380
Thr Ser Lys Gly Ser Val Tyr Ile Val Lys Pro Lys Met His Gly Ser
385                 390                 395                 400
Glu Glu Val Ala Phe Ala Asn Glu Leu Phe Asp Arg Val Glu Asp Leu
                405                 410                 415
Leu Glu Leu Gln Arg Asn Thr Leu Lys Ile Gly Val Met Asp Glu Glu
            420                 425                 430
Arg Arg Thr Ser Leu Asn Leu Lys Ala Cys Ile Arg Gln Val Lys Asp
        435                 440                 445
Arg Ile Val Phe Ile Asn Thr Gly Phe Leu Asp Arg Thr Gly Asp Glu
    450                 455                 460
Ile His Thr Ser Met Glu Ala Gly Pro Val Val Arg Lys Asn Glu Met
465                 470                 475                 480
Lys Ser Ser Lys Trp Leu Gln Ala Tyr Glu Gln Ser Asn Val Ile Ala
                485                 490                 495

-continued

```
Gly Leu Ser Ser Gly Phe Gln Gly Gln Ala Gln Ile Gly Lys Gly Met
            500                 505                 510
Trp Ala Met Pro Asp Leu Met Lys Glu Met Met Glu Gln Lys Ile Gly
        515                 520                 525
His Leu Lys Thr Gly Ala Asn Thr Ala Trp Val Pro Ser Pro Thr Ala
    530                 535                 540
Ala Thr Leu His Ala Leu His Tyr His Gln Val Asp Ile Thr Lys Val
545                 550                 555                 560
Gln Asp Glu Arg Ala Asn Asp Lys Arg Asp Leu Arg Asp Asp Ile Leu
                565                 570                 575
Glu Phe Pro Val Val Thr Asn Pro Gln Trp Thr Pro Glu Glu Ile Gln
            580                 585                 590
Asn Glu Leu Asp Asn Asn Ala Gln Ser Ile Leu Gly Tyr Val Val Arg
        595                 600                 605
Trp Val Glu Gln Gly Val Gly Cys Ser Lys Val Pro Asp Ile Asn Asn
    610                 615                 620
Val Gly Leu Met Glu Asp Arg Ala Thr Leu Arg Ile Ser Ser Gln His
625                 630                 635                 640
Val Ala Asn Trp Leu His His Gly Ile Cys Lys Lys Glu Gln Val Ile
                645                 650                 655
Glu Thr Leu Gln Arg Met Ala Lys Val Val Asp Glu Gln Asn Ala Gly
            660                 665                 670
Asn Leu Ala Tyr Arg Pro Met Ala Asn Tyr Asp Asp Ser Val Ala
        675                 680                 685
Phe Gln Ala Ala Cys Asp Leu Ile Leu Gln Gly Tyr Asp Gln Pro Ser
    690                 695                 700
Gly Tyr Thr Glu Pro Ile Leu His Arg Arg Ile Glu Ala Lys Ala
705                 710                 715                 720
Lys Phe Ala Ile Lys Gln
                725
```

<210> SEQ ID NO 31
<211> LENGTH: 1623
<212> TYPE: DNA
<213> ORGANISM: Artificial Sequence
<220> FEATURE:
<223> OTHER INFORMATION: Codon-adapted nucleotide sequence

<400> SEQUENCE: 31

```
atgtcagcac cagcaccatc aactttagct atagtagatg cagaaccatt accaagacaa      60
gaggaagtgc ttacagatgc tgcacttgct tttgttgctg aattgcacag aagatttaca     120
ccacgtagag atgaattatt agcaagaagg gcagaaagaa gagcggaaat agctagaact     180
tctacactgg atttcttgcc agaaacagca gctatacgtg ctgatgacag ctggaaggta     240
gcccctgctc cagctgctct caacgacaga agagtagaaa taacaggacc tacagataga     300
aagatgacta taaacgctct aaatagtggt gctaaagttt ggctagcaga ttttgaagat     360
gcttcagctc caacttggga aaatgttgtt ttgggacaat aaatcttgc atcagcttat      420
actagatcca ttgactttac agatgagaga actggaaaga gttatgcact tcgtccggat     480
gctgaattag caacggtagt tatgaggcct agaggttggc atcttgatga agacatctt      540
cagggtagacg gtaggcctgt acctggtgca ttagtggact tgggctttta tttttttcat   600
aatgcacaaa gattgcttga tctaggtaag ggaccatact ctatttacc taaaactgaa     660
tctcatcttg aagcaagact atggaatgaa gtatttgtat ttgcacagga ttatgtaggt     720
```

```
ataccacagg gaactgtcag agcaactgta cttatagaaa ctattacagc agcctatgaa    780
atggaagaaa tactttacga gcttagggac catgcaagtg gcttaaatgc aggaagatgg    840
gattatctat tttccatagt taaaaatttt agggacggcg gcgctaaatt tgttttacct    900
gatagaaatg cagttactat gactgctcca tttatgcgtg cttatacaga attattagta    960
cgtacctgtc acaagagagg agcacatgct ataggcggca tggcagcatt tatacctagt   1020
agaagggatg cagaggtaaa taagtagca tttgaaaaag taagagcaga taaggaccgt    1080
gaggctggtg atggttttga tggcagctgg gttgctcatc cggatcttgt acctatagca   1140
atggagagtt ttgataaggt acttggagat aaaccaaacc aaaaggacag gcttagagaa   1200
gatgtagatg taaaagcagc tgatttaatt gccgtagatt cacttgaggc taaacctacc   1260
tatgcaggat tagttaatgc agttcaagta ggtattagat atattgaagc atggcttaga   1320
ggattaggtg ctgtagctat atttaactta atggaagatg ctgctactgc agaaatatca   1380
aggagtcaga tttggcaatg gattaatgct gaggtagttc ttgataatgg tgaacaggta   1440
acagctgatt tagcccgtaa agtagctgca gaagaattgg caggaataag agcagaaata   1500
ggtgaagagg catttgcagc gggcaactgg caacaggctc atgatttgtt acttactgta   1560
tctttagatg aagattatgc agattttttg actttaccag cttatgaaca acttaaagga   1620
taa                                                                  1623
```

<210> SEQ ID NO 32
<211> LENGTH: 540
<212> TYPE: PRT
<213> ORGANISM: Streptomyces coelicolor

<400> SEQUENCE: 32

```
Met Ser Ala Pro Ala Pro Ser Thr Leu Ala Ile Val Asp Ala Glu Pro
1               5                   10                  15

Leu Pro Arg Gln Glu Glu Val Leu Thr Asp Ala Ala Leu Ala Phe Val
            20                  25                  30

Ala Glu Leu His Arg Arg Phe Thr Pro Arg Arg Asp Glu Leu Leu Ala
        35                  40                  45

Arg Arg Ala Glu Arg Arg Ala Glu Ile Ala Arg Thr Ser Thr Leu Asp
    50                  55                  60

Phe Leu Pro Glu Thr Ala Ala Ile Arg Ala Asp Asp Ser Trp Lys Val
65                  70                  75                  80

Ala Pro Ala Pro Ala Ala Leu Asn Asp Arg Arg Val Glu Ile Thr Gly
                85                  90                  95

Pro Thr Asp Arg Lys Met Thr Ile Asn Ala Leu Asn Ser Gly Ala Lys
            100                 105                 110

Val Trp Leu Ala Asp Phe Glu Asp Ala Ser Ala Pro Thr Trp Glu Asn
        115                 120                 125

Val Val Leu Gly Gln Leu Asn Leu Ala Ser Ala Tyr Thr Arg Ser Ile
    130                 135                 140

Asp Phe Thr Asp Glu Arg Thr Gly Lys Ser Tyr Ala Leu Arg Pro Asp
145                 150                 155                 160

Ala Glu Leu Ala Thr Val Val Met Arg Pro Arg Gly Trp His Leu Asp
                165                 170                 175

Glu Arg His Leu Gln Val Asp Gly Arg Pro Val Pro Gly Ala Leu Val
            180                 185                 190

Asp Phe Gly Leu Tyr Phe Phe His Asn Ala Gln Arg Leu Leu Asp Leu
        195                 200                 205
```

Gly Lys Gly Pro Tyr Phe Tyr Leu Pro Lys Thr Glu Ser His Leu Glu
210                 215                 220

Ala Arg Leu Trp Asn Glu Val Phe Val Phe Ala Gln Asp Tyr Val Gly
225                 230                 235                 240

Ile Pro Gln Gly Thr Val Arg Ala Thr Val Leu Ile Glu Thr Ile Thr
            245                 250                 255

Ala Ala Tyr Glu Met Glu Glu Ile Leu Tyr Glu Leu Arg Asp His Ala
            260                 265                 270

Ser Gly Leu Asn Ala Gly Arg Trp Asp Tyr Leu Phe Ser Ile Val Lys
        275                 280                 285

Asn Phe Arg Asp Gly Gly Ala Lys Phe Val Leu Pro Asp Arg Asn Ala
290                 295                 300

Val Thr Met Thr Ala Pro Phe Met Arg Ala Tyr Thr Glu Leu Leu Val
305                 310                 315                 320

Arg Thr Cys His Lys Arg Gly Ala His Ala Ile Gly Met Ala Ala
                325                 330                 335

Phe Ile Pro Ser Arg Arg Asp Ala Glu Val Asn Lys Val Ala Phe Glu
                340                 345                 350

Lys Val Arg Ala Asp Lys Asp Arg Glu Ala Gly Asp Gly Phe Asp Gly
        355                 360                 365

Ser Trp Val Ala His Pro Asp Leu Val Pro Ile Ala Met Glu Ser Phe
370                 375                 380

Asp Lys Val Leu Gly Asp Lys Pro Asn Gln Lys Asp Arg Leu Arg Glu
385                 390                 395                 400

Asp Val Asp Val Lys Ala Ala Asp Leu Ile Ala Val Asp Ser Leu Glu
                405                 410                 415

Ala Lys Pro Thr Tyr Ala Gly Leu Val Asn Ala Val Gln Val Gly Ile
        420                 425                 430

Arg Tyr Ile Glu Ala Trp Leu Arg Gly Leu Gly Ala Val Ala Ile Phe
        435                 440                 445

Asn Leu Met Glu Asp Ala Ala Thr Ala Glu Ile Ser Arg Ser Gln Ile
    450                 455                 460

Trp Gln Trp Ile Asn Ala Glu Val Val Leu Asp Asn Gly Glu Gln Val
465                 470                 475                 480

Thr Ala Asp Leu Ala Arg Lys Val Ala Ala Glu Glu Leu Ala Gly Ile
                485                 490                 495

Arg Ala Glu Ile Gly Glu Glu Ala Phe Ala Ala Gly Asn Trp Gln Gln
            500                 505                 510

Ala His Asp Leu Leu Leu Thr Val Ser Leu Asp Glu Asp Tyr Ala Asp
        515                 520                 525

Phe Leu Thr Leu Pro Ala Tyr Glu Gln Leu Lys Gly
530                 535                 540

<210> SEQ ID NO 33
<211> LENGTH: 2190
<212> TYPE: DNA
<213> ORGANISM: Artificial Sequence
<220> FEATURE:
<223> OTHER INFORMATION: Codon-adapted nucleotide sequence

<400> SEQUENCE: 33
atgaccaatt atgaaaaagt aggtaagtta caggtagcaa ctgaattagt aaattttgta      60
aatgaggaag tattacctgg cttagaaata cagaaagatc aattctggac caatttcgat     120
tcactgatcc atgaattagc tccagaaaat aaagcacttt tagaaaaaag atcagaactt     180

```
cagaatgcaa tttctgaatg gcatcagcaa aataaaggac aaatagatgc tgcaaaatat      240
aaggaatttc tggaagaaat aggatattta gagccagttg ctgaagattt tcaggtaact      300
acaagcaatg tagataatga aattgctaat caggctggtt ctcaattagt tgtaccaatt      360
gataatgcaa gatatgcttt aaatgcagct aatgctagat ggggttcact atatgatgca      420
ttatatggaa cagatgttat atctgatgaa gatggagcac aggcaggagc agagtataat      480
cctaaaagag gacaaaaagt tattgctttt gctaagaatt tacttgatca ggctgctcct      540
ttagctgagg gatctcatgc agatgcagct gcttataaaa ttgcagatgg aacattacag      600
gttactttag aaaatggaaa aacaactgca cttcaggatg aaagcaagct ggcaggatat      660
aacggaagtg aagatgcccc agaagcagtg ttactagtaa ataatggact tcatattgaa      720
attgcaatag atagaaatca tcctataggt aaagatgata aggctggtgt aaaagaccta      780
gtgcttgaag cagctttatc tacattaatg gattgtgaag atagtatagc agcagtagat      840
gcagaagaca aagtaggtgt ttatagaaat tggttagggc ttatgaaagg agatttagag      900
gcttcattta agagaggaaa taagacagta actagaagaa tgaatgcaga tagaaaatat      960
aaaactgcag atggtaaaga atttacattg cacggaaggt cattgatgtt tgtaagaaat     1020
gtaggacatc ttatgacaaa taatgcaatc ctagatgaaa acggaaatga agttccagaa     1080
ggtatacttg atggagttat aacatcttta attgcaactc ataacttcaa atcagataca     1140
gaatttaaga attcaagaca cggatcaatt tatatagtta agcctaaaat gcatagtcca     1200
gcagaggctg cttttgcaaa taaattattc gatagaatag aggatttatt agggttagag     1260
agaaatacta taaaaatagg attgatggac gaggaacgta gaatgtcctt aaatcttaaa     1320
tctgctataa atgaagttaa agaacgtatt gcttttatta atactggatt ccttgataga     1380
acaggagatg aaatacacac tagcatggaa gcaggacctg taataagaaa agcagacatg     1440
aaggcttcaa actggttaag ttcctatgaa gcaagcaatg ttgcagtagg tataaaagca     1500
ggattaccgg gacatgcaca aataggtaaa ggaatgtggg caatgccaga tatgatggca     1560
gcaatgttag aacagaaggt agctcatcca aaagcaggag catccactgc atgggtacca     1620
tcaccaactg cagctaccct tcatgcacta cattatcatg aagtaaatgt aaaagatgtt     1680
caggctggaa tagattcctc tgtagattat agggatggaa tattagagat accttttggca    1740 ccgtcggtag attggacacc agaagaagtt caatctgaat tagataataa tgcccaagga    1800
atattaggat atgtagtaag atggatagat caaggtgtag gatgttctaa ggtaccagat    1860
ataaatgatg tgggccttat ggaagacagg gcaacattac gaatatctag tcagcatata    1920
gcaaattggc ttagacacgg aatatgtaca aaagaacaag ttcaagaaac attagaaaga    1980
atggctaaag ttgtagatgg tcaaaatgca gatgacgaat tgtaccaacc tatggcacca    2040
aattatgatg attctatagc attccaggct gcttgtgact aatattcaa aggagcagaa     2100 cagccaagtg gatatactga accaattcta catgctagaa gaatagaggc taaggctaaa    2160
gccaagcaaa aagcaactgt acagaattag                                      2190
```

<210> SEQ ID NO 34
<211> LENGTH: 729
<212> TYPE: PRT
<213> ORGANISM: Sporosarcina sp. P35

<400> SEQUENCE: 34

```
Met Thr Asn Tyr Glu Lys Val Gly Lys Leu Gln Val Ala Thr Glu Leu
1               5                   10                  15
```

Val Asn Phe Val Asn Glu Val Leu Pro Gly Leu Glu Ile Gln Lys
            20                  25                  30

Asp Gln Phe Trp Thr Asn Phe Asp Ser Leu Ile His Glu Leu Ala Pro
        35                  40                  45

Glu Asn Lys Ala Leu Leu Glu Lys Arg Ser Glu Leu Gln Asn Ala Ile
    50                  55                  60

Ser Glu Trp His Gln Gln Asn Lys Gly Gln Ile Asp Ala Ala Lys Tyr
65                  70                  75                  80

Lys Glu Phe Leu Glu Glu Ile Gly Tyr Leu Pro Val Ala Glu Asp
                85                  90                  95

Phe Gln Val Thr Thr Ser Asn Val Asp Asn Glu Ile Ala Asn Gln Ala
            100                 105                 110

Gly Ser Gln Leu Val Val Pro Ile Asp Asn Ala Arg Tyr Ala Leu Asn
        115                 120                 125

Ala Ala Asn Ala Arg Trp Gly Ser Leu Tyr Asp Ala Leu Tyr Gly Thr
    130                 135                 140

Asp Val Ile Ser Asp Glu Asp Gly Ala Gln Ala Gly Ala Glu Tyr Asn
145                 150                 155                 160

Pro Lys Arg Gly Gln Lys Val Ile Ala Phe Ala Lys Asn Leu Leu Asp
                165                 170                 175

Gln Ala Ala Pro Leu Ala Glu Gly Ser His Ala Asp Ala Ala Ala Tyr
            180                 185                 190

Lys Ile Ala Asp Gly Thr Leu Gln Val Thr Leu Glu Asn Gly Lys Thr
        195                 200                 205

Thr Ala Leu Gln Asp Glu Ser Lys Leu Ala Gly Tyr Asn Gly Ser Glu
    210                 215                 220

Asp Ala Pro Glu Ala Val Leu Val Asn Asn Gly Leu His Ile Glu
225                 230                 235                 240

Ile Ala Ile Asp Arg Asn His Pro Ile Gly Lys Asp Lys Ala Gly
                245                 250                 255

Val Lys Asp Leu Val Leu Glu Ala Ala Leu Ser Thr Leu Met Asp Cys
            260                 265                 270

Glu Asp Ser Ile Ala Ala Val Asp Ala Glu Asp Lys Val Gly Val Tyr
        275                 280                 285

Arg Asn Trp Leu Gly Leu Met Lys Gly Asp Leu Glu Ala Ser Phe Lys
    290                 295                 300

Arg Gly Asn Lys Thr Val Thr Arg Arg Met Asn Ala Asp Arg Lys Tyr
305                 310                 315                 320

Lys Thr Ala Asp Gly Lys Glu Phe Thr Leu His Gly Arg Ser Leu Met
                325                 330                 335

Phe Val Arg Asn Val Gly His Leu Met Thr Asn Asn Ala Ile Leu Asp
            340                 345                 350

Glu Asn Gly Asn Glu Val Pro Glu Gly Ile Leu Asp Gly Val Ile Thr
        355                 360                 365

Ser Leu Ile Ala Thr His Asn Phe Lys Ser Asp Thr Glu Phe Lys Asn
    370                 375                 380

Ser Arg His Gly Ser Ile Tyr Ile Val Lys Pro Lys Met His Ser Pro
385                 390                 395                 400

Ala Glu Ala Ala Phe Ala Asn Lys Leu Phe Asp Arg Ile Glu Asp Leu
                405                 410                 415

Leu Gly Leu Glu Arg Asn Thr Ile Lys Ile Gly Leu Met Asp Glu Glu
            420                 425                 430

Arg Arg Met Ser Leu Asn Leu Lys Ser Ala Ile Asn Glu Val Lys Glu

```
             435                 440                 445
Arg Ile Ala Phe Ile Asn Thr Gly Phe Leu Asp Arg Thr Gly Asp Glu
        450                 455                 460

Ile His Thr Ser Met Glu Ala Gly Pro Val Ile Arg Lys Ala Asp Met
465                 470                 475                 480

Lys Ala Ser Asn Trp Leu Ser Ser Tyr Glu Ala Ser Asn Val Ala Val
                485                 490                 495

Gly Ile Lys Ala Gly Leu Pro Gly His Ala Gln Ile Gly Lys Gly Met
                500                 505                 510

Trp Ala Met Pro Asp Met Met Ala Ala Met Leu Glu Gln Lys Val Ala
                515                 520                 525

His Pro Lys Ala Gly Ala Ser Thr Ala Trp Val Pro Ser Pro Thr Ala
                530                 535                 540

Ala Thr Leu His Ala Leu His Tyr His Glu Val Asn Val Lys Asp Val
545                 550                 555                 560

Gln Ala Gly Ile Asp Ser Ser Val Asp Tyr Arg Asp Gly Ile Leu Glu
                565                 570                 575

Ile Pro Leu Ala Pro Ser Val Asp Trp Thr Pro Glu Glu Val Gln Ser
                580                 585                 590

Glu Leu Asp Asn Asn Ala Gln Gly Ile Leu Gly Tyr Val Val Arg Trp
                595                 600                 605

Ile Asp Gln Gly Val Gly Cys Ser Lys Val Pro Asp Ile Asn Asp Val
610                 615                 620

Gly Leu Met Glu Asp Arg Ala Thr Leu Arg Ile Ser Ser Gln His Ile
625                 630                 635                 640

Ala Asn Trp Leu Arg His Gly Ile Cys Thr Lys Gln Val Gln Glu
                645                 650                 655

Thr Leu Glu Arg Met Ala Lys Val Val Asp Gly Gln Asn Ala Asp Asp
                660                 665                 670

Glu Leu Tyr Gln Pro Met Ala Pro Asn Tyr Asp Asp Ser Ile Ala Phe
                675                 680                 685

Gln Ala Ala Cys Asp Leu Ile Phe Lys Gly Ala Glu Gln Pro Ser Gly
690                 695                 700

Tyr Thr Glu Pro Ile Leu His Ala Arg Arg Ile Glu Ala Lys Ala Lys
705                 710                 715                 720

Ala Lys Gln Lys Ala Thr Val Gln Asn
                725

<210> SEQ ID NO 35
<211> LENGTH: 2181
<212> TYPE: DNA
<213> ORGANISM: Artificial Sequence
<220> FEATURE:
<223> OTHER INFORMATION: Codon-adapted nucleotide sequence

<400> SEQUENCE: 35
atggtagcgt ataaacaaat aggaaaactt caggtagctc agttttata taattttata      60 aatgaagaag cattacctga acaggactt caggaagaag cgttctgggc gggttttgaa     120
cagttaattc atgaattgac tcctgaaaat aaggctctac ttgctaaaag agatgaatta    180
caagcaaaac taaacagatg gtacagagaa ataggact cattcgattt tgaagcatac      240
aaggcttttt taacatctat tggatatctt gaagcagatg ttgcagattt tcaaatatca    300
actgctaatg tagatgatga aattgcttta caggctggtc ctcaattagt tgtaccagta    360
aataatgcaa gatatgctat aaatgctgca aatgcaagat ggggttcttt gtatgatgcc    420
```

```
ctctacggaa ctgatgcaat atcttctgaa aatggagcag gcgtgcaaag tcaatataat    480
cctattcgag gtgagaaggt aataactttt gctaaaagct ttttaaatca cactattccc    540
ttaaaagaag gaaagcatga agatgtagtt caatacgtgg taacaaataa gatggaagca    600
ttgcttcaag atggaactac tacagagtta aaagaaccat caaaatgggt tggctatcaa    660
ggggatggtt caaatccatc agcacttttta tttaagaata atggacttca ctttgaaata    720
cagatagata gacaggatgc cataggtaaa tcagatgatg ctggtgtaaa agatgtattg    780
ttagagtcag ctgtaacaac tattatggat tgtgaagata gtgtagctgc cgtagatgca    840
gaagataaag ttgaagtata caggaactgg ttgggattaa tgaaaggtga tctgaaggca    900
agatttaaga aaggtgcaaa aactatgaca agaacattga atgatgacag acagtataaa    960
actgcaaatg gagatactgt aacattatca ggtagatcct taatgtttgt tagaaatgta   1020
ggacatttga tgtcaaattc tgctatttta gatgcaaatg gagatgaaat acaggaagga   1080
atacttgatt caataataac ttcacttata gctaaacata ctttattagg aacaggaaaa   1140
taccaaaaca gccaaaaggg aagtgtttat attgtaaaac ctaaaatgca tggttcagaa   1200
gaagtagctt ttgctaataa acttttttgat agagttgaag atcttgtagg actaccaaga   1260
catactttaa aaataggtgt catggatgaa gaaagaagaa cttcattaaa tttaaaagca   1320
tgcatagaga agtaaagaa tagggtagct tttataaaca ctggtttttt ggatagaact   1380
ggagatgaaa tgcataccag tatggaagca ggagttatga taagaaaaaa tgacatgaaa   1440
tcaagtgttt ggttggcagg atacgaaaaa agcaatgtat taaccggatt agcttcaggc   1500
tttcagggaa aagcccagat aggtaaaggc atgtgggcaa tgcctgatct tatggcagaa   1560
atgttaaaac aaaaagtagg acatcttcag gctggagcca atacagcatg ggtaccttca   1620
ccaacagcag ccactttaca tgccttgcac tatcatgaag tatccgtagt tgatgtacag   1680
aatcaacttg ctaacaattc tacaaatttg agggatgata ttttacaggt acctcttgca   1740
aaagagccaa attggacaaa agaggaagtt caacaggaat tggacaacaa tgcgcaaggc   1800
attttaggat acgtggtaag atgggtagac caaggtatag ttgttctaa agtgcctgac   1860 ataaatgatg ttggacttat ggaagatagg gcaactctaa gaatatcatc acaacatgta   1920
gcaaattggc ttcatcacgg aatatgtact aaggaacagg tacttgctac tcttcagaga   1980
atggccaaag tagtggattc tcaaaatgct ggtgatgcta attatcagcc aatggctcct   2040
cactacgagg aatctatagc attccaggca gcctgtgatt tagtattcaa aggctatgat   2100
cagccaaatg gatatacaga gcctatattg catgcaagaa gaatagaggc taaggcaaaa   2160
caagcaatag aacagaaata a                                              2181
```

<210> SEQ ID NO 36
<211> LENGTH: 726
<212> TYPE: PRT
<213> ORGANISM: Bacillus sp. VT 712

<400> SEQUENCE: 36

```
Met Val Ala Tyr Lys Gln Ile Gly Lys Leu Gln Val Ala Pro Val Leu
1               5                   10                  15

Tyr Asn Phe Ile Asn Glu Glu Ala Leu Pro Glu Thr Gly Leu Gln Glu
            20                  25                  30

Glu Ala Phe Trp Ala Gly Phe Glu Gln Leu Ile His Glu Leu Thr Pro
        35                  40                  45

Glu Asn Lys Ala Leu Leu Ala Lys Arg Asp Glu Leu Gln Ala Lys Leu
```

```
                50                  55                  60
Asn Arg Trp Tyr Arg Glu Asn Arg Asp Ser Phe Asp Phe Glu Ala Tyr
 65                  70                  75                  80

Lys Ala Phe Leu Thr Ser Ile Gly Tyr Leu Glu Ala Asp Val Ala Asp
                 85                  90                  95

Phe Gln Ile Ser Thr Ala Asn Val Asp Asp Glu Ile Ala Leu Gln Ala
                100                 105                 110

Gly Pro Gln Leu Val Val Pro Val Asn Asn Ala Arg Tyr Ala Ile Asn
                115                 120                 125

Ala Ala Asn Ala Arg Trp Gly Ser Leu Tyr Asp Ala Leu Tyr Gly Thr
130                 135                 140

Asp Ala Ile Ser Ser Glu Asn Gly Ala Gly Val Gln Ser Gln Tyr Asn
145                 150                 155                 160

Pro Ile Arg Gly Glu Lys Val Ile Thr Phe Ala Lys Ser Phe Leu Asn
                165                 170                 175

His Thr Ile Pro Leu Lys Glu Gly Lys His Glu Asp Val Val Gln Tyr
                180                 185                 190

Val Val Thr Asn Lys Met Glu Ala Leu Leu Gln Asp Gly Thr Thr Thr
                195                 200                 205

Glu Leu Lys Glu Pro Ser Lys Trp Val Gly Tyr Gln Gly Asp Gly Ser
210                 215                 220

Asn Pro Ser Ala Leu Leu Phe Lys Asn Gly Leu His Phe Glu Ile
225                 230                 235                 240

Gln Ile Asp Arg Gln Asp Ala Ile Gly Lys Ser Asp Ala Gly Val
                245                 250                 255

Lys Asp Val Leu Leu Glu Ser Ala Val Thr Thr Ile Met Asp Cys Glu
                260                 265                 270

Asp Ser Val Ala Ala Val Asp Ala Glu Asp Lys Val Glu Val Tyr Arg
                275                 280                 285

Asn Trp Leu Gly Leu Met Lys Gly Asp Leu Lys Ala Arg Phe Lys Lys
                290                 295                 300

Gly Ala Lys Thr Met Thr Arg Thr Leu Asn Asp Asp Arg Gln Tyr Lys
305                 310                 315                 320

Thr Ala Asn Gly Asp Thr Val Thr Leu Ser Gly Arg Ser Leu Met Phe
                325                 330                 335

Val Arg Asn Val Gly His Leu Met Ser Asn Ser Ala Ile Leu Asp Ala
                340                 345                 350

Asn Gly Asp Glu Ile Gln Glu Gly Ile Leu Asp Ser Ile Ile Thr Ser
                355                 360                 365

Leu Ile Ala Lys His Thr Leu Leu Gly Thr Gly Lys Tyr Gln Asn Ser
370                 375                 380

Gln Lys Gly Ser Val Tyr Ile Val Lys Pro Lys Met His Gly Ser Glu
385                 390                 395                 400

Glu Val Ala Phe Ala Asn Lys Leu Phe Asp Arg Val Glu Asp Leu Val
                405                 410                 415

Gly Leu Pro Arg His Thr Leu Lys Ile Gly Val Met Asp Glu Glu Arg
                420                 425                 430

Arg Thr Ser Leu Asn Leu Lys Ala Cys Ile Glu Lys Val Lys Asn Arg
                435                 440                 445

Val Ala Phe Ile Asn Thr Gly Phe Leu Asp Arg Thr Gly Asp Glu Met
                450                 455                 460

His Thr Ser Met Glu Ala Gly Val Met Ile Arg Lys Asn Asp Met Lys
465                 470                 475                 480
```

```
Ser Ser Val Trp Leu Ala Gly Tyr Glu Lys Ser Asn Val Leu Thr Gly
            485                 490                 495

Leu Ala Ser Gly Phe Gln Gly Lys Ala Gln Ile Gly Lys Gly Met Trp
            500                 505                 510

Ala Met Pro Asp Leu Met Ala Glu Met Leu Lys Gln Lys Val Gly His
            515                 520                 525

Leu Gln Ala Gly Ala Asn Thr Ala Trp Val Pro Ser Pro Thr Ala Ala
            530                 535                 540

Thr Leu His Ala Leu His Tyr His Glu Val Ser Val Asp Val Gln
545                 550                 555                 560

Asn Gln Leu Ala Asn Asn Ser Thr Asn Leu Arg Asp Asp Ile Leu Gln
            565                 570                 575

Val Pro Leu Ala Lys Glu Pro Asn Trp Thr Lys Glu Val Gln Gln
            580                 585                 590

Glu Leu Asp Asn Asn Ala Gln Gly Ile Leu Gly Tyr Val Val Arg Trp
            595                 600                 605

Val Asp Gln Gly Ile Gly Cys Ser Lys Val Pro Asp Ile Asn Asp Val
            610                 615                 620

Gly Leu Met Glu Asp Arg Ala Thr Leu Arg Ile Ser Ser Gln His Val
625                 630                 635                 640

Ala Asn Trp Leu His His Gly Ile Cys Thr Lys Glu Gln Val Leu Ala
            645                 650                 655

Thr Leu Gln Arg Met Ala Lys Val Val Asp Ser Gln Asn Ala Gly Asp
            660                 665                 670

Ala Asn Tyr Gln Pro Met Ala Pro His Tyr Glu Glu Ser Ile Ala Phe
            675                 680                 685

Gln Ala Ala Cys Asp Leu Val Phe Lys Gly Tyr Asp Gln Pro Asn Gly
            690                 695                 700

Tyr Thr Glu Pro Ile Leu His Ala Arg Arg Ile Glu Ala Lys Ala Lys
705                 710                 715                 720

Gln Ala Ile Glu Gln Lys
            725

<210> SEQ ID NO 37
<211> LENGTH: 2181
<212> TYPE: DNA
<213> ORGANISM: Artificial Sequence
<220> FEATURE:
<223> OTHER INFORMATION: Codon-adapted nucleotide sequence

<400> SEQUENCE: 37
atggcaaact atagaaaaat aggaaattta caggtagacg aggcacttca tcaatttctt      60 caaaagagg ctttaccagg tacaggactt gaagaaaagg cttttttgaa tggatttgag     120
aaacttatag aagtattaac tccagaaaat aaaagacttc ttgcaaagag agaagagctt     180
caaagagaac ttgatagata tcactcagag aaaagagatg atttttcatt tgaagcatac     240
aagcaatttt tacttgattt aggatatctt ttacctgaac tggagagtt caaaataagg      300 acagaaaatg tagatgatga gattgctctt caagcaggac cacaattggt cgttcctgtc     360
aataattcaa gatattcaat aaacgcagca atgctcgct ggggtagctt atatgatgcc     420
ttgtatggaa cagatgctat aagcgaagaa ggcggcgctg agagatctat agagtacaat     480
agagttagag gaaataaagt tatagaattt gcaaagggat tcttagatca ggcagctgca     540
cttgacggtg catcccacaa agaagcagtt agatattccg caaaggaagg ttctttagtt     600
```

```
ataactttga aagatggaag ttcctctaaa ttaaaagatc aagaggcttt tgctgggtat    660
agaggagata aagaccatcc agaggctgta ttacttaaac atcatggatt gcattttgaa    720
atacagatag atagggcaag tgacatcgga aagtcagatc ctgctggtat taaagatata    780
ttattggaag cagcagtaac tgttataatg gattgtgaag attctgtagc tgctgtagat    840
gctgaagata aggtacttgt atatagaaat tggcttggat tgatgaaagg agaactttcc    900
gcagatttta gcaagggcgg caaaataata tcaagaaaat taaatggtgt acgtcattat    960
agagatcctg aaggaaatct tttttcattg cctggaagat cattactttt cgtaagaaat   1020
gtaggtcatc ttatgactaa cccagctgtt ttggataaag aaggaaatga agtttatgaa   1080
ggtattctag atgcagtatt cacatcttta gctggaatgc acagcttatt aaatactgaa   1140
gagcccgcaa actcaagaaa aggatctata tatatagtta agccaaaaat gcacgggcca   1200
gaagaagttg cttatgcagg agaactattt gataaaactg aagatctttt aggacttgac   1260
agaaacactc ttaaaattgg attaatggat gaagaaagga gaacttcatt aaatttaaag   1320
tcttgtataa aagaagtaaa agatcgtatt gtatttataa atacaggttt tttagataga   1380
acaggtgatg aaatacattc atctatggaa gcaggaccta tggtgagaaa gggagaaatg   1440
aaaaaatcaa actggcttca ggcttatgaa acttcaaatg tttccacggg tctttcagca   1500
ggattttctg gtaaggcaca gatcggaaag ggtatgtggg caatgccaga taaaatgaaa   1560
gaaatgctgg aacagaaagg tgcccagttg aaaactggtg ctaatacagc atgggttcca   1620
tctccatctg cagcagtact tcatgcccta cattatcatc aaataaatgt taaaggtata   1680
caagagaaag aatgccaaaa tccgtctctt tatcgtgacg aaatgctgtc aataccagtt   1740
gaaacctgtg gttcttggtc aagtgaagaa attcaagttg aaatagaaaa taatgcacaa   1800
ggtatattgg gatacgtagt tagatgggta gaacagggta taggatgctc taaagtccct   1860
gatattcatg atgtaggcct catggaagat agagcaactt taagaataag tagtcagcat   1920
cttgctaatt ggatacatca caagatagtt tcaagagaac aggtaatgaa tgctttaaaa   1980
aagatggcta aaattgtaga tgcacaaaat gaaaatgaac cgggctataa aagaatgagc   2040
gatgacttct ctacatctgt tgcattccag gctgcctgtg aattaatatt tgaaggcaga   2100
aatcaaccta atggatatac ggaacctatt ctccacaaga gaagattaga ggctaaatcc   2160
aaaatggcag taagacaata a                                             2181
```

<210> SEQ ID NO 38
<211> LENGTH: 726
<212> TYPE: PRT
<213> ORGANISM: Bacillus infantis NRRL B-14911

<400> SEQUENCE: 38

```
Met Ala Asn Tyr Arg Lys Ile Gly Asn Leu Gln Val Asp Glu Ala Leu
1               5                   10                  15

His Gln Phe Leu Gln Lys Glu Ala Leu Pro Gly Thr Gly Leu Glu Glu
            20                  25                  30

Lys Ala Phe Trp Asn Gly Phe Glu Lys Leu Ile Glu Val Leu Thr Pro
        35                  40                  45

Glu Asn Lys Arg Leu Leu Ala Lys Arg Glu Glu Leu Gln Arg Glu Leu
    50                  55                  60

Asp Arg Tyr His Ser Glu Lys Arg Asp Asp Phe Ser Phe Glu Ala Tyr
65                  70                  75                  80

Lys Gln Phe Leu Leu Asp Leu Gly Tyr Leu Leu Pro Glu Pro Gly Glu
                85                  90                  95
```

```
Phe Lys Ile Arg Thr Glu Asn Val Asp Asp Glu Ile Ala Leu Gln Ala
            100                 105                 110
Gly Pro Gln Leu Val Val Pro Val Asn Asn Ser Arg Tyr Ser Ile Asn
            115                 120                 125
Ala Ala Asn Ala Arg Trp Gly Ser Leu Tyr Asp Ala Leu Tyr Gly Thr
130                 135                 140
Asp Ala Ile Ser Glu Glu Gly Ala Glu Arg Ser Ile Glu Tyr Asn
145                 150                 155                 160
Arg Val Arg Gly Asn Lys Val Ile Glu Phe Ala Lys Gly Phe Leu Asp
                165                 170                 175
Gln Ala Ala Leu Asp Gly Ala Ser His Lys Glu Ala Val Arg Tyr
            180                 185                 190
Ser Ala Lys Glu Gly Ser Leu Val Ile Thr Leu Lys Asp Gly Ser Ser
            195                 200                 205
Ser Lys Leu Lys Asp Gln Glu Ala Phe Ala Gly Tyr Arg Gly Asp Lys
            210                 215                 220
Asp His Pro Glu Ala Val Leu Leu Lys His His Gly Leu His Phe Glu
225                 230                 235                 240
Ile Gln Ile Asp Arg Ala Ser Asp Ile Gly Lys Ser Asp Pro Ala Gly
                245                 250                 255
Ile Lys Asp Ile Leu Leu Glu Ala Ala Val Thr Val Ile Met Asp Cys
            260                 265                 270
Glu Asp Ser Val Ala Ala Val Asp Ala Glu Asp Lys Val Leu Val Tyr
            275                 280                 285
Arg Asn Trp Leu Gly Leu Met Lys Gly Glu Leu Ser Ala Asp Phe Ser
            290                 295                 300
Lys Gly Gly Lys Ile Ile Ser Arg Lys Leu Asn Gly Val Arg His Tyr
305                 310                 315                 320
Arg Asp Pro Glu Gly Asn Leu Phe Ser Leu Pro Gly Arg Ser Leu Leu
                325                 330                 335
Phe Val Arg Asn Val Gly His Leu Met Thr Asn Pro Ala Val Leu Asp
            340                 345                 350
Lys Glu Gly Asn Glu Val Tyr Glu Gly Ile Leu Asp Ala Val Phe Thr
            355                 360                 365
Ser Leu Ala Gly Met His Ser Leu Leu Asn Thr Glu Glu Pro Ala Asn
            370                 375                 380
Ser Arg Lys Gly Ser Ile Tyr Ile Val Lys Pro Lys Met His Gly Pro
385                 390                 395                 400
Glu Glu Val Ala Tyr Ala Gly Glu Leu Phe Asp Lys Thr Glu Asp Leu
                405                 410                 415
Leu Gly Leu Asp Arg Asn Thr Leu Lys Ile Gly Leu Met Asp Glu Glu
            420                 425                 430
Arg Arg Thr Ser Leu Asn Leu Lys Ser Cys Ile Lys Glu Val Lys Asp
            435                 440                 445
Arg Ile Val Phe Ile Asn Thr Gly Phe Leu Asp Arg Thr Gly Asp Glu
            450                 455                 460
Ile His Ser Ser Met Glu Ala Gly Pro Met Val Arg Lys Gly Glu Met
465                 470                 475                 480
Lys Lys Ser Asn Trp Leu Gln Ala Tyr Glu Thr Ser Asn Val Ser Thr
                485                 490                 495
Gly Leu Ser Ala Gly Phe Ser Gly Lys Ala Gln Ile Gly Lys Gly Met
            500                 505                 510
```

Trp Ala Met Pro Asp Lys Met Lys Glu Met Leu Glu Gln Lys Gly Ala
            515                 520                 525

Gln Leu Lys Thr Gly Ala Asn Thr Ala Trp Val Pro Ser Pro Ser Ala
        530                 535                 540

Ala Val Leu His Ala Leu His Tyr His Gln Ile Asn Val Lys Gly Ile
545                 550                 555                 560

Gln Glu Lys Glu Cys Gln Asn Pro Ser Leu Tyr Arg Asp Glu Met Leu
                565                 570                 575

Ser Ile Pro Val Glu Thr Cys Gly Ser Trp Ser Glu Glu Ile Gln
            580                 585                 590

Val Glu Ile Glu Asn Asn Ala Gln Gly Ile Leu Gly Tyr Val Val Arg
            595                 600                 605

Trp Val Glu Gln Gly Ile Gly Cys Ser Lys Val Pro Asp Ile His Asp
        610                 615                 620

Val Gly Leu Met Glu Asp Arg Ala Thr Leu Arg Ile Ser Ser Gln His
625                 630                 635                 640

Leu Ala Asn Trp Ile His His Lys Ile Val Ser Arg Glu Gln Val Met
                645                 650                 655

Asn Ala Leu Lys Lys Met Ala Lys Ile Val Asp Ala Gln Asn Glu Asn
            660                 665                 670

Glu Pro Gly Tyr Lys Arg Met Ser Asp Asp Phe Ser Thr Ser Val Ala
        675                 680                 685

Phe Gln Ala Ala Cys Glu Leu Ile Phe Glu Gly Arg Asn Gln Pro Asn
    690                 695                 700

Gly Tyr Thr Glu Pro Ile Leu His Lys Arg Arg Leu Glu Ala Lys Ser
705                 710                 715                 720

Lys Met Ala Val Arg Gln
                725

<210> SEQ ID NO 39
<211> LENGTH: 855
<212> TYPE: DNA
<213> ORGANISM: Artificial Sequence
<220> FEATURE:
<223> OTHER INFORMATION: Codon-adapted nucleotide sequence

<400> SEQUENCE: 39
atgtatttag tagataaaga agtaattcat gaaacatttg caaaggttc agtagtaaat      60 tataatgata attatattaa gattgacttt gaatcaggcg caaagaaatt tgtatttcct    120
gacgtatttg ggaaatatat gactcttgta gatcaggaag cagtaaactt agttaatatg    180
aaaatacaga aaagagaaga agaaaagaaa aaagaggaac ttaagttaat taagaaaaaa    240
gatcttgaaa gagaaagaca gcatatactg gagcaaaaaa aaactatgca atccaggaaa    300
attcatccaa acaacaggt agtattctgg tgtgaaaccg gagaggaaga taaaatattt    360
actgagggta ggatatttat aggtaaggta aagagtggag aaaataaggg tcagccgaag    420
agattagcaa gaatgacctg gaaatcaggc tgcttactaa caaggcgtga accaggtatg    480
cctgaaaaag acagaaggat attaggagta tttatggctg aagaaggttt caatggtcaa    540
acctgtaagg atggctatat tccagcccat cctgaatata aacttagact tagtgaacaa    600
gaatcagata aaatgttatt ttggaattat tatataaata agaacttccc tactagaatg    660
acttggaatt caggcagaca gagatatttt aacaatattt ggatggcaca aatacttcaa    720
gatattgtaa gcttaaaaaa taaacctgaa gaagggaaa atgcacagag attctttgaa    780
cacttctgta agttaaccca tataaatgaa gataaacttc ctaaggcaaa tggtgccttg    840
atgcaaattc aataa 855

<210> SEQ ID NO 40
<211> LENGTH: 284
<212> TYPE: PRT
<213> ORGANISM: Clostridium cochlearium

<400> SEQUENCE: 40

Met Tyr Leu Val Asp Lys Glu Val Ile His Glu Thr Phe Gly Lys Gly
1 5 10 15

Ser Val Val Asn Tyr Asn Asp Asn Tyr Ile Lys Ile Asp Phe Glu Ser
20 25 30

Gly Ala Lys Lys Phe Val Phe Pro Asp Val Phe Gly Lys Tyr Met Thr
35 40 45

Leu Val Asp Gln Glu Ala Val Asn Leu Val Asn Met Lys Ile Gln Lys
50 55 60

Arg Glu Glu Glu Lys Lys Lys Glu Glu Leu Lys Leu Ile Lys Glu Lys
65 70 75 80

Asp Leu Glu Arg Glu Arg Gln His Ile Leu Glu Gln Lys Lys Thr Met
85 90 95

Gln Ser Arg Lys Ile His Pro Lys Gln Gln Val Val Phe Trp Cys Glu
100 105 110

Thr Gly Glu Glu Asp Lys Ile Phe Thr Glu Gly Arg Ile Phe Ile Gly
115 120 125

Lys Val Lys Ser Gly Glu Asn Lys Gly Gln Pro Lys Arg Leu Ala Arg
130 135 140

Met Thr Trp Lys Ser Gly Cys Leu Leu Thr Arg Arg Glu Pro Gly Met
145 150 155 160

Pro Glu Lys Asp Arg Arg Ile Leu Gly Val Phe Met Ala Glu Glu Gly
165 170 175

Phe Asn Gly Gln Thr Cys Lys Asp Gly Tyr Ile Pro Ala His Pro Glu
180 185 190

Tyr Lys Leu Arg Leu Ser Glu Gln Glu Ser Asp Lys Met Leu Phe Trp
195 200 205

Asn Tyr Tyr Ile Asn Lys Asn Phe Pro Thr Arg Met Thr Trp Asn Ser
210 215 220

Gly Arg Gln Arg Tyr Phe Asn Asn Ile Trp Met Ala Gln Ile Leu Gln
225 230 235 240

Asp Ile Val Ser Leu Lys Asn Lys Pro Glu Glu Arg Glu Asn Ala Gln
245 250 255

Arg Phe Phe Glu His Phe Cys Lys Val Asn His Ile Asn Glu Asp Lys
260 265 270

Leu Pro Lys Ala Asn Gly Ala Leu Met Gln Ile Gln
275 280

<210> SEQ ID NO 41
<211> LENGTH: 2178
<212> TYPE: DNA
<213> ORGANISM: Artificial Sequence
<220> FEATURE:
<223> OTHER INFORMATION: Codon-adapted nucleotide sequence

<400> SEQUENCE: 41
atgactaact ataaacaagt aggcaattta aaagtagcac cagtactata tcaattcata 60
aatgaagaag cattaccggg cagtggactt tccacggaaa acttttggtc tgattttgag 120

```
gctttagtaa ctgagcttac tcctgttaat aaaagactcc ttgaaaaaag ggatcagctt      180
caggcacaaa taaatgcatg gcatcaagaa atccagatg gtgatttctc tgaatacaag       240
agtttcctaa ctcgtattgg atatcttgag gataaaacag aggatttttt aattggaacg     300
gaaggtgttg acagtgaaat tgcttatcag gctggtcctc aattagtggt tccggtgaat     360
aacgcaaggt atgcaataaa tgctgctaat gcaagatggg gaagtttgta tgatgcttta     420
tatggcactg atgctatttc agaagaaaat ggtgcgtcaa gaactagttc ctacaatcct     480
attaggggag aaaaagttat agcttttgca aaaaatttcc ttgatgaagt tgtaccttta     540
gtccagagct ctcatgcaga ggttgttcaa tacagtttgg aaaatgaaaa attagtagca     600
caattaaatg atggtagctt aacagaactt caagaagaag aaaaattcgt tggatatcag     660
ggagaagaag aatcaccaga tgccttgtta ttcaaaaaca atggacttca ttttgaagtt     720
caaatagata gaacagattc cataggaaaa acagacgatg caggagttaa agatatactt     780
atggaagcag cacttacaac tataatggat tgcgaagatt ctgtagctgc tgttgatgca     840
gaagacaagg ttgacgtgta tagaaactgg ttaggtctta tgaaaggaga tttaactagt     900
acatttaaga agggatctca aaatatgaca agaagattaa atccggatag aacttatata     960
agtccagata agaaaaagat attattgtcg ggaagatcac ttatgtttgt aagaaatgtt    1020
ggacatctta tgactaattc tgctgtatta gatagaaatg gtaacgaaat atacgagggt    1080
attttggatt ctgttattac atctttaatt gcaaaacata ccttattaaa gaatggtact    1140
tatcaaaatt ctaagaaatc aagtatatac attgttaaac caaaaatgca tggatcaaaa    1200
gaagttgctt ttgccaacac attatttaac tctatagaag atatgttagg gttagagcgt    1260
catactataa aaattggagt tatggatgag gaaagaagaa caactttaaa tcttaaagcc    1320
tgtataaagg aagtaaagga cagagtagct tttataaata ctggttttct tgacagaact    1380
ggagatgaaa tacacacatc aatggaagcc ggagcagtta taagaaaaaa cgatatgaag    1440
gcttcaaaat ggcttcaagg atatgaacaa tcaaatgtaa atgtaggatt agctagtgga    1500
tttcaaggaa gggcacaaat aggtaaggga atgtgggcta tgccggatat gatggcagaa    1560
atgcttaaac aaaaagtagg tcatcttaaa gcaggagcca atacggcatg ggttcctagt    1620
cctacagcag caacccttca tgccctacat tatcatcaaa ttgatgttag agatgtacaa    1680
aacgagttac ttacacaatc cacagatctt caggatgata tattacaaat tccagttgct    1740
gaaaagccta attggtctaa agatgaaata cagcaagaat tagataataa tgcacaagga    1800
atacttggat atgtagttag atgggtagat cagggtgtag gttgttcaaa agttccagat    1860
ataaataatg taggacttat ggaagatcgg gctacactgc gcatctcaag tcagcatgta    1920
gcaaattggt tgcatcatgg tatttgtact aaagaacaag ttactgaaac attaaaaaga    1980
atggcgaaag ttgtagatca gcaaaatgaa aatgatccat tatatcagcc tatgagttca    2040
aattacagtg catcaatagc atttcaggct gcgtgcgatc ttgtattcca gggatacgac    2100
caacctaatg gatacacaga accaatattg catagaagaa ggattgaagc aaaggctaaa    2160
gcagcaataa aacaataa                                                  2178
```

<210> SEQ ID NO 42
<211> LENGTH: 725
<212> TYPE: PRT
<213> ORGANISM: Bacillus megaterium

<400> SEQUENCE: 42

Met Thr Asn Tyr Lys Gln Val Gly Asn Leu Lys Val Ala Pro Val Leu

-continued

```
1               5                   10                  15
Tyr Gln Phe Ile Asn Glu Glu Ala Leu Pro Gly Ser Gly Leu Ser Thr
                20                  25                  30

Glu Asn Phe Trp Ser Asp Phe Glu Ala Leu Val Thr Glu Leu Thr Pro
                35                  40                  45

Val Asn Lys Arg Leu Leu Glu Lys Arg Asp Gln Leu Gln Ala Gln Ile
                50                  55                  60

Asn Ala Trp His Gln Glu Asn Pro Asp Gly Asp Phe Ser Glu Tyr Lys
65                  70                  75                  80

Ser Phe Leu Thr Arg Ile Gly Tyr Leu Glu Asp Lys Thr Glu Asp Phe
                85                  90                  95

Leu Ile Gly Thr Glu Gly Val Asp Ser Glu Ile Ala Tyr Gln Ala Gly
                100                 105                 110

Pro Gln Leu Val Val Pro Val Asn Asn Ala Arg Tyr Ala Ile Asn Ala
                115                 120                 125

Ala Asn Ala Arg Trp Gly Ser Leu Tyr Asp Ala Leu Tyr Gly Thr Asp
                130                 135                 140

Ala Ile Ser Glu Glu Asn Gly Ala Ser Arg Thr Ser Ser Tyr Asn Pro
145                 150                 155                 160

Ile Arg Gly Glu Lys Val Ile Ala Phe Ala Lys Asn Phe Leu Asp Glu
                165                 170                 175

Val Val Pro Leu Val Gln Ser Ser His Ala Glu Val Val Gln Tyr Ser
                180                 185                 190

Leu Glu Asn Glu Lys Leu Val Ala Gln Leu Asn Asp Gly Ser Leu Thr
                195                 200                 205

Glu Leu Gln Glu Glu Glu Lys Phe Val Gly Tyr Gln Gly Glu Glu Glu
                210                 215                 220

Ser Pro Asp Ala Leu Leu Phe Lys Asn Asn Gly Leu His Phe Glu Val
225                 230                 235                 240

Gln Ile Asp Arg Thr Asp Ser Ile Gly Lys Thr Asp Ala Gly Val
                245                 250                 255

Lys Asp Ile Leu Met Glu Ala Ala Leu Thr Thr Ile Met Asp Cys Glu
                260                 265                 270

Asp Ser Val Ala Ala Val Asp Ala Glu Asp Lys Val Asp Val Tyr Arg
                275                 280                 285

Asn Trp Leu Gly Leu Met Lys Gly Asp Leu Thr Ser Thr Phe Lys Lys
                290                 295                 300

Gly Ser Gln Asn Met Thr Arg Arg Leu Asn Pro Asp Arg Thr Tyr Ile
305                 310                 315                 320

Ser Pro Asp Lys Lys Lys Ile Leu Leu Ser Gly Arg Ser Leu Met Phe
                325                 330                 335

Val Arg Asn Val Gly His Leu Met Thr Asn Ser Ala Val Leu Asp Arg
                340                 345                 350

Asn Gly Asn Glu Ile Tyr Glu Gly Ile Leu Asp Ser Val Ile Thr Ser
                355                 360                 365

Leu Ile Ala Lys His Thr Leu Leu Lys Asn Gly Thr Tyr Gln Asn Ser
                370                 375                 380

Lys Lys Ser Ser Ile Tyr Ile Val Lys Pro Lys Met His Gly Ser Lys
385                 390                 395                 400

Glu Val Ala Phe Ala Asn Thr Leu Phe Asn Ser Ile Glu Asp Met Leu
                405                 410                 415

Gly Leu Glu Arg His Thr Ile Lys Ile Gly Val Met Asp Glu Glu Arg
                420                 425                 430
```

-continued

```
Arg Thr Thr Leu Asn Leu Lys Ala Cys Ile Lys Glu Val Lys Asp Arg
        435                 440                 445

Val Ala Phe Ile Asn Thr Gly Phe Leu Asp Arg Thr Gly Asp Glu Ile
450                 455                 460

His Thr Ser Met Glu Ala Gly Ala Val Ile Arg Lys Asn Asp Met Lys
465                 470                 475                 480

Ala Ser Lys Trp Leu Gln Gly Tyr Gln Ser Asn Val Asn Val Gly
                485                 490                 495

Leu Ala Ser Gly Phe Gln Gly Arg Ala Gln Ile Gly Lys Gly Met Trp
                500                 505                 510

Ala Met Pro Asp Met Met Ala Glu Met Leu Lys Gln Lys Val Gly His
            515                 520                 525

Leu Lys Ala Gly Ala Asn Thr Ala Trp Val Pro Ser Pro Thr Ala Ala
            530                 535                 540

Thr Leu His Ala Leu His Tyr His Gln Ile Asp Val Arg Asp Val Gln
545                 550                 555                 560

Asn Glu Leu Leu Thr Gln Ser Thr Asp Leu Gln Asp Ile Leu Gln
                565                 570                 575

Ile Pro Val Ala Glu Lys Pro Asn Trp Ser Lys Asp Glu Ile Gln Gln
            580                 585                 590

Glu Leu Asp Asn Asn Ala Gln Gly Ile Leu Gly Tyr Val Val Arg Trp
            595                 600                 605

Val Asp Gln Gly Val Gly Cys Ser Lys Val Pro Asp Ile Asn Asn Val
610                 615                 620

Gly Leu Met Glu Asp Arg Ala Thr Leu Arg Ile Ser Ser Gln His Val
625                 630                 635                 640

Ala Asn Trp Leu His His Gly Ile Cys Thr Lys Glu Gln Val Thr Glu
                645                 650                 655

Thr Leu Lys Arg Met Ala Lys Val Val Asp Gln Gln Asn Glu Asn Asp
            660                 665                 670

Pro Leu Tyr Gln Pro Met Ser Ser Asn Tyr Ser Ala Ser Ile Ala Phe
            675                 680                 685

Gln Ala Ala Cys Asp Leu Val Phe Gln Gly Tyr Asp Gln Pro Asn Gly
            690                 695                 700

Tyr Thr Glu Pro Ile Leu His Arg Arg Arg Ile Glu Ala Lys Ala Lys
705                 710                 715                 720

Ala Ala Ile Lys Gln
                725
```

<210> SEQ ID NO 43
<211> LENGTH: 1581
<212> TYPE: DNA
<213> ORGANISM: Artificial Sequence
<220> FEATURE:
<223> OTHER INFORMATION: Codon-adapted nucleotide sequence

<400> SEQUENCE: 43

```
atgtcaagac cagcagcagg acttgcagta ttaggaccac cactttcgtc agcagcacaa      60
gaattattag gtaaacgcgc attagcattc gttcaattac tagaacagca atttggacat     120
agaagaagag aattacttca ggctagacag cacagacaac agagatttga cggcggcgaa     180
aagcctgatt ttagatctga tactcttgca gttaggacgg gagaatggag tgtagctcca     240
gctccagcag aattacgcga caggagagtt gaaattactg gtcctgctgg agatagaaag     300
atggttataa atgctttaaa ttccggagca agagtattca tgtgtgatct tgaagacgct     360
```

```
aattcaccaa cttgggctaa cactatgaat ggtcagttaa atataagaga tgctgaggca      420
ggaactatag cttatgaatc accagaagga aaggcttata gacttgctcc agatcatgca      480
gtaattaaaa taagaccaag aggatggcat cttgaagaat ctcatgtagc atgggaagga      540
caaagtgttt ctgcagcttt atttgacttt ggaatggctg catttcataa tgcaagagaa      600
aaagcaagaa gaggatctgg cttgtacttc tatttaccta agttagaatc tatggaagaa      660
gcagaactat gggaagacgt attcacattt gcagaaagag agcttggtct tgaaagaggt      720
atgtttaggg ctacagtttt aatagaaacc ctaccagctg cctttgaaat ggaagaaata      780
cttttttgttc ttagagatca tgccgacgga ttgaattgtg aagatggga ttacatattt      840
agttatatta aaaagttaag agcacaccca gaggctatat taccagatag aagtttggtt      900
actatggata gccctttat ggcagcttat gctagacttg cagtacagac ttgtcataga      960
agaggcgcat tctgcatagg cggcatggct gcacagattc caatcaagaa tgattctgct     1020
gccaacgaac aagcactgga taaggtaaga cttgacaaat taagagaggt tagattaggg     1080
catgatggta cttgggttgc tcatcctgga cttgtagcag ttgctgaaaa agtatttaat     1140
gaacacatgc caggagataa tcaacttttc ttccatcctg atggttctgt tggtgctgaa     1200
caattgcttg aggctcctag aggaccaatt actgaggctg gagttagatt aaatttgtca     1260
gtttcacttc aatacattga ggcatggttg agaggtacag gtgcagttcc aataaacagc     1320
cttatggaag atgcagcaac tgctgaaatt tcaagagcac agttatggca gtggatacgg     1380
catccacaag gcatattaga agatggaaga aaaatgagtg cagatttata cagaaaatta     1440
ttagaagaag agcttggaaa attaccagca gcagcatcag gtgcttatgg acgggcagaa     1500
gaacttctta cagcaatgac tcttgccgat acttttgctg agttccttac tgtagacgct     1560
tatagatatc ttcaagatta g                                                1581
```

<210> SEQ ID NO 44
<211> LENGTH: 526
<212> TYPE: PRT
<213> ORGANISM: Paenibacillus sp. RU4X

<400> SEQUENCE: 44

```
Met Ser Arg Pro Ala Ala Gly Leu Ala Val Leu Gly Pro Pro Leu Ser
1               5                   10                  15

Ser Ala Ala Gln Glu Leu Leu Gly Lys Arg Ala Leu Ala Phe Val Gln
                20                  25                  30

Leu Leu Glu Gln Gln Phe Gly His Arg Arg Glu Leu Leu Gln Ala
            35                  40                  45

Arg Gln His Arg Gln Arg Phe Asp Gly Gly Glu Lys Pro Asp Phe
        50                  55                  60

Arg Ser Asp Thr Leu Ala Val Arg Thr Gly Glu Trp Ser Val Ala Pro
65                  70                  75                  80

Ala Pro Ala Glu Leu Arg Asp Arg Val Glu Ile Thr Gly Pro Ala
                85                  90                  95

Gly Asp Arg Lys Met Val Ile Asn Ala Leu Asn Ser Gly Ala Arg Val
                100                 105                 110

Phe Met Cys Asp Leu Glu Asp Ala Asn Ser Pro Thr Trp Ala Asn Thr
            115                 120                 125

Met Asn Gly Gln Leu Asn Ile Arg Asp Ala Glu Ala Gly Thr Ile Ala
        130                 135                 140

Tyr Glu Ser Pro Glu Gly Lys Ala Tyr Arg Leu Ala Pro Asp His Ala
```

145                 150                 155                 160
        Val Ile Lys Ile Arg Pro Arg Gly Trp His Leu Glu Glu Ser His Val
                        165                 170                 175

Ala Trp Glu Gly Gln Ser Val Ser Ala Ala Leu Phe Asp Phe Gly Met
                        180                 185                 190

Ala Ala Phe His Asn Ala Arg Glu Lys Ala Arg Arg Gly Ser Gly Leu
                        195                 200                 205

Tyr Phe Tyr Leu Pro Lys Leu Glu Ser Met Glu Glu Ala Glu Leu Trp
                        210                 215                 220

Glu Asp Val Phe Thr Phe Ala Glu Arg Glu Leu Gly Leu Glu Arg Gly
        225                 230                 235                 240

Met Phe Arg Ala Thr Val Leu Ile Glu Thr Leu Pro Ala Ala Phe Glu
                        245                 250                 255

Met Glu Glu Ile Leu Phe Val Leu Arg Asp His Ala Asp Gly Leu Asn
                        260                 265                 270

Cys Gly Arg Trp Asp Tyr Ile Phe Ser Tyr Ile Lys Lys Leu Arg Ala
                        275                 280                 285

His Pro Glu Ala Ile Leu Pro Asp Arg Ser Leu Val Thr Met Asp Ser
                        290                 295                 300

Pro Phe Met Ala Ala Tyr Ala Arg Leu Ala Val Gln Thr Cys His Arg
        305                 310                 315                 320

Arg Gly Ala Phe Cys Ile Gly Gly Met Ala Ala Gln Ile Pro Ile Lys
                        325                 330                 335

Asn Asp Ser Ala Ala Asn Glu Gln Ala Leu Asp Lys Val Arg Leu Asp
                        340                 345                 350

Lys Leu Arg Glu Val Arg Leu Gly His Asp Gly Thr Trp Val Ala His
                        355                 360                 365

Pro Gly Leu Val Ala Val Glu Lys Val Phe Asn Glu His Met Pro
                        370                 375                 380

Gly Asp Asn Gln Leu Phe Phe His Pro Asp Gly Ser Val Gly Ala Glu
        385                 390                 395                 400

Gln Leu Leu Glu Ala Pro Arg Gly Pro Ile Thr Glu Ala Gly Val Arg
                        405                 410                 415

Leu Asn Leu Ser Val Ser Leu Gln Tyr Ile Glu Ala Trp Leu Arg Gly
                        420                 425                 430

Thr Gly Ala Val Pro Ile Asn Ser Leu Met Glu Asp Ala Ala Thr Ala
                        435                 440                 445

Glu Ile Ser Arg Ala Gln Leu Trp Gln Trp Ile Arg His Pro Gln Gly
                        450                 455                 460

Ile Leu Glu Asp Gly Arg Lys Met Ser Ala Asp Leu Tyr Arg Lys Leu
        465                 470                 475                 480

Leu Glu Glu Glu Leu Gly Lys Leu Pro Ala Ala Ser Gly Ala Tyr
                        485                 490                 495

Gly Arg Ala Glu Glu Leu Leu Thr Ala Met Thr Leu Ala Asp Thr Phe
                        500                 505                 510

Ala Glu Phe Leu Thr Val Asp Ala Tyr Arg Tyr Leu Gln Asp
                        515                 520                 525

<210> SEQ ID NO 45
<211> LENGTH: 1599
<212> TYPE: DNA
<213> ORGANISM: Artificial Sequence
<220> FEATURE:
<223> OTHER INFORMATION: Codon-adapted nucleotide sequence

<400> SEQUENCE: 45

```
atgaaacaag caacaacagg aaaacttaaa atagttggag aacaaaatga gcatacaaac    60
gaaatactta ccccagaggc tttagaattt gttttagcac ttcatgaaaa atttgatgca   120
agaagaaagg aattattaaa tgcaagacaa aagagacaga agagattaga tgctggtgaa   180
aagctagatt tccttccaga gacaaaacat attagagaag gtgactggtc tatagctcct   240
cttccacaag atcttcagga tagacgtgtg gaaataactg gaccagtaga tagaaagatg   300
gtaataaatg ccttaaattc aggcgcaaag atgtttatgg catgttttga agatgcttca   360
agcccaactt gggaaaatat gataggcggc caaataaata tgagagatgc tataaataag   420
acaattgaat ttactcaggc ttcaaacggt aagacataca agctcaatgc ggaaactgct   480
gtattattag ttaggcctag aggattacat cttttagaaa agcacgtttt agttcatgac   540
gaacctatat caggctcatt ttttgacttt ggattatatt tatttcataa tgccaaaaat   600
gcactagcta aggaacagg tccttatttt tatttaccaa aacttgaatc acatctcgaa   660
gcaagacttt ggaatgatgt atttgtattt gcccaggatt atataggcat accacaagga   720
actataaagg ctactgtact cattgaaact atccttgctg catttgaaat ggatgaaatc   780
ctatatgaat tgagagaaca ttcagctgga cttaactgtg aagatgggga ttatatattc   840
agctatataa aaagacttag aaatcaggca gatgtaatac ttcctgatag gggacaagtt   900
actatgacag tgccttttat gaaggcttat acatcacttt gtattcaaac ctgtcacaaa   960
aggaatgctc ctgctatggg cggcatggct gcacaaatac ctataaaaaa cgatgatgaa  1020
gcgaatgctg tggcatttgc aaaggttgct gaggataaaa ggagagaggc tacagaagga  1080
catgatggta catgggttgc ccatccagga atggttgcaa ctgcaatgga acaatttgat  1140
gctattatga ctactcctaa tcaaatacat aaaaagagag aagatgtaca agttactgca  1200
gatgacctag ttgcagttcc agaaggtact ataactcttg aaggacttag agtaaattgt  1260
tcggttggag tacagtatat tgcaagttgg cttaggggaa atggggctgc ccctataaat  1320
aatcttatgg aagatgcagc aacagcagaa atttcaagaa ctcaagtatg gcaatgggtg  1380
agacacccaa aaggaatatt agatgatggc agaggaataa cttttagcttt tgttcttgaa  1440
atattggaag aagaattagt taaaattaaa gaggctgttg gtgaacaggc ttataattct  1500
ggaagatttg aagaggctgc tgaattattc aaatccctca tagaacaaga tgaatttgca  1560
gagttcctta cactaccagg atacgaaaaa ttggcataa                         1599
```

<210> SEQ ID NO 46
<211> LENGTH: 532
<212> TYPE: PRT
<213> ORGANISM: Lysinibacillus sp. A1

<400> SEQUENCE: 46

```
Met Lys Gln Ala Thr Thr Gly Lys Leu Lys Ile Val Gly Glu Gln Asn
1               5                   10                  15

Glu His Thr Asn Glu Ile Leu Thr Pro Glu Ala Leu Glu Phe Val Leu
            20                  25                  30

Ala Leu His Glu Lys Phe Asp Ala Arg Arg Lys Glu Leu Leu Asn Ala
        35                  40                  45

Arg Gln Lys Arg Gln Lys Arg Leu Asp Ala Gly Glu Lys Leu Asp Phe
    50                  55                  60

Leu Pro Glu Thr Lys His Ile Arg Glu Gly Asp Trp Ser Ile Ala Pro
65                  70                  75                  80
```

```
Leu Pro Gln Asp Leu Gln Asp Arg Arg Val Glu Ile Thr Gly Pro Val
                85                  90                  95

Asp Arg Lys Met Val Ile Asn Ala Leu Asn Ser Gly Ala Lys Met Phe
            100                 105                 110

Met Ala Cys Phe Glu Asp Ala Ser Ser Pro Thr Trp Glu Asn Met Ile
            115                 120                 125

Gly Gly Gln Ile Asn Met Arg Asp Ala Ile Asn Lys Thr Ile Glu Phe
            130                 135                 140

Thr Gln Ala Ser Asn Gly Lys Thr Tyr Lys Leu Asn Ala Glu Thr Ala
145                 150                 155                 160

Val Leu Leu Val Arg Pro Arg Gly Leu His Leu Leu Glu Lys His Val
                165                 170                 175

Leu Val His Asp Glu Pro Ile Ser Gly Ser Phe Phe Asp Phe Gly Leu
            180                 185                 190

Tyr Leu Phe His Asn Ala Lys Asn Ala Leu Ala Lys Gly Thr Gly Pro
            195                 200                 205

Tyr Phe Tyr Leu Pro Lys Leu Glu Ser His Leu Glu Ala Arg Leu Trp
            210                 215                 220

Asn Asp Val Phe Val Phe Ala Gln Asp Tyr Ile Gly Ile Pro Gln Gly
225                 230                 235                 240

Thr Ile Lys Ala Thr Val Leu Ile Glu Thr Ile Leu Ala Ala Phe Glu
                245                 250                 255

Met Asp Glu Ile Leu Tyr Glu Leu Arg Glu His Ser Ala Gly Leu Asn
            260                 265                 270

Cys Gly Arg Trp Asp Tyr Ile Phe Ser Tyr Ile Lys Arg Leu Arg Asn
            275                 280                 285

Gln Ala Asp Val Ile Leu Pro Asp Arg Gly Gln Val Thr Met Thr Val
            290                 295                 300

Pro Phe Met Lys Ala Tyr Thr Ser Leu Cys Ile Gln Thr Cys His Lys
305                 310                 315                 320

Arg Asn Ala Pro Ala Met Gly Gly Met Ala Ala Gln Ile Pro Ile Lys
                325                 330                 335

Asn Asp Asp Glu Ala Asn Ala Val Ala Phe Ala Lys Val Ala Glu Asp
            340                 345                 350

Lys Arg Arg Glu Ala Thr Glu Gly His Asp Gly Thr Trp Val Ala His
            355                 360                 365

Pro Gly Met Val Ala Thr Ala Met Glu Gln Phe Asp Ala Ile Met Thr
            370                 375                 380

Thr Pro Asn Gln Ile His Lys Lys Arg Glu Asp Val Gln Val Thr Ala
385                 390                 395                 400

Asp Asp Leu Val Ala Val Pro Glu Gly Thr Ile Thr Leu Glu Gly Leu
                405                 410                 415

Arg Val Asn Cys Ser Val Gly Val Gln Tyr Ile Ala Ser Trp Leu Arg
            420                 425                 430

Gly Asn Gly Ala Ala Pro Ile Asn Asn Leu Met Glu Asp Ala Ala Thr
            435                 440                 445

Ala Glu Ile Ser Arg Thr Gln Val Trp Gln Trp Val Arg His Pro Lys
            450                 455                 460

Gly Ile Leu Asp Asp Gly Arg Gly Ile Thr Leu Ala Phe Val Leu Glu
465                 470                 475                 480

Ile Leu Glu Glu Glu Leu Val Lys Ile Lys Glu Ala Val Gly Glu Gln
                485                 490                 495

Ala Tyr Asn Ser Gly Arg Phe Glu Glu Ala Ala Glu Leu Phe Lys Ser
```

```
                    500                 505                 510
Leu Ile Glu Gln Asp Glu Phe Ala Glu Phe Leu Thr Leu Pro Gly Tyr
        515                 520                 525
Glu Lys Leu Ala
    530

<210> SEQ ID NO 47
<211> LENGTH: 1590
<212> TYPE: DNA
<213> ORGANISM: Artificial Sequence
<220> FEATURE:
<223> OTHER INFORMATION: Codon-adapted nucleotide sequence

<400> SEQUENCE: 47
atgtcaacaa gaacatcaag agttacatta cctggagaaa tgttaccagc ttataacgaa       60
atacttaccc cagaagtttt atcattcctt aaagaattac atgaaaattt taatgaaaga      120
cgaacggaat tacttcaaaa aagggttgaa aacaaaaaa ggattgatgc gggtgaattt       180
ccaaaatttt tagaagaaac aaagcacatc agagaggctg attggacaat cgccaatctt      240
cctaaagacc ttgaagacag aagagtagaa ataacaggtc ctgtagatcg taaaatggtt      300
attaatgcat tgaattcagg agcacactta tttatggctg attttgaaga ttccaattca      360
ccaacttggg aaaatactat agaaggacaa ataaatttaa gagatgcagt aaaagggaca      420
ataagtcata aaaatgataa gggaaaagaa tataggttaa tgacaaaac agcagtttta       480 atagttaggc ctagaggatg gcacttagaa gaaaagcaca tgcaggttga tggaaagaat      540
atgtcgggat ctcttgtaga ttttggatta tatttttttc ataatgcaaa ggctctatta      600
gaaaaaggtt caggaccata cttctattta cctaaaatgg aatcttatct tgaagcaaga      660 cttttggaacg atgtatttgt atttgctcaa aagtatatag gtataccaaa tggaactatc      720
aaggcaactg tattattgga aactatccat gcatcatttg aaatggatga aattctttat      780
gaattaaaag atcattcagc aggattaaat tgtggacgct gggattatat ttttttcttc      840
ctaaaaggat ttagaaacca caatgaattt cttttaccag ataggctca agtaactatg       900 actgctcctt ttatgagggc ttattctctc aaggtaatcc aaacttgtca tagaagaaat      960
gcaccagcta taggcggcat ggctgcacaa attcctataa aaataatcc agaggctaat      1020 gaagcagcat ttgaaaaagt aagagcagat aaagaaagag aagcattaga tggtcatgac      1080
ggtacttggg tagcacatcc tggcttagtt cccgttgcta tggaagtatt taatcatatc      1140
atgaaaactc ctaatcagat atttcgcaaa agagaagaga taagagttac ggaaaaggat      1200
ttacttgaag ttcctgtagg tacaatcact gaagaagggt taagaactaa catatctgtt      1260
ggaatacagt acatagcatc atggttatca ggaagagggg ctgccctat atataatctc      1320 atggaagatg cagctactgc agaaatttcc agggctcaaa tttggcaatg gataagacat      1380
gaaggcggca aactaaacga tggtagaaat attacattgg aattaatgga agaatggaaa      1440
gaagaagaat tggtaaagat agaacgggaa ataggaaaag aggcattcaa aaaaggcaga      1500
tttcaagagg ctactacatt atttacaaat ttgataagaa atgatgaatt tgtcccattc      1560
cttactttac ctggatacga gatattataa                                      1590

<210> SEQ ID NO 48
<211> LENGTH: 529
<212> TYPE: PRT
<213> ORGANISM: Bacillus cereus

<400> SEQUENCE: 48
```

```
Met Ser Thr Arg Thr Ser Arg Val Thr Leu Pro Gly Glu Met Leu Pro
1               5                   10                  15

Ala Tyr Asn Glu Ile Leu Thr Pro Glu Val Leu Ser Phe Leu Lys Glu
            20                  25                  30

Leu His Glu Asn Phe Asn Glu Arg Arg Thr Glu Leu Leu Gln Lys Arg
        35                  40                  45

Val Glu Lys Gln Lys Arg Ile Asp Ala Gly Glu Phe Pro Lys Phe Leu
    50                  55                  60

Glu Glu Thr Lys His Ile Arg Glu Ala Asp Trp Thr Ile Ala Asn Leu
65              70                  75                  80

Pro Lys Asp Leu Glu Asp Arg Arg Val Glu Ile Thr Gly Pro Val Asp
                85                  90                  95

Arg Lys Met Val Ile Asn Ala Leu Asn Ser Gly Ala His Leu Phe Met
            100                 105                 110

Ala Asp Phe Glu Asp Ser Asn Ser Pro Thr Trp Glu Asn Thr Ile Glu
        115                 120                 125

Gly Gln Ile Asn Leu Arg Asp Ala Val Lys Gly Thr Ile Ser His Lys
    130                 135                 140

Asn Asp Lys Gly Lys Glu Tyr Arg Leu Asn Asp Lys Thr Ala Val Leu
145                 150                 155                 160

Ile Val Arg Pro Arg Gly Trp His Leu Glu Glu Lys His Met Gln Val
                165                 170                 175

Asp Gly Lys Asn Met Ser Gly Ser Leu Val Asp Phe Gly Leu Tyr Phe
            180                 185                 190

Phe His Asn Ala Lys Ala Leu Leu Glu Lys Gly Ser Gly Pro Tyr Phe
        195                 200                 205

Tyr Leu Pro Lys Met Glu Ser Tyr Leu Glu Ala Arg Leu Trp Asn Asp
    210                 215                 220

Val Phe Val Phe Ala Gln Lys Tyr Ile Gly Ile Pro Asn Gly Thr Ile
225                 230                 235                 240

Lys Ala Thr Val Leu Leu Glu Thr Ile His Ala Ser Phe Glu Met Asp
                245                 250                 255

Glu Ile Leu Tyr Glu Leu Lys Asp His Ser Ala Gly Leu Asn Cys Gly
            260                 265                 270

Arg Trp Asp Tyr Ile Phe Ser Phe Leu Lys Gly Phe Arg Asn His Asn
        275                 280                 285

Glu Phe Leu Leu Pro Asp Arg Ala Gln Val Thr Met Thr Ala Pro Phe
    290                 295                 300

Met Arg Ala Tyr Ser Leu Lys Val Ile Gln Thr Cys His Arg Arg Asn
305                 310                 315                 320

Ala Pro Ala Ile Gly Gly Met Ala Ala Gln Ile Pro Ile Lys Asn Asn
                325                 330                 335

Pro Glu Ala Asn Glu Ala Ala Phe Glu Lys Val Arg Ala Asp Lys Glu
            340                 345                 350

Arg Glu Ala Leu Asp Gly His Asp Gly Thr Trp Val Ala His Pro Gly
        355                 360                 365

Leu Val Pro Val Ala Met Glu Val Phe Asn His Ile Met Lys Thr Pro
    370                 375                 380

Asn Gln Ile Phe Arg Lys Arg Glu Glu Ile Arg Val Thr Glu Lys Asp
385                 390                 395                 400

Leu Leu Glu Val Pro Val Gly Thr Ile Thr Glu Glu Gly Leu Arg Thr
                405                 410                 415
```

```
Asn Ile Ser Val Gly Ile Gln Tyr Ile Ala Ser Trp Leu Ser Gly Arg
                420                 425                 430

Gly Ala Ala Pro Ile Tyr Asn Leu Met Glu Asp Ala Thr Ala Glu
            435                 440                 445

Ile Ser Arg Ala Gln Ile Trp Gln Trp Ile Arg His Glu Gly Gly Lys
        450                 455                 460

Leu Asn Asp Gly Arg Asn Ile Thr Leu Glu Leu Met Glu Glu Trp Lys
465                 470                 475                 480

Glu Glu Glu Leu Val Lys Ile Glu Arg Glu Ile Gly Lys Glu Ala Phe
                485                 490                 495

Lys Lys Gly Arg Phe Gln Glu Ala Thr Thr Leu Phe Thr Asn Leu Ile
            500                 505                 510

Arg Asn Asp Glu Phe Val Pro Phe Leu Thr Leu Pro Gly Tyr Glu Ile
        515                 520                 525

Leu
```

<210> SEQ ID NO 49
<211> LENGTH: 1425
<212> TYPE: DNA
<213> ORGANISM: Artificial Sequence
<220> FEATURE:
<223> OTHER INFORMATION: Codon-adapted nucleotide sequence

<400> SEQUENCE: 49

```
atgcagcaca aattattaat taacggagaa cttgtaagtg agaaggaga  aaacaacca      60 gtatataacc cagcaactgg agatgtatta ttagaaatag cagaggcatc agcagaacag    120
gtagatgctg cagttagggc agcagacgca gcatttgcag agtggggaca aactactcct    180
aaagtgcgtg cagaatgtct tctaaaactt gcagacgtta tagaggaaaa tggacaagta    240
tttgctgaat ggagtcgag  aaactgcggt aaacctttac attcagcatt taatgatgaa    300
ataccagcaa tagtagatgt attcagattt tttgctggtg cagctaggtg tcttaacgga    360
ctagcagctg gagagtatct tgaaggacat acatcaatga taagaagaga tccattaggt    420
gtagttgcca gtatagctcc ttggaactat cctttgatga tggcagcatg gaaacttgcc    480
cccgcccttg cagcaggaaa ttgtgttgta ttgaaaccaa gtgaaataac ccctcttaca    540
gcattaaaat tagctgaatt agcaaaggac atcttcccag ctggtgttat aaatatacta    600
tttggaagag gcaaaacagt tggtgatcct ttgacaggac atcctaaggt aaggatggtt    660
agccttacag gctcaatagc aacaggcgaa catattatat cacacacggc atcttctata    720
aaacgcacgc acatggaatt gggcggcaaa gccccggtta ttgtatttga tgatgcagat    780
atagaggcag tagtagaagg agttagaact tttggatatt ataatgctgg ccaagattgt    840
actgctgctt gtaggattta tgctcaaaaa ggtatttatg atacttgt  tgaaaagcta    900 ggtgctgcag ttgcaaccct taagtctggt gcaccagatg atgaatctac agaattggga    960
cctttatctt ctttagcaca ccttgaaaga gttagcaaag cagttgaaga ggctaaggct   1020
actggacata taaaggtaat aacaggcggc gaaaagagaa agggaaatgg atattattat   1080
gctcctacgc ttttagctgg tgcccttcag gatgatgcta gtacagaa  agaagtattt   1140 ggaccagtag taagtgtaac tcctttgat  aatgaagaac aggtagttaa ctgggccaat   1200
gatagccagt acggattagc gtcttctgta tggacaaagg atgtaggcag agcacatagg   1260
gtatcagcaa gacttcaata tggatgtact tgggtaaata ctcactttat gttagtaagt   1320
gagatgccac atggcggcca aaagttgtca ggatatggaa aagatatgag cttatacggt   1380
```
ttggaagact atacagtagt aagacacgta atggtaaaac attag 1425

<210> SEQ ID NO 50
<211> LENGTH: 474
<212> TYPE: PRT
<213> ORGANISM: Escherichia coli

<400> SEQUENCE: 50

Met Gln His Lys Leu Leu Ile Asn Gly Glu Leu Val Ser Gly Glu Gly
1               5                   10                  15

Glu Lys Gln Pro Val Tyr Asn Pro Ala Thr Gly Asp Val Leu Leu Glu
            20                  25                  30

Ile Ala Glu Ala Ser Ala Glu Gln Val Asp Ala Ala Val Arg Ala Ala
        35                  40                  45

Asp Ala Ala Phe Ala Glu Trp Gly Gln Thr Thr Pro Lys Val Arg Ala
    50                  55                  60

Glu Cys Leu Leu Lys Leu Ala Asp Val Ile Glu Glu Asn Gly Gln Val
65                  70                  75                  80

Phe Ala Glu Leu Glu Ser Arg Asn Cys Gly Lys Pro Leu His Ser Ala
                85                  90                  95

Phe Asn Asp Glu Ile Pro Ala Ile Val Asp Val Phe Arg Phe Phe Ala
            100                 105                 110

Gly Ala Ala Arg Cys Leu Asn Gly Leu Ala Ala Gly Glu Tyr Leu Glu
        115                 120                 125

Gly His Thr Ser Met Ile Arg Arg Asp Pro Leu Gly Val Val Ala Ser
    130                 135                 140

Ile Ala Pro Trp Asn Tyr Pro Leu Met Met Ala Ala Trp Lys Leu Ala
145                 150                 155                 160

Pro Ala Leu Ala Ala Gly Asn Cys Val Val Leu Lys Pro Ser Glu Ile
                165                 170                 175

Thr Pro Leu Thr Ala Leu Lys Leu Ala Glu Leu Ala Lys Asp Ile Phe
            180                 185                 190

Pro Ala Gly Val Ile Asn Ile Leu Phe Gly Arg Gly Lys Thr Val Gly
        195                 200                 205

Asp Pro Leu Thr Gly His Pro Lys Val Arg Met Val Ser Leu Thr Gly
    210                 215                 220

Ser Ile Ala Thr Gly Glu His Ile Ile Ser His Thr Ala Ser Ser Ile
225                 230                 235                 240

Lys Arg Thr His Met Glu Leu Gly Gly Lys Ala Pro Val Ile Val Phe
                245                 250                 255

Asp Asp Ala Asp Ile Glu Ala Val Val Glu Gly Val Arg Thr Phe Gly
            260                 265                 270

Tyr Tyr Asn Ala Gly Gln Asp Cys Thr Ala Ala Cys Arg Ile Tyr Ala
        275                 280                 285

Gln Lys Gly Ile Tyr Asp Thr Leu Val Glu Lys Leu Gly Ala Ala Val
    290                 295                 300

Ala Thr Leu Lys Ser Gly Ala Pro Asp Asp Glu Ser Thr Glu Leu Gly
305                 310                 315                 320

Pro Leu Ser Ser Leu Ala His Leu Glu Arg Val Ser Lys Ala Val Glu
                325                 330                 335

Glu Ala Lys Ala Thr Gly His Ile Lys Val Ile Thr Gly Gly Glu Lys
            340                 345                 350

Arg Lys Gly Asn Gly Tyr Tyr Tyr Ala Pro Thr Leu Leu Ala Gly Ala
        355                 360                 365

Leu Gln Asp Asp Ala Ile Val Gln Lys Glu Val Phe Gly Pro Val Val
370             375                 380

Ser Val Thr Pro Phe Asp Asn Glu Glu Gln Val Val Asn Trp Ala Asn
385             390                 395                 400

Asp Ser Gln Tyr Gly Leu Ala Ser Ser Val Trp Thr Lys Asp Val Gly
            405                 410                 415

Arg Ala His Arg Val Ser Ala Arg Leu Gln Tyr Gly Cys Thr Trp Val
            420                 425                 430

Asn Thr His Phe Met Leu Val Ser Glu Met Pro His Gly Gly Gln Lys
            435                 440                 445

Leu Ser Gly Tyr Gly Lys Asp Met Ser Leu Tyr Gly Leu Glu Asp Tyr
450             455                 460

Thr Val Val Arg His Val Met Val Lys His
465             470

<210> SEQ ID NO 51
<211> LENGTH: 1440
<212> TYPE: DNA
<213> ORGANISM: Artificial Sequence
<220> FEATURE:
<223> OTHER INFORMATION: Codon-adapted nucleotide sequence

<400> SEQUENCE: 51
atgtcagttc cggttcagca cccaatgtat attgatggac aatttgtaac ttggcgagga     60
gatgcatgga tagatgttgt gaatccagcg actgaggcag ttatctctag gattcctgat    120
ggtcaggcag aggatgccag aaaagcaata gatgctgcaa aagggctcaa ccagaatgg     180 gaagcgttac ctgctattga agggcttcc tggttacgaa aaatttcagc aggaataaga    240
gaaagagcat cagaaatatc agcactaata gttgaagaag cggcaaaat tcaacaactt    300 gcagaggttg aagtagcatt tacagcggat tatattgatt catggctga atgggcaaga    360 agatacgaag agagagattat tcaatctgat agaccaggag aaaatatctt attattcaaa    420
agagcattag gtgttacaac aggcattctt ccttggaatt ttccattctt cctaattgca    480
agaaagatgg ccccagcact acttacagga aatactattg taataaaacc ttcagaattt    540
actcctaata atgctatagc ttttgctaaa attgtagatg aaataggact tccaagaggt    600
gtatttaatc tagtactagg acgtggtgaa actgtaggac aagaattagc tggaaatccg    660
aaggtagcaa tggtttctat gactggatca gtttccgctg gtgaaaaaat aatggcgact    720
gcagctaaaa acattacaaa gtatgcttg gagcttggcg gcaaagcacc agcaattgta    780
atggatgatg cagatttaga acttgcagta aaggctattg tagattcaag agtaataaac    840
agtggtcagg tatgcaattg tgctgaacgt atttatgtac aaaaaggtat atatgatcaa    900
tttgtaaatc gattgggtga agcaatgcaa gcagtacaat tggaaaccc agctgaacgg    960 aacgatatag cgatgggacc tttaataaat gcagcagcac ttgaaagagt tgaacaaaaa    1020
gtagctaggg ctgtggaaga aggagcaaga gttgcattgg gcggcaaggc agttgaaggt    1080
aaaggatatt attatcctcc tacactttta ctagatgttc ttcaagaaat gagtataatg    1140
catgaagaaa ctttggacc tgtattacca gttgtagctt tgatacttt agaagaggct    1200 atatcaatgg caaatgattc tgactatggc ttaactagca gcatatacac tcaaaatcta    1260
aacgtagcta tgaaggctat taagggtta aaatttggtg agacttatat aaatagagaa    1320
aactttgagg ctatgcaagg ttttcatgct ggatggagaa aaagtggtat tggcggcgct    1380
gacggaaagc atggacttca tgaatattta cagactcagg ttgtttatct tcaatcttaa    1440

<210> SEQ ID NO 52
<211> LENGTH: 479
<212> TYPE: PRT
<213> ORGANISM: Escherichia coli

<400> SEQUENCE: 52

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Ile Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Leu Gly Gly Lys Ala Val Glu Gly Lys Gly Tyr Tyr Tyr Pro Pro Thr
        355                 360                 365

Leu Leu Leu Asp Val Leu Gln Glu Met Ser Ile Met His Glu Glu Thr
    370                 375                 380
```

```
Phe Gly Pro Val Leu Pro Val Val Ala Phe Asp Thr Leu Glu Glu Ala
385                 390                 395                 400

Ile Ser Met Ala Asn Asp Ser Asp Tyr Gly Leu Thr Ser Ser Ile Tyr
            405                 410                 415

Thr Gln Asn Leu Asn Val Ala Met Lys Ala Ile Lys Gly Leu Lys Phe
        420                 425                 430

Gly Glu Thr Tyr Ile Asn Arg Glu Asn Phe Glu Ala Met Gln Gly Phe
    435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475
```

<210> SEQ ID NO 53
<211> LENGTH: 1449
<212> TYPE: DNA
<213> ORGANISM: Artificial Sequence
<220> FEATURE:
<223> OTHER INFORMATION: Codon-adapted nucleotide sequence

<400> SEQUENCE: 53

```
atgaaattaa atgattcaaa acttttttaga caacaagcct taataaatgg agaatggtta      60
gatgcaaata acgagaagt aatagatgtt actaatccag caatggtga taaacttggt       120
tctgttccaa agatgggagc agatgaaacc agggctgcta tagatgcagc aaatagagca     180
cttccagcat ggagagcact tacagcaaaa gaacgggcaa atatacttag aaattggttt     240
aatcttttaa tggaacatca ggatgatcta gcaaggctta tgacgcttga acagggaaaa     300
cctcttgctg aggctaaagg agagatcagt tatgcagcgt catttataga atggtttgct     360
gaagaaggaa aaaggattta tggagatact ataccaggac atcaggcaga caaaagactt     420
atagttatta acaacctat aggtgtaact gctgctataa ctccttggaa cttcccagca      480
gctatgataa ctagaaaagc aggaccagct cttgctgctg gttgcactat ggttttaaaa    540
cctgcttccc agactccttt tagtgcccctt gcacttgctg aattagctat tcgtgctggt    600
attccagcgg gtgtattcaa tgtagttact ggatctgctg gtgcggttgg aaatgagctt    660
acatcaaatc cgcttgtaag aaaactttca tttacaggaa gtacagaaat aggtaggcaa   720
ttaatggaac aatgtgctaa agatattaag aaagtttcac tggagttagg cggcaatgcc   780
ccttttattg tatttgatga tgcagactta gataaagcag ttgaaggtgc tttaagttct     840
aaatttagga atgctggaca aacttgtgta tgtgcgaata gattatacgt ccaagacgga    900
gtttacgata gatttgcaga aaaacttcaa caggctgtat ctaaattaca cattggagat    960
gggttagaga aaggcgttac aattggccca ttgatagatg aaaaagcagt agctaaagtt  1020
gaggaacaca ttgctgatgc acttgaaaaa ggtgctagag ttgtttgcgg cggcaaggct  1080
gatgaaagag gcggcaactt tttccagcct actatacttg tagacgttcc agctaatgca  1140
aaggtatcaa agaggaaac ctttggtcca cttgctcctt tatttagatt taaggatgag  1200
gcagatgtta tagcacaggc aaatgatacc gaatttggac ttgcagctta tttctatgct  1260
agggatttat ccagggtttt tagagttggt gaggctttag tacggcat gttggaata   1320
aatactggaa taatatcaaa tgaagttgca ccatttggcg gcataaaggc tagtggatta  1380
gggagagaag gctcaaaata tggaatagaa gactatttgg aaataaaata tatgtgcatt  1440
ggcttataa                                                                        1449
```

<210> SEQ ID NO 54
<211> LENGTH: 482
<212> TYPE: PRT
<213> ORGANISM: Escherichia coli

<400> SEQUENCE: 54

```
Met Lys Leu Asn Asp Ser Lys Leu Phe Arg Gln Gln Ala Leu Ile Asn
1               5                   10                  15

Gly Glu Trp Leu Asp Ala Asn Asn Gly Glu Val Ile Asp Val Thr Asn
            20                  25                  30

Pro Ala Asn Gly Asp Lys Leu Gly Ser Val Pro Lys Met Gly Ala Asp
        35                  40                  45

Glu Thr Arg Ala Ala Ile Asp Ala Ala Asn Arg Ala Leu Pro Ala Trp
    50                  55                  60

Arg Ala Leu Thr Ala Lys Glu Arg Ala Asn Ile Leu Arg Asn Trp Phe
65                  70                  75                  80

Asn Leu Leu Met Glu His Gln Asp Asp Leu Ala Arg Leu Met Thr Leu
                85                  90                  95

Glu Gln Gly Lys Pro Leu Ala Glu Ala Lys Gly Glu Ile Ser Tyr Ala
            100                 105                 110

Ala Ser Phe Ile Glu Trp Phe Ala Glu Glu Gly Lys Arg Ile Tyr Gly
        115                 120                 125

Asp Thr Ile Pro Gly His Gln Ala Asp Lys Arg Leu Ile Val Ile Lys
    130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Phe Ser Ala Leu Ala Leu
            180                 185                 190

Ala Glu Leu Ala Ile Arg Ala Gly Ile Pro Ala Gly Val Phe Asn Val
        195                 200                 205

Val Thr Gly Ser Ala Gly Ala Val Gly Asn Glu Leu Thr Ser Asn Pro
    210                 215                 220

Leu Val Arg Lys Leu Ser Phe Thr Gly Ser Thr Glu Ile Gly Arg Gln
225                 230                 235                 240

Leu Met Glu Gln Cys Ala Lys Asp Ile Lys Lys Val Ser Leu Glu Leu
                245                 250                 255

Gly Gly Asn Ala Pro Phe Ile Val Phe Asp Asp Ala Asp Leu Asp Lys
            260                 265                 270

Ala Val Glu Gly Ala Leu Ser Ser Lys Phe Arg Asn Ala Gly Gln Thr
        275                 280                 285

Cys Val Cys Ala Asn Arg Leu Tyr Val Gln Asp Gly Val Tyr Asp Arg
    290                 295                 300

Phe Ala Glu Lys Leu Gln Gln Ala Val Ser Lys Leu His Ile Gly Asp
305                 310                 315                 320

Gly Leu Glu Lys Gly Val Thr Ile Gly Pro Leu Ile Asp Glu Lys Ala
                325                 330                 335

Val Ala Lys Val Glu Glu His Ile Ala Asp Ala Leu Glu Lys Gly Ala
            340                 345                 350

Arg Val Val Cys Gly Gly Lys Ala Asp Glu Arg Gly Gly Asn Phe Phe
        355                 360                 365

Gln Pro Thr Ile Leu Val Asp Val Pro Ala Asn Ala Lys Val Ser Lys
    370                 375                 380
```

```
Glu Glu Thr Phe Gly Pro Leu Ala Pro Leu Phe Arg Phe Lys Asp Glu
385                 390                 395                 400

Ala Asp Val Ile Ala Gln Ala Asn Asp Thr Glu Phe Gly Leu Ala Ala
            405                 410                 415

Tyr Phe Tyr Ala Arg Asp Leu Ser Arg Val Phe Arg Val Gly Glu Ala
        420                 425                 430

Leu Glu Tyr Gly Ile Val Gly Ile Asn Thr Gly Ile Ile Ser Asn Glu
    435                 440                 445

Val Ala Pro Phe Gly Ile Lys Ala Ser Gly Leu Gly Arg Glu Gly
    450                 455                 460

Ser Lys Tyr Gly Ile Glu Asp Tyr Leu Glu Ile Lys Tyr Met Cys Ile
465                 470                 475                 480

Gly Leu
```

<210> SEQ ID NO 55
<211> LENGTH: 1443
<212> TYPE: DNA
<213> ORGANISM: Artificial Sequence
<220> FEATURE:
<223> OTHER INFORMATION: Codon-adapted nucleotide sequence

<400> SEQUENCE: 55

```
atgactgaaa aaataatttt attcataaat ggatcttggg ttgctcctaa aggcggcgaa      60
tggattaaag ttgaaaaccc agctacaaag gcagtagtgg cagaagtagc aaagggcggc     120
caggctgacg tagtgctgcc tgtatcagca gctaagtcag catttattgg atggtcaaga     180
aggatggcaa ctgagagagc agattatata catgcattaa aagatcttgt gaaaagggat     240
aaagaaaaat tagcagctat tataactagt gaaatgggga aaccattgaa agaggctaga     300
atagaagtag attttgcaat tggattactt agatttgcag cagaaaatgt tttaagactt     360
cagggagaaa taataccagg atcttctcca gaagaaaaga tattaattga tagggtacct     420
ttgggagtaa taggtgctat aacagcatgg aattttcctc ttgcactttg tgcaagaaag     480
attggacctg ctgtggcagc gggaaatact atagttgtaa aaccacatga attaacgcca     540
ttagcttgtc tacatcttgc taaattagtt gaagaggcaa gatcccaca tggagttata      600
aatgttgtaa caggtgatgg caaagatgta ggagtacctc tagtagcaca taagatatt      660
aaattaataa ctatgacagg ttccacgcct gctggaaaaa aattatggc agcagctagt      720
gagacactta agaagttagt tagaacttg gcggcaaag caccatttat ggttatggaa      780
gatgctgata ttgacagggc agcagatgct gccgttacag caagatttaa taatgcggga     840
caggtatgta cttgtaatga aagaacctac attcatgaag cagtttacga caaatttgtt     900
caaaaagtta gagaaaaaat agaagcatta aagtaggac tgccaacaga tccatctaca      960
gatatgggac ctaaagtatc tgaggacgaa cttaataaag ttcatgagat ggttgaacat    1020
gctgtaagac aaggagcaag attagctata ggcggcaaaa ggttaactgg cggcgtttat    1080
gataagggat acttctatgc accaacactg ttgacagatg taactcaaga tatggacata    1140
gttcacaatg aggtatttgg tcctgtaatg tcattgatta gagttaaaga ttttgatcag    1200
gctatagcat gggcaaatga ttgtagatac gggctaagtg cttatctttt cactaatgat    1260
ctttcaagga tacttaggat gacaagagat cttgaatttg gagaagtata cgtgaaccgt    1320
ccgggcggcg aagcgccaca aggatttcat catggataca aagaatctgg acttggcggc    1380
gaggacggac agcacggaat ggaagcatac gtacagacaa aaacaatata tctaaatgca    1440
``` taa                                                                      1443

<210> SEQ ID NO 56
<211> LENGTH: 480
<212> TYPE: PRT
<213> ORGANISM: Gluconobacter oxydans

<400> SEQUENCE: 56

Met Thr Glu Lys Asn Asn Leu Phe Ile Asn Gly Ser Trp Val Ala Pro
1               5                   10                  15

Lys Gly Gly Glu Trp Ile Lys Val Glu Asn Pro Ala Thr Lys Ala Val
            20                  25                  30

Val Ala Glu Val Ala Lys Gly Gly Gln Ala Asp Val Asp Ala Ala Val
        35                  40                  45

Ser Ala Ala Lys Ser Ala Phe Ile Gly Trp Ser Arg Arg Met Ala Thr
    50                  55                  60

Glu Arg Ala Asp Tyr Ile His Ala Leu Lys Asp Leu Val Lys Arg Asp
65                  70                  75                  80

Lys Glu Lys Leu Ala Ala Ile Ile Thr Ser Glu Met Gly Lys Pro Leu
                85                  90                  95

Lys Glu Ala Arg Ile Glu Val Asp Phe Ala Ile Gly Leu Leu Arg Phe
            100                 105                 110

Ala Ala Glu Asn Val Leu Arg Leu Gln Gly Glu Ile Ile Pro Gly Ser
        115                 120                 125

Ser Pro Glu Glu Lys Ile Leu Ile Asp Arg Val Pro Leu Gly Val Ile
    130                 135                 140

Gly Ala Ile Thr Ala Trp Asn Phe Pro Leu Ala Leu Cys Ala Arg Lys
145                 150                 155                 160

Ile Gly Pro Ala Val Ala Ala Gly Asn Thr Ile Val Val Lys Pro His
                165                 170                 175

Glu Leu Thr Pro Leu Ala Cys Leu His Leu Ala Lys Leu Val Glu Glu
            180                 185                 190

Ala Lys Ile Pro His Gly Val Ile Asn Val Val Thr Gly Asp Gly Lys
        195                 200                 205

Asp Val Gly Val Pro Leu Val Ala His Lys Asp Ile Lys Leu Ile Thr
    210                 215                 220

Met Thr Gly Ser Thr Pro Ala Gly Lys Lys Ile Met Ala Ala Ala Ser
225                 230                 235                 240

Glu Thr Leu Lys Glu Val Arg Leu Glu Leu Gly Gly Lys Ala Pro Phe
                245                 250                 255

Met Val Met Glu Asp Ala Asp Ile Asp Arg Ala Ala Asp Ala Ala Val
            260                 265                 270

Thr Ala Arg Phe Asn Asn Ala Gly Gln Val Cys Thr Cys Asn Glu Arg
        275                 280                 285

Thr Tyr Ile His Glu Ala Val Tyr Asp Lys Phe Val Gln Lys Val Arg
    290                 295                 300

Glu Lys Ile Glu Ala Leu Lys Val Gly Leu Pro Thr Asp Pro Ser Thr
305                 310                 315                 320

Asp Met Gly Pro Lys Val Ser Glu Asp Glu Leu Asn Lys Val His Glu
                325                 330                 335

Met Val Glu His Ala Val Arg Gln Gly Ala Arg Leu Ala Ile Gly Gly
            340                 345                 350

Lys Arg Leu Thr Gly Gly Val Tyr Asp Lys Gly Tyr Phe Tyr Ala Pro
        355                 360                 365

| | | | | | | | | | | | |
|---|---|---|---|---|---|---|---|---|---|---|---|
|Thr|Leu|Leu|Thr|Asp|Val|Thr|Gln|Asp|Met|Asp|Ile Val His Asn Glu|
| |370| | | |375| | | |380| | |

Val Phe Gly Pro Val Met Ser Leu Ile Arg Val Lys Asp Phe Asp Gln
385                 390                 395                 400

Ala Ile Ala Trp Ala Asn Asp Cys Arg Tyr Gly Leu Ser Ala Tyr Leu
                405                 410                 415

Phe Thr Asn Asp Leu Ser Arg Ile Leu Arg Met Thr Arg Asp Leu Glu
            420                 425                 430

Phe Gly Glu Val Tyr Val Asn Arg Pro Gly Gly Glu Ala Pro Gln Gly
        435                 440                 445

Phe His His Gly Tyr Lys Glu Ser Gly Leu Gly Glu Asp Gly Gln
    450                 455                 460

His Gly Met Glu Ala Tyr Val Gln Thr Lys Thr Ile Tyr Leu Asn Ala
465                 470                 475                 480

<210> SEQ ID NO 57
<211> LENGTH: 1434
<212> TYPE: DNA
<213> ORGANISM: Artificial Sequence
<220> FEATURE:
<223> OTHER INFORMATION: Codon-adapted nucleotide sequence

<400> SEQUENCE: 57

```
atgtcttcag tgcctgtatt ccagaacttt ataaatggac aatttacgca tagtgaagcc      60
catcttgatg tttataatcc cgccacagga gcacttttat caagggtacc agcaagtact     120
tgtgcagatg tagatcaggc tcttgctggt gcaagagcag ctcaaaaagc atggtcagca     180
aaaccagcaa tagaaagggc aggataccct agacgtattg cttcaaaact tagagaaaat     240
gttgctcatc ttgcaagaac tataactcta gaacaaggaa aaatatcagc attagcagaa     300
gttgaagtaa acttcacagc tgactacctt gattatatgg cagaatgggc tagaagaata     360
gaaggcgaaa taataacttc agatcgccca ggggaaaaca tattcctttt tcgtaaacct     420
ttaggagtag tggcaggaat acttccttgg aatttcccct tcttcttaat cgcaagaaaa     480
atggcaccag cattgcttac aggcaataca attgttataa aaccaagtga agagacacca     540
aataattgtt ttgaatttgc tagacttgta gctgagactg atttacctcc aggagttttt     600
aatgttgtat gtggagatgg aagagtagga gcagcattaa gtgggcataa aggagtagat     660
atgataagct ttcaggctc agttgacaca ggatcacgaa taatgactgc agcagcgact     720
aatattacaa aattaaattt ggaacttggc ggcaaggcac cagctatagt tttggcagat     780
gcagatcttg cattggcagt aaaagcaata agagattcaa gaataataaa tactggacaa     840
gtatgtaatt gtgctgaaag agtatatgtt gagagaaaag tagctgatca atttatagaa     900
agaataagtc tgcaatgtc agctacaaga tacggagatc cattagctga ccggatgta     960
gagatgggac cattaataaa caggcaagga cttgattctg tagaaagaaa agtacgtatt    1020
gctcttcaac agggtgcttc tcttattagt ggcggccgag tagcagatag acctgatgga    1080
ttccattttg agccaactgt attagcagga tgtaatgctt caatggatat tatgagagaa    1140
gaaatatttg gccagttttt accaatccaa atagtagatg atttagatga agcaatcgct    1200
ttagctaacg actgcgatta tggattaact tcatctgtat atacaaggga ccttggacgt    1260
gctatgcatg ctataagagg attagatttt ggtgaaactt atgttaatag ggaaaatttt    1320
gaggctatgc agggattcca tgctggtgta agaaagtcag gagtaggcgg cgcagatggc    1380
aagcatggat tatatgaata tactcatact catgcagtat atctccagtc ttaa          1434
```

<210> SEQ ID NO 58
<211> LENGTH: 477
<212> TYPE: PRT
<213> ORGANISM: Pseudomonas fluorescens

<400> SEQUENCE: 58

```
Met Ser Ser Val Pro Val Phe Gln Asn Phe Ile Asn Gly Gln Phe Thr
1               5                   10                  15
His Ser Glu Ala His Leu Asp Val Tyr Asn Pro Ala Thr Gly Ala Leu
            20                  25                  30
Leu Ser Arg Val Pro Ala Ser Thr Cys Ala Asp Val Asp Gln Ala Leu
        35                  40                  45
Ala Gly Ala Arg Ala Ala Gln Lys Ala Trp Ser Ala Lys Pro Ala Ile
    50                  55                  60
Glu Arg Ala Gly Tyr Leu Arg Arg Ile Ala Ser Lys Leu Arg Glu Asn
65                  70                  75                  80
Val Ala His Leu Ala Arg Thr Ile Thr Leu Glu Gln Gly Lys Ile Ser
                85                  90                  95
Ala Leu Ala Glu Val Glu Val Asn Phe Thr Ala Asp Tyr Leu Asp Tyr
            100                 105                 110
Met Ala Glu Trp Ala Arg Arg Ile Glu Gly Glu Ile Thr Ser Asp
        115                 120                 125
Arg Pro Gly Glu Asn Ile Phe Leu Phe Arg Lys Pro Leu Gly Val Val
130                 135                 140
Ala Gly Ile Leu Pro Trp Asn Phe Pro Phe Phe Leu Ile Ala Arg Lys
145                 150                 155                 160
Met Ala Pro Ala Leu Leu Thr Gly Asn Thr Ile Val Ile Lys Pro Ser
                165                 170                 175
Glu Glu Thr Pro Asn Asn Cys Phe Glu Phe Ala Arg Leu Val Ala Glu
            180                 185                 190
Thr Asp Leu Pro Pro Gly Val Phe Asn Val Val Cys Gly Asp Gly Arg
        195                 200                 205
Val Gly Ala Ala Leu Ser Gly His Lys Gly Val Asp Met Ile Ser Phe
    210                 215                 220
Thr Gly Ser Val Asp Thr Gly Ser Arg Ile Met Thr Ala Ala Ala Thr
225                 230                 235                 240
Asn Ile Thr Lys Leu Asn Leu Glu Leu Gly Gly Lys Ala Pro Ala Ile
                245                 250                 255
Val Leu Ala Asp Ala Asp Leu Ala Leu Ala Val Lys Ala Ile Arg Asp
            260                 265                 270
Ser Arg Ile Ile Asn Thr Gly Gln Val Cys Asn Cys Ala Glu Arg Val
        275                 280                 285
Tyr Val Glu Arg Lys Val Ala Asp Gln Phe Ile Glu Arg Ile Ser Ala
    290                 295                 300
Ala Met Ser Ala Thr Arg Tyr Gly Asp Pro Leu Ala Glu Pro Asp Val
305                 310                 315                 320
Glu Met Gly Pro Leu Ile Asn Arg Gln Gly Leu Asp Ser Val Glu Arg
                325                 330                 335
Lys Val Arg Ile Ala Leu Gln Gln Gly Ala Ser Leu Ile Ser Gly Gly
            340                 345                 350
Arg Val Ala Asp Arg Pro Asp Gly Phe His Phe Glu Pro Thr Val Leu
        355                 360                 365
Ala Gly Cys Asn Ala Ser Met Asp Ile Met Arg Glu Glu Ile Phe Gly
    370                 375                 380
```

```
Pro Val Leu Pro Ile Gln Ile Val Asp Asp Leu Asp Glu Ala Ile Ala
385                 390                 395                 400

Leu Ala Asn Asp Cys Asp Tyr Gly Leu Thr Ser Ser Val Tyr Thr Arg
                405                 410                 415

Asp Leu Gly Arg Ala Met His Ala Ile Arg Gly Leu Asp Phe Gly Glu
            420                 425                 430

Thr Tyr Val Asn Arg Glu Asn Phe Glu Ala Met Gln Gly Phe His Ala
        435                 440                 445

Gly Val Arg Lys Ser Gly Val Gly Gly Ala Asp Gly Lys His Gly Leu
    450                 455                 460

Tyr Glu Tyr Thr His Thr His Ala Val Tyr Leu Gln Ser
465                 470                 475

<210> SEQ ID NO 59
<211> LENGTH: 1434
<212> TYPE: DNA
<213> ORGANISM: Artificial Sequence
<220> FEATURE:
<223> OTHER INFORMATION: Codon-adapted nucleotide sequence

<400> SEQUENCE: 59
atgtctcatg ctatatatca gaactatata gctaatgcat tgtagcatc agatgaacac        60 ttagaggtac acaatccagc gaatggacaa ttgcttgctc atgtacctca gggttcttct      120
gctgaagttg aaagggctat agctgctgca agacaagccc aaaaagcatg gctgctaga      180 ccagcaatag aaagggctgg atatttaaga aaaatagcat caaaaataag agaacacgga      240
gaaagattag cccgtataat aacagcagaa cagggaaaag ttttagaact ggcaagagtt      300
gaagtaaatt ttacagctga ttatttagac tacatggctg agtgggcaag aagattggaa      360
ggagaggtct tgagttcaga tagaccagga gaatctatat ttttgttaag aaaacctctt      420
ggagttgtcg ctggaatact tccttggaat tttccttttct tccttatagc tagaaaaatg      480
gctccagcac tgcttacagg aaatactata gttataaagc cttctgaaga gactcctata      540
aattgttttg aatttgcaag actggtagca gagacagatc ttccagcggg agtatttaat      600
gttgtatgtg gaactggagc gactgtagga atgctttaa ctagtcatcc tggaatagat       660
ttgataagct ttacaggctc agttggaaca ggaagtagaa taatggcagc agcagcacca      720
aatataacaa aattgaatct gaacttggc ggcaaggcac cagccattgt actagctgat      780
gctgatcttg atcttgcagt tagagcaata actgcatcaa gggtaatcaa tacaggtcag      840
gtatgtaact gtgctgaaag agtatacgtg gagagaaagg ttgcagatgc atttattgaa      900
aggattgctg cagcaatggc aggaactaga tatggtgatc cattagcaga aaatggttg       960 gatatgggtc cacttataaa tagggctgcg ttggacaaag ttgcacaaat ggtaagaact     1020
gcaagtggtc agggtgccca ggttataaca gccggcgcag ttgccgactt aggacaagga     1080
ttccactacc aacctacagt attagctggc tgctctgcag atatggaaat tatgagaaag     1140
gaaatatttg gtcctgtact tcctatacaa atagtagatg acttagatga ggctattgca     1200
ttatcaaatg attccgaata tggattaaca agctccatat ataccgccag cttaagtgca     1260
gctatgcagg ctacaagaag ccttgatttt ggagaaacct acataaatcg tgaaaacttt     1320
gaagcaatgc aaggttttca tgctggtaca agaaagtctg gcataggcgg cgctgacgga     1380
aagcacgggt tatatgaata tacgcatacc catgtagttt atatccaagc ataa          1434

<210> SEQ ID NO 60
```

-continued

```
<211> LENGTH: 477
<212> TYPE: PRT
<213> ORGANISM: Pseudomonas fluorescens

<400> SEQUENCE: 60

Met Ser His Ala Ile Tyr Gln Asn Tyr Ile Ala Asn Ala Phe Val Ala
1               5                   10                  15

Ser Asp Glu His Leu Glu Val His Asn Pro Ala Asn Gly Gln Leu Leu
            20                  25                  30

Ala His Val Pro Gln Gly Ser Ser Ala Glu Val Glu Ala Arg Ile Ala
        35                  40                  45

Ala Ala Arg Gln Ala Gln Lys Ala Trp Ala Ala Arg Pro Ala Ile Glu
    50                  55                  60

Arg Ala Gly Tyr Leu Arg Lys Ile Ala Ser Lys Ile Arg Glu His Gly
65                  70                  75                  80

Glu Arg Leu Ala Arg Ile Ile Thr Ala Glu Gln Gly Lys Val Leu Glu
                85                  90                  95

Leu Ala Arg Val Glu Val Asn Phe Thr Ala Asp Tyr Leu Asp Tyr Met
            100                 105                 110

Ala Glu Trp Ala Arg Arg Leu Glu Gly Glu Val Leu Ser Ser Asp Arg
        115                 120                 125

Pro Gly Glu Ser Ile Phe Leu Leu Arg Lys Pro Leu Gly Val Val Ala
    130                 135                 140

Gly Ile Leu Pro Trp Asn Phe Pro Phe Phe Leu Ile Ala Arg Lys Met
145                 150                 155                 160

Ala Pro Ala Leu Leu Thr Gly Asn Thr Ile Val Ile Lys Pro Ser Glu
                165                 170                 175

Glu Thr Pro Ile Asn Cys Phe Glu Phe Ala Arg Leu Val Ala Glu Thr
            180                 185                 190

Asp Leu Pro Ala Gly Val Phe Asn Val Val Cys Gly Thr Gly Ala Thr
        195                 200                 205

Val Gly Asn Ala Leu Thr Ser His Pro Gly Ile Asp Leu Ile Ser Phe
    210                 215                 220

Thr Gly Ser Val Gly Thr Gly Ser Arg Ile Met Ala Ala Ala Ala Pro
225                 230                 235                 240

Asn Ile Thr Lys Leu Asn Leu Glu Leu Gly Gly Lys Ala Pro Ala Ile
                245                 250                 255

Val Leu Ala Asp Ala Asp Leu Asp Leu Ala Val Arg Ala Ile Thr Ala
            260                 265                 270

Ser Arg Val Ile Asn Thr Gly Gln Val Cys Asn Cys Ala Glu Arg Val
        275                 280                 285

Tyr Val Glu Arg Lys Val Ala Asp Ala Phe Ile Glu Arg Ile Ala Ala
    290                 295                 300

Ala Met Ala Gly Thr Arg Tyr Gly Asp Pro Leu Ala Glu Asn Gly Leu
305                 310                 315                 320

Asp Met Gly Pro Leu Ile Asn Arg Ala Ala Leu Asp Lys Val Ala Gln
                325                 330                 335

Met Val Arg Thr Ala Ser Gly Gln Gly Ala Gln Val Ile Thr Gly Gly
            340                 345                 350

Ala Val Ala Asp Leu Gly Gln Gly Phe His Tyr Gln Pro Thr Val Leu
        355                 360                 365

Ala Gly Cys Ser Ala Asp Met Glu Ile Met Arg Lys Glu Ile Phe Gly
    370                 375                 380

Pro Val Leu Pro Ile Gln Ile Val Asp Asp Leu Asp Glu Ala Ile Ala
```

```
                385           390           395           400
Leu Ser Asn Asp Ser Glu Tyr Gly Leu Thr Ser Ser Ile Tyr Thr Ala
                405                   410                 415

Ser Leu Ser Ala Ala Met Gln Ala Thr Arg Ser Leu Asp Phe Gly Glu
            420                 425                 430

Thr Tyr Ile Asn Arg Glu Asn Phe Glu Ala Met Gln Gly Phe His Ala
                435                 440                 445

Gly Thr Arg Lys Ser Gly Ile Gly Gly Ala Asp Gly Lys His Gly Leu
        450                 455                 460

Tyr Glu Tyr Thr His Thr His Val Val Tyr Ile Gln Ala
465                 470                 475
```

<210> SEQ ID NO 61
<211> LENGTH: 1155
<212> TYPE: DNA
<213> ORGANISM: Artificial Sequence
<220> FEATURE:
<223> OTHER INFORMATION: Codon-adapted nucleotide sequence

<400> SEQUENCE: 61

```
atggccaaca gaatgatctt aaatgaaaca agttatattg gagcaggagc aatagaaaat      60
atagtggcag aggctaaggt tagaggttat aaaaaggctc ttgcagttac tgatagggac     120
cttattaaat ttaatgtagc aaccaaagtt acagatcttt taaaggcaaa caatcttgct     180
tttgaaatat ttgatgaagt aaaagcaaat cccactatta tgttgttttt agctggtatt     240
gaaaaattta aggcagcagg agcagattac ttattagcta taggcggcgg ctcgagtatc     300
gatacggcaa agcaatagg tattatagta agaaccctg aatttagtga tgttagatct     360
cttgaaggag ttgccgatac aaaaaataaa tgtgttgata ttatagctgt acctactact     420
gctggcacag cagctgaggt aactataaac tatgtaataa cagatgaaga aaaaagaga     480
aaatttgtct gtgttgatcc tcatgatata cctgtaatag ccgtagtaga ttcagaaatg     540
atgtcaagta tgccaaaagg actaacagca gcaacaggaa tggatgcact tacgcatgct     600
atagaaggat atataacaaa aggagcctgg gaacttacag atgcactaca tcttaaggct     660
atagaaataa ttggaagatc ccttagatca gcagttaata atgaaccaaa aggaagagaa     720
gatatggctt taggacaata cgtggcagga atgggattta gcaatgttgg tttgggaata     780
gtccatggta tggctcatcc tcttggagca ttctatgata ctcctcatgg tatagcaaat     840
gcagtactcc ttccttatgt tatggagtat aatgcagagg caacaggata caaatataga     900
gaaattgccc gtgcaatggg tgttcaaggt gtagactcaa tgagccagga tgaatacaga     960
aaagcggcta ttgatgctgt aaagaaatta agtgaagatg ttggtattcc taaggtatta    1020
aatgagattg gagtaaagga agaagattta caggctcttt ctgaatcagc atttgcagat    1080
gcttgtactc aggaaatcc tagagatact tctgttgaag aaatacttgc catatataag    1140
aaggcattca aataa                                                     1155
```

<210> SEQ ID NO 62
<211> LENGTH: 384
<212> TYPE: PRT
<213> ORGANISM: Clostridium saccharoperbutylacetonicum

<400> SEQUENCE: 62

```
Met Ala Asn Arg Met Ile Leu Asn Glu Thr Ser Tyr Ile Gly Ala Gly
1               5                   10                  15

Ala Ile Glu Asn Ile Val Ala Glu Ala Lys Val Arg Gly Tyr Lys Lys
```

```
            20                  25                  30
Ala Leu Ala Val Thr Asp Arg Asp Leu Ile Lys Phe Asn Val Ala Thr
            35                  40                  45

Lys Val Thr Asp Leu Leu Lys Ala Asn Asn Leu Ala Phe Glu Ile Phe
        50                  55                  60

Asp Glu Val Lys Ala Asn Pro Thr Ile Asn Val Val Leu Ala Gly Ile
65                  70                  75                  80

Glu Lys Phe Lys Ala Ala Gly Ala Asp Tyr Leu Leu Ala Ile Gly Gly
                85                  90                  95

Gly Ser Ser Ile Asp Thr Ala Lys Ala Ile Gly Ile Val Lys Asn
            100                 105                 110

Pro Glu Phe Ser Asp Val Arg Ser Leu Glu Gly Val Ala Asp Thr Lys
            115                 120                 125

Asn Lys Cys Val Asp Ile Ile Ala Val Pro Thr Thr Ala Gly Thr Ala
            130                 135                 140

Ala Glu Val Thr Ile Asn Tyr Val Ile Thr Asp Glu Glu Lys Lys Arg
145                 150                 155                 160

Lys Phe Val Cys Val Asp Pro His Asp Ile Pro Val Ile Ala Val Val
                165                 170                 175

Asp Ser Glu Met Met Ser Ser Met Pro Lys Gly Leu Thr Ala Ala Thr
            180                 185                 190

Gly Met Asp Ala Leu Thr His Ala Ile Glu Gly Tyr Ile Thr Lys Gly
            195                 200                 205

Ala Trp Glu Leu Thr Asp Ala Leu His Leu Lys Ala Ile Glu Ile Ile
            210                 215                 220

Gly Arg Ser Leu Arg Ser Ala Val Asn Asn Glu Pro Lys Gly Arg Glu
225                 230                 235                 240

Asp Met Ala Leu Gly Gln Tyr Val Ala Gly Met Gly Phe Ser Asn Val
                245                 250                 255

Gly Leu Gly Ile Val His Gly Met Ala His Pro Leu Gly Ala Phe Tyr
            260                 265                 270

Asp Thr Pro His Gly Ile Ala Asn Ala Val Leu Leu Pro Tyr Val Met
            275                 280                 285

Glu Tyr Asn Ala Glu Ala Thr Gly Tyr Lys Tyr Arg Glu Ile Ala Arg
            290                 295                 300

Ala Met Gly Val Gln Gly Val Asp Ser Met Ser Gln Asp Glu Tyr Arg
305                 310                 315                 320

Lys Ala Ala Ile Asp Ala Val Lys Lys Leu Ser Glu Asp Val Gly Ile
                325                 330                 335

Pro Lys Val Leu Asn Glu Ile Gly Val Lys Glu Asp Leu Gln Ala
            340                 345                 350

Leu Ser Glu Ser Ala Phe Ala Asp Ala Cys Thr Pro Gly Asn Pro Arg
            355                 360                 365

Asp Thr Ser Val Glu Glu Ile Leu Ala Ile Tyr Lys Lys Ala Phe Lys
            370                 375                 380

<210> SEQ ID NO 63
<211> LENGTH: 504
<212> TYPE: DNA
<213> ORGANISM: Artificial Sequence
<220> FEATURE:
<223> OTHER INFORMATION: Codon-adapted nucleotide sequence

<400> SEQUENCE: 63
atggtatcaa gtggagtttt ttctcttcat ctcaaactta taaacagaat attatcagct    60
```

```
ttagccgtat gtaaacaaat ttcccagata tttgatttag ctatagtggc tttagctgta      120
tgtgatggcg gcataatggc tggatctcat agaataaatg gaatggaaca tcctgtaagt      180
gatttatatg atgcagttca tggtaaggga ttggctgctt taactcctat aatagttgaa      240
aaatcctgga aaagtgatat agaaaaatat gatgatataa gcaaattgat tggatgttca      300
tcagcaaaaa attgtgcaga tgctatacgg tcattccttg aaaagataaa tctaaacgta      360
acccttggtg aattaggtgt taaagaaaaa gatgtagaat ggatgtcaga aaattgcatg      420
aaagtgtcaa aaccttccat aattaatcac ccaagggaat ttactctaga gaaaattaag      480
aacatttatt atgaagaatt ataa                                            504
```

<210> SEQ ID NO 64
<211> LENGTH: 167
<212> TYPE: PRT
<213> ORGANISM: Clostridium ljungdahlii

<400> SEQUENCE: 64

```
Met Val Ser Ser Gly Val Phe Ser Leu His Leu Lys Leu Ile Asn Arg
1               5                   10                  15

Ile Leu Ser Ala Leu Ala Val Cys Lys Gln Ile Ser Gln Ile Phe Asp
            20                  25                  30

Leu Ala Ile Val Ala Leu Ala Val Cys Asp Gly Gly Ile Met Ala Gly
        35                  40                  45

Ser His Arg Ile Asn Gly Met Glu His Pro Val Ser Asp Leu Tyr Asp
    50                  55                  60

Ala Val His Gly Lys Gly Leu Ala Ala Leu Thr Pro Ile Ile Val Glu
65                  70                  75                  80

Lys Ser Trp Lys Ser Asp Ile Glu Lys Tyr Asp Asp Ile Ser Lys Leu
                85                  90                  95

Ile Gly Cys Ser Ser Ala Lys Asn Cys Ala Asp Ala Ile Arg Ser Phe
            100                 105                 110

Leu Glu Lys Ile Asn Leu Asn Val Thr Leu Gly Glu Leu Gly Val Lys
        115                 120                 125

Glu Lys Asp Val Glu Trp Met Ser Glu Asn Cys Met Lys Val Ser Lys
    130                 135                 140

Pro Ser Ile Ile Asn His Pro Arg Glu Phe Thr Leu Glu Lys Ile Lys
145                 150                 155                 160

Asn Ile Tyr Tyr Glu Glu Leu
                165
```

<210> SEQ ID NO 65
<211> LENGTH: 1149
<212> TYPE: DNA
<213> ORGANISM: Artificial Sequence
<220> FEATURE:
<223> OTHER INFORMATION: Codon-adapted nucleotide sequence

<400> SEQUENCE: 65

```
atggcaaata gaatgatatt aaatgaaaca gcatggtttg aagagggggc tgtaggtgca       60
ctaacagatg aagtaaagag aagaggatat cagaaggctt taatagtaac tgataagacg      120
cttgtacaat gtggtgtagt tgctaaagta acagataaaa tggatgctgc aggacttgca      180
tgggctattt atgatggtgt agtccctaat cctactataa ctgtagtaaa agagggcctt      240
ggagtatttc aaaattcagg tgcagattat ttgatagcta taggcggcgg ctctcctcaa      300
gatacttgta aagccattgg aataattagc aacaatcctg aatttgccga cgttagatca      360
```

-continued

```
cttgaaggat tatctcctac aaataaacca agcgtaccta tacttgcaat acctactaca    420
gcgggtactg cagctgaagt tacaataaac tatgtaatta cagacgaaga aaagagaaga    480
aaatttgtat gtgtagaccc tcatgacata cctcaagtag catttattga tgcagacatg    540
atggatggaa tgccccctgc tttaaaagca gcaactggtg tagatgcatt gacccatgct    600
atagaaggat atattactcg cggggcatgg gctttaaccg atgcactgca tataaaggct    660
atagaaataa tagctgggc attgagaggt tctgtagctg gtgacaaaga tgctggtgaa    720
gagatggcgt taggtcagta tgtagcggga atgggattt caaatgtagg gttaggatta    780
gttcacggga tggctcatcc tttaggtgca ttctataata caccacatgg agtagctaat    840
gctatactac taccacatgt tatgagatat aatgcagatt ttaccggaga aaaatataga    900
gatatagcac gagttatggg tgtaaaagta gaaggaatga gcttagaaga ggctagaaat    960
gcagcagtag aagcagtatt tgctttaaat agagatgtag gaataccacc acatttaaga   1020
gatgttggtg taagaaaaga ggatattcca gcactggcac aggcagcatt ggatgatgta   1080
tgtacaggcg gcaatccaag agaggctaca cttgaagata tagtagagct ttatcatact   1140
gcatggtaa                                                           1149
```

<210> SEQ ID NO 66
<211> LENGTH: 382
<212> TYPE: PRT
<213> ORGANISM: Escherichia coli

<400> SEQUENCE: 66

```
Met Ala Asn Arg Met Ile Leu Asn Glu Thr Ala Trp Phe Gly Arg Gly
  1               5                  10                  15

Ala Val Gly Ala Leu Thr Asp Glu Val Lys Arg Arg Gly Tyr Gln Lys
             20                  25                  30

Ala Leu Ile Val Thr Asp Lys Thr Leu Val Gln Cys Gly Val Val Ala
         35                  40                  45

Lys Val Thr Asp Lys Met Asp Ala Ala Gly Leu Ala Trp Ala Ile Tyr
     50                  55                  60

Asp Gly Val Val Pro Asn Pro Thr Ile Thr Val Lys Glu Gly Leu
 65                  70                  75                  80

Gly Val Phe Gln Asn Ser Gly Ala Asp Tyr Leu Ile Ala Ile Gly Gly
                 85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
    210                 215                 220
```

```
Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
            245                 250                 255

Gly Leu Gly Leu Val His Gly Met Ala His Pro Leu Gly Ala Phe Tyr
        260                 265                 270

Asn Thr Pro His Gly Val Ala Asn Ala Ile Leu Leu Pro His Val Met
    275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
            325                 330                 335

Pro His Leu Arg Asp Val Gly Val Arg Lys Glu Asp Ile Pro Ala Leu
        340                 345                 350

Ala Gln Ala Ala Leu Asp Asp Val Cys Thr Gly Asn Pro Arg Glu
    355                 360                 365

Ala Thr Leu Glu Asp Ile Val Glu Leu Tyr His Thr Ala Trp
370                 375                 380
```

<210> SEQ ID NO 67
<211> LENGTH: 1155
<212> TYPE: DNA
<213> ORGANISM: Artificial Sequence
<220> FEATURE:
<223> OTHER INFORMATION: Codon-adapted nucleotide sequence

<400> SEQUENCE: 67

| | | | | | |
|---|---|---|---|---|---|
| atgacaaata | gaatgatatt | aaatgaaact | agttatatag | gtgctggagc | aatagaaaac | 60 |
| atagtaacag | aggcaaaaac | acgaggttat | aaaaaggcac | ttgttgtaac | agataaagaa | 120 |
| ttaattaaat | ttaatgttgc | cagcaaagta | accaatttgt | taaataaaaa | tgatctaata | 180 |
| tttgagattt | ttgatgaagt | aaaagcaaat | ccaactataa | atgtagtatt | agctggtata | 240 |
| gaaagattta | aggcttcagg | agcagattat | cttatagcta | taggcggcgg | ctcttcaata | 300 |
| gatactgcta | aagcaattgg | tataataata | aataatccag | aatttagtga | tgttagatca | 360 |
| cttgaaggtg | ctgtagaaac | aaaaaaataaa | tgtgtagata | taatagcagt | tccaactaca | 420 |
| gcaggcactg | ctgctgaagt | aactataaat | tatgttataa | cagatgaaga | agaaagaga | 480 |
| aaatttgtat | gtgttgatcc | tcatgatatt | ccagttattg | cagtagtaga | tagtgagatg | 540 |
| atgtcaagca | tgcctaaggg | attaacagct | gcaactggaa | tggatgcttt | aactcatgct | 600 |
| atagaaggat | atattacaaa | aggagcatgg | gaactaacag | atactctaca | tttaaaggct | 660 |
| attgaaataa | taggaagaag | cttaaggtca | gctgtaaata | tgaacctaa | aggaagagaa | 720 |
| gatatggcat | taggacaata | tatagcagga | atgggttttt | ccaatgttgg | attgggaata | 780 |
| gttcattcta | tggcgcaccc | attgggtgct | ttttatgata | ctcttcacgg | aatagcaaat | 840 |
| gctgtacttt | taccttatgt | aatggagtat | aatgcagagg | ctactgatga | aaagtacagg | 900 |
| gaaatagcga | gagtaatggg | tgtagaaggt | gtagataaca | tgtctcaaaa | agaatacaga | 960 |
| aaggctgcaa | ttgatgctgt | taaaaagctc | tccgaagatg | taggtatacc | aaaggtactt | 1020 |
| aatgaaatcg | gagtaaaaga | gaggatcttt | caatctttag | cagaatcagc | ctttgtagat | 1080 |
| gcatgcacgc | ctggtaaccc | aagggatact | tcagttgtag | aaatactgga | aatatataaa | 1140 |
| aaggcattca | aataa | | | | | 1155 |

<210> SEQ ID NO 68
<211> LENGTH: 384
<212> TYPE: PRT
<213> ORGANISM: Clostridium beijerinckii

<400> SEQUENCE: 68

```
Met Thr Asn Arg Met Ile Leu Asn Glu Thr Ser Tyr Ile Gly Ala Gly
1               5                   10                  15

Ala Ile Glu Asn Ile Val Thr Glu Ala Lys Thr Arg Gly Tyr Lys Lys
                20                  25                  30

Ala Leu Val Val Thr Asp Lys Glu Leu Ile Lys Phe Asn Val Ala Ser
            35                  40                  45

Lys Val Thr Asn Leu Leu Asn Lys Asn Asp Leu Ile Phe Glu Ile Phe
50                  55                  60

Asp Glu Val Lys Ala Asn Pro Thr Ile Asn Val Val Leu Ala Gly Ile
65                  70                  75                  80

Glu Arg Phe Lys Ala Ser Gly Ala Asp Tyr Leu Ile Ala Ile Gly Gly
                85                  90                  95

Gly Ser Ser Ile Asp Thr Ala Lys Ala Ile Gly Ile Ile Asn Asn
                100                 105                 110

Pro Glu Phe Ser Asp Val Arg Ser Leu Glu Gly Ala Val Glu Thr Lys
            115                 120                 125

Asn Lys Cys Val Asp Ile Ile Ala Val Pro Thr Thr Ala Gly Thr Ala
130                 135                 140

Ala Glu Val Thr Ile Asn Tyr Val Ile Thr Asp Glu Glu Arg Lys Arg
145                 150                 155                 160

Lys Phe Val Cys Val Asp Pro His Asp Ile Pro Val Ile Ala Val Val
                165                 170                 175

Asp Ser Glu Met Met Ser Ser Met Pro Lys Gly Leu Thr Ala Ala Thr
            180                 185                 190

Gly Met Asp Ala Leu Thr His Ala Ile Glu Gly Tyr Ile Thr Lys Gly
        195                 200                 205

Ala Trp Glu Leu Thr Asp Thr Leu His Leu Lys Ala Ile Glu Ile Ile
210                 215                 220

Gly Arg Ser Leu Arg Ser Ala Val Asn Asn Glu Pro Lys Gly Arg Glu
225                 230                 235                 240

Asp Met Ala Leu Gly Gln Tyr Ile Ala Gly Met Gly Phe Ser Asn Val
                245                 250                 255

Gly Leu Gly Ile Val His Ser Met Ala His Pro Leu Gly Ala Phe Tyr
            260                 265                 270

Asp Thr Leu His Gly Ile Ala Asn Ala Val Leu Leu Pro Tyr Val Met
        275                 280                 285

Glu Tyr Asn Ala Glu Ala Thr Asp Glu Lys Tyr Arg Glu Ile Ala Arg
290                 295                 300

Val Met Gly Val Glu Gly Val Asp Asn Met Ser Gln Lys Glu Tyr Arg
305                 310                 315                 320

Lys Ala Ala Ile Asp Ala Val Lys Leu Ser Glu Asp Val Gly Ile
                325                 330                 335

Pro Lys Val Leu Asn Glu Ile Gly Val Lys Glu Asp Leu Gln Ser
            340                 345                 350

Leu Ala Glu Ser Ala Phe Val Asp Ala Cys Thr Pro Gly Asn Pro Arg
        355                 360                 365

Asp Thr Ser Val Val Glu Ile Leu Glu Ile Tyr Lys Lys Ala Phe Lys
```

<210> SEQ ID NO 69
<211> LENGTH: 37
<212> TYPE: DNA
<213> ORGANISM: Artificial Sequence
<220> FEATURE:
<223> OTHER INFORMATION: Synthetic oligo

<400> SEQUENCE: 69
cacaccaggt ctcaaaccat ggagatctcg aggcctg                37

<210> SEQ ID NO 70
<211> LENGTH: 37
<212> TYPE: DNA
<213> ORGANISM: Artificial Sequence
<220> FEATURE:
<223> OTHER INFORMATION: Synthetic oligo

<400> SEQUENCE: 70
cacaccaggt ctcacatatg ataagaagac tcttggc                37

<210> SEQ ID NO 71
<211> LENGTH: 36
<212> TYPE: DNA
<213> ORGANISM: Artificial Sequence
<220> FEATURE:
<223> OTHER INFORMATION: Synthetic oligo

<400> SEQUENCE: 71
cacaccaggt ctcacatatg acagcaacaa ggggcc                 36

<210> SEQ ID NO 72
<211> LENGTH: 69
<212> TYPE: DNA
<213> ORGANISM: Artificial Sequence
<220> FEATURE:
<223> OTHER INFORMATION: Synthetic oligo

<400> SEQUENCE: 72
cacaccaggt ctcaattgta acacctcctt aattagttat gctctttctt ctataggtac    60
aaatttttg                                                           69

<210> SEQ ID NO 73
<211> LENGTH: 41
<212> TYPE: DNA
<213> ORGANISM: Artificial Sequence
<220> FEATURE:
<223> OTHER INFORMATION: Synthetic oligo

<400> SEQUENCE: 73
cacaccaggt ctcacaatga aaacaagaac tcaacaaata g           41

<210> SEQ ID NO 74
<211> LENGTH: 62
<212> TYPE: DNA
<213> ORGANISM: Artificial Sequence
<220> FEATURE:
<223> OTHER INFORMATION: Synthetic oligo

<400> SEQUENCE: 74
cacaccaggt ctcagtgttc ctcctatgtg ttcttaaaat tgagattctt cagttgaacc    60
tg                                                                  62

<210> SEQ ID NO 75
<211> LENGTH: 62
<212> TYPE: DNA
<213> ORGANISM: Artificial Sequence
<220> FEATURE:
<223> OTHER INFORMATION: Synthetic oligo

<400> SEQUENCE: 75
cacaccaggt ctcagtgttc ctcctatgtg ttcttaaaat tgagattctt cagttgaacc    60
tg    62

<210> SEQ ID NO 76
<211> LENGTH: 50
<212> TYPE: DNA
<213> ORGANISM: Artificial Sequence
<220> FEATURE:
<223> OTHER INFORMATION: Synthetic oligo

<400> SEQUENCE: 76
cacaccaggt ctcaggttat gcatttagat atattgtttt tgtctgtacg    50

<210> SEQ ID NO 77
<211> LENGTH: 44
<212> TYPE: DNA
<213> ORGANISM: Artificial Sequence
<220> FEATURE:
<223> OTHER INFORMATION: Synthetic oligo

<400> SEQUENCE: 77
cacaccaggt ctcacatatg caatttaggc cttttaatcc acca    44

<210> SEQ ID NO 78
<211> LENGTH: 53
<212> TYPE: DNA
<213> ORGANISM: Artificial Sequence
<220> FEATURE:
<223> OTHER INFORMATION: Synthetic oligo

<400> SEQUENCE: 78
cacaccaggt ctcagtgttc ctcctatgtg ttcttatgct tgcgcaagtg cct    53

<210> SEQ ID NO 79
<211> LENGTH: 44
<212> TYPE: DNA
<213> ORGANISM: Artificial Sequence
<220> FEATURE:
<223> OTHER INFORMATION: Synthetic oligo

<400> SEQUENCE: 79
cacaccaggt ctcaacacat atgtcttcag tgcctgtatt ccag    44

<210> SEQ ID NO 80
<211> LENGTH: 42
<212> TYPE: DNA
<213> ORGANISM: Artificial Sequence
<220> FEATURE:
<223> OTHER INFORMATION: Synthetic oligo

<400> SEQUENCE: 80
cacaccaggt ctcaggttaa gactggagat atactgcatg ag    42

<210> SEQ ID NO 81
<211> LENGTH: 40
<212> TYPE: DNA
<213> ORGANISM: Artificial Sequence
<220> FEATURE:

```
<223> OTHER INFORMATION: Synthetic oligo

<400> SEQUENCE: 81
cacaccaggt ctcacatatg agaactccat ttattatgac                           40

<210> SEQ ID NO 82
<211> LENGTH: 52
<212> TYPE: DNA
<213> ORGANISM: Artificial Sequence
<220> FEATURE:
<223> OTHER INFORMATION: Synthetic oligo

<400> SEQUENCE: 82
cacaccaggt ctcagtgttc ctcctatgtg ttcctaatct acaaagtgct tg             52
```

MICROORGANISMS AND METHODS FOR THE BIOLOGICAL PRODUCTION OF ETHYLENE GLYCOL

BACKGROUND OF THE INVENTION

Field of the Invention

The present invention relates to genetically engineered microorganisms and methods for the production of ethylene glycol and ethylene glycol precursors by microbial fermentation, particularly by microbial fermentation of a gaseous substrate.

Description of Related Art

Ethylene glycol, also known as monoethylene glycol (MEG), has a current market value of over $33 billion USD and is an important component of a huge variety of industrial, medical, and consumer products. Ethylene glycol is currently produced using chemical catalysis processes that require large amounts of energy and water, generate a number of undesirable by-products, and rely on petrochemical feedstocks. Demand for sustainable materials has led to some technological advancements, such as the catalytic production of ethylene glycol from sugar-cane derived ethanol.

Ethylene glycol precursors are also commercially valuable. For example, glycolate is used in skin care, personal care, dyeing, tanning, and as a cleaning agent. Glyoxylate is an intermediate for vanillin, agricultural chemicals, antibiotics, allantoin, and complexing agents.

However, no microorganisms are known to be capable of biologically producing ethylene glycol, and no fully biological route to the production of ethylene glycol has been well-established. Some biological routes to ethylene glycol have been described in the literature from sugars. For example, Alkim et al., *Microb Cell Fact*, 14: 127, 2015 demonstrated ethylene glycol production from (D)-xylose in *E. coli* but noted that aerobic conditions were required to achieve high yields. Similarly, Pereira et al., *Metab Eng*, 34: 80-87, 2016 achieved ethylene glycol production from pentoses in *E. coli*. A few studies on ethylene glycol production from pentoses have also been conducted in *S. cerevisiae* but have shown inconsistent results. See, e.g., Uranukul et al., *Metab Eng*, 51: 20-31, 2018.

Gas fermentation offers a route to use a wide range of readily available, low cost C1 feedstocks such as industrial waste gases, syngas, or reformed methane into chemicals and fuels. Since gas fermentation metabolism is significantly different from sugar-fermenting metabolism, use of the above-mentioned routes is not practical, as these routes would require production of sugar precursors from gas via gluconeogenesis, an energy negative process. To date, no route to produce ethylene glycol from gaseous substrates is available.

In an explorative exercise, Islam et al., *Metab Eng*, 41: 173-181, 2017 predicted hundreds of hypothetical pathways for producing ethylene glycol from syngas in *M. thermoacetia* using cheminformatics tools. However, it is not possible even for a skilled person in the art to incorporate these pathways in a gas fermenting organism, as many of the pathways are infeasible either due to thermodynamic or other constraints. For example, nearly 2,000 oxygen or oxygen radical-dependent reactions were included in Islam et al., which would not be feasible in a strictly anaerobic system. The only identified hypothetical pathways by Islam et al. that have known reactions require gluconeogenesis or ethanol as an intermediate. Therefore, there remains a need for validated, energetically favorable recombinant production systems that can produce high yields of ethylene glycol and ethylene glycol precursors from gaseous substrates.

SUMMARY OF THE INVENTION

It is against the above background that the present invention provides certain advantages and advancements over the prior art.

Although this invention disclosed herein is not limited to specific advantages or functionalities, the invention provides a genetically engineered microorganism capable of producing ethylene glycol or a precursor of ethylene glycol from a gaseous substrate.

In some aspects of the microorganism disclosed herein, the microorganism produces ethylene glycol or the precursor of ethylene glycol through one or more intermediates selected from the group consisting of 5,10-methylenetetrahydrofolate, oxaloacetate, citrate, malate, and glycine.

In some aspects of the microorganism disclosed herein, the microorganism comprises one or more of a heterologous enzyme capable of converting oxaloacetate to citrate, a heterologous enzyme capable of converting glycine to glyoxylate, a heterologous enzyme capable of converting iso-citrate to glyoxylate, and a heterologous enzyme capable of converting glycolate to glycoaldehyde.

In some aspects of the microorganism disclosed herein, the heterologous enzyme capable of converting oxaloacetate to citrate is a citrate [Si]-synthase [2.3.3.1], an ATP citrate synthase [2.3.3.8]; or a citrate (Re)-synthase [2.3.3.3]; the heterologous enzyme capable of converting glycine to glyoxylate is an alanine-glyoxylate transaminase [2.6.1.44], a serine-glyoxylate transaminase [2.6.1.45], a serine-pyruvate transaminase [2.6.1.51], a glycine-oxaloacetate transaminase [2.6.1.35], a glycine transaminase [2.6.1.4], a glycine dehydrogenase [1.4.1.10], an alanine dehydrogenase [1.4.1.1], or a glycine dehydrogenase [1.4.2.1]; the heterologous enzyme capable of converting iso-citrate to glyoxylate is an isocitrate lyase [4.1.3.1]; and/or the heterologous enzyme capable of converting glycolate to glycoaldehyde is a glycolaldehyde dehydrogenase [1.2.1.21], a lactaldehyde dehydrogenase [1.2.1.22], a succinate-semialdehyde dehydrogenase [1.2.1.24], a 2,5-dioxovalerate dehydrogenase [1.2.1.26], an aldehyde dehydrogenase [1.2.1.3/4/5], a betaine-aldehyde dehydrogenase [1.2.1.8], or an aldehyde ferredoxin oxidoreductase [1.2.7.5].

In some aspects of the microorganism disclosed herein, the heterologous enzymes are derived from a genus selected from the group consisting of *Bacillus, Clostridium, Escherichia, Gluconohacter, Hyphomicrobium, Lysinibacillus, Paenibacillus, Pseudomonas, Sedimenticola, Sporosarcina, Streptomyces, Thermithiobacillus, Thermotoga*, and *Zea*.

In some aspects of the microorganism disclosed herein, one or more of the heterologous enzymes are codon-optimized for expression in the microorganism.

In some aspects of the microorganism disclosed herein, the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phosphonooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycoaldehyde; and/or an enzyme capable of converting glycoaldehyde to ethylene glycol.

In some aspects of the microorganism disclosed herein, the microorganism overexpresses the heterologous enzyme capable of converting oxaloacetate to citrate, the heterologous enzyme capable of converting glycine to glyoxylate, and/or the heterologous enzyme capable of converting glycolate to glycoaldehyde.

In some aspects of the microorganism disclosed herein, the microorganism overexpresses the enzyme capable of converting pyruvate to oxaloacetate, the enzyme capable of converting citrate to aconitate and aconitate to iso-citrate, the enzyme capable of converting phosphoenolpyruvate to oxaloacetate, the enzyme capable of converting serine to glycine, the enzyme capable of converting 5,10-methylenetetrahydrofolate to glycine, the enzyme capable of converting glyoxylate to glycolate; and/or the enzyme capable of converting glycoaldehyde to ethylene glycol.

In some aspects of the microorganism disclosed herein, the microorganism comprises a disruptive mutation in one or more enzymes selected from the group consisting of isocitrate dehydrogenase, glycerate dehydrogenase, glycolate dehydrogenase, glycerate dehydrogenase, glycolate dehydrogenase, aldehyde ferredoxin oxidoreductase, and aldehyde dehydrogenase In some aspects of the microorganism disclosed herein, the microorganism is a member of a genus selected from the group consisting of *Acetobacterium, Alkalibaculum, Blautia, Butyribacterium, Clostridium, Eubacterium, Moorella, Oxobacter, Sporomusa,* and *Thermoanaerobacter.*

In some aspects of the microorganism disclosed herein, the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi.*

In some aspects of the microoiganism disclosed herein, the microorganism is derived from a parental bacterium selected from the group consisting of *Clostridium autoethanogenum, Clostridium ljungdahlii,* and *Clostridium ragsdalei.*

In some aspects of the microorganism disclosed herein, the microorganism comprises a native or heterologous Wood-Ljungdahl pathway.

In some aspects of the microorganism disclosed herein, the microorganism produces glyoxylate or glycolate as a precursor of ethylene glycol.

The invention further provides a method of producing ethylene glycol or a precursor of ethylene glycol comprising culturing the microorganism disclosed herein in a nutrient medium and in the presence of a substrate, whereby the microorganism produces ethylene glycol or the precursor of ethylene glycol.

In some aspects of the method disclosed herein, the substrate comprises one or more of CO, $CO_2$, and $H_2$.

In some aspects of the method disclosed herein, at least a portion of the substrate is industrial waste gas, industrial off gas, or syngas.

In some aspects of the method disclosed herein, the microorganism produces glyoxylate or glycolate as precursors of ethylene glycol.

In some aspects of the method disclosed herein, the method further comprises separating the ethylene glycol or the ethylene glycol precursor from the nutrient medium.

In some aspects of the method disclosed herein, the microorganism further produces one or more of ethanol, 2,3-butanediol, and succinate.

The invention further provides a composition comprising ethylene glycol produced by the method described herein. In some aspects, the composition is an antifreeze, a preservative, a dehydrating agent, or a drilling fluid.

The invention further provides a polymer comprising ethylene glycol produced by the method described herein. In some aspects, the polymer is a homopolymer or a copolymer. In some aspects, the polymer is polyethylene glycol or polyethylene terephthalate.

The invention further provides a composition comprising the polymer described herein. In some aspects, the composition is a fiber, a resin, a film, or a plastic.

These and other features and advantages of the present invention will be more fully understood from the following detailed description taken together with the accompanying claims. It is noted that the scope of the claims is defined by the recitations therein and not by the specific discussion of features and advantages set forth in the present description.

DESCRIPTION OF THE DRAWINGS

The following detailed description of the embodiments of the present invention can be best understood when read in conjunction with the following drawings, where like structure is indicated with like reference numerals and in which:

FIG. 2A is a map of expression shuttle vector, pIPL12, as described in Example 1. FIG. 2B is a map of plasmid pMEG042, which comprises *B. subtilis* citrate synthase, *E. coli* isocitrate lyase, and *G. oxydans* glycolaldehyde dehydrogenase, as described in Example 1. FIG. 2C is a map of plasmid pMEG058, which comprises *S. thiotaurini* alanine-glyoxylate aminotransferase and *P. fluorescens* aldehyde dehydrogenase, as described in Example 2. FIG. 2D is a map of plasmid pMEG059, which comprises *S. thiotaurini* alanine-glyoxylate aminotransferase and *G. oxydans* aldehyde dehydrogenase, as described in Example 3. FIG. 2E is a map of plasmid pMEG061, which comprises *C. acidurici* class V aminotransferase and *P. fluorescens* aldehyde dehydrogenase, as described in Example 4.

DETAILED DESCRIPTION OF THE INVENTION

Figure 1:
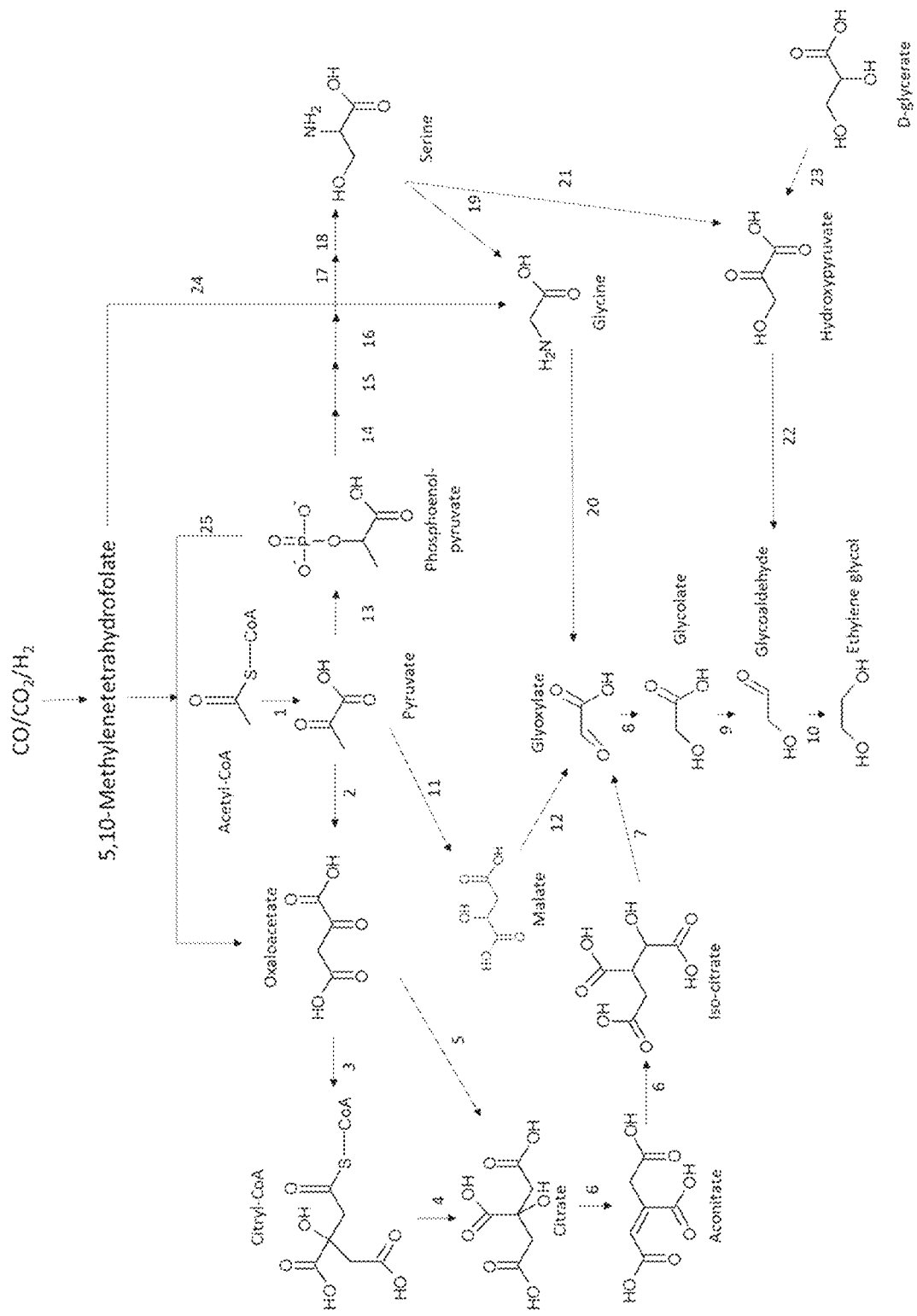
FIG. 1 is a schematic showing pathways for the production of ethylene glycol, glycolate, and glyoxylate from a gaseous substrate comprising CO, $CO_2$, and/or $H_2$.

The invention provides microorganisms for the biological production of ethylene glycol. A "microorganism" is a microscopic organism, especially a bacterium, archaeon, virus, or fungus. In a preferred embodiment, the microorganism of the invention is a bacterium.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility. The microorganisms of the invention are non-naturally occurring.

The terms "genetic modification," "genetic alteration." or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization. The microorganisms of the invention are genetically engineered.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. The microorganisms of the invention are generally recombinant.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that originates outside the microorganism of the invention. For example, an exogenous gene or enzyme may be artificially or recombinantly created and introduced to or expressed in the microorganism of the invention. An exogenous gene or enzyme may also be isolated from a heterologous microorganism and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Heterologous" refers to a nucleic acid or protein that is not present in the wild-type or parental microorganism from which the microorganism of the invention is derived. For example, a heterologous gene or enzyme may be derived from a different strain or species and introduced to or expressed in the microorganism of the invention. The heterologous gene or enzyme may be introduced to or expressed in the microorganism of the invention in the form in which it occurs in the different strain or species. Alternatively, the heterologous gene or enzyme may be modified in some way, e.g., by codon-optimizing it for expression in the microorganism of the invention or by engineering it to alter function, such as to reverse the direction of enzyme activity or to alter substrate specificity.

In particular, a heterologous nucleic acid or protein expressed in the microorganism described herein may be derived from *Bacillus, Clostridium, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, Zea, Klebsiella, Mycobacterium, Salmonella, Mycobacteroides, Staphylococcus, Burkholderia, Listeria, Acinetobacter, Shigella, Neisseria, Bordetella, Streptococcus, Enterobacter, Vibrio, Legionella, Xanthomonas, Serratia, Cronobacter, Cupriavidus, Helicobacter, Yersinia, Cutibacterium, Francisella, Pectobacterium, Arcobacter, Lactobacillus, Shewanella, Erwinia, Sulfiurospirillum, Peptococcaceae, Thermococcus, Saccharomyces, Pyrococcus, Glycine, Homo, Ralstonia, Brevibacterium, Methylobacterium, Geobacillus, bos, gallus, Anaerococcus, Xenopus, Amblvrhvnchus, rattus, mus, sus, Rhodococcus, Rhizobium, Megasphaera, Mesorhizobium, Peptococcus, Agrobacterium, Campylobacter, Acetobacierium, Alkalibaculum, Blautia, Butvribacterium, Eubacterium, Moorella, Oxobacter, Sporomusa, Thermoanaerobacter, Schizosaccharomyces, Paenibacillus, Fictibacillus, Lysinibacillus, Ornithinibacillus, Halobacillus, Kurthia, Lentibacillus, Anoxybacillus, Solibacillus, Virgibacillus, Ali-*

*cyclobacillus*, *Sporosarcina*, *Salimicrobium*, *Sporosarcina*, *Planococcus*, *Corynebacterium*, *Thermaerobacter*, *Sulfobacillus*, or *Symbiobacterium*.

The terms "polynucleotide." "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof.

Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, by disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism.

The microorganism of the invention may be derived from essentially any parental microorganism. In one embodiment, the microorganism of the invention may be derived from a parental microorganism selected from the group consisting of *Clostridium acetobutylicum*, *Clostridium beijerinckii*, *Escherichia coli*, and *Saccharomyces cerevisiae*. In other embodiments, the microorganism is derived from a parental microorganism selected from the group consisting of *Acetobacterium woodii*, *Alkalibaculum bacchii*, *Blautia product*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, and *Thermoanaerobacter kiuvi*. In a preferred embodiment, the parental microorganism is *Clostridium autoethanogenum*, *Clostridium ljungdahlii*, or *Clostridium ragsdalei*. In an especially preferred embodiment, the parental microorganism is *Clostridium autoethanogenum* LZ1561, which was deposited on Jun. 7, 2010 with Deutsche Sammlung von Mikroorganismen und Zellkulturen GmbH (DSMZ) located at Inhoffenstraß 7B, D-38124 Braunschwieg, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlit*, or *Clostridium ragsdalei*. In a preferred embodiment, the microorganism of the invention is derived from *Clostridium autoethanogenum* LZ1561, which is deposited under DSMZ accession number DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph.

Table 1 provides a representative list of microorganisms and identifies their functional characteristics.

TABLE 1

| | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kiuvi* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Often, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO. $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Often, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen), sometimes referred to as "microoxic conditions." Often, the microorganism of the invention is an anaerobe. In a preferred embodiment, the microorganism of the invention is derived from an anaerobe identified in Table 1.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York. N.Y., 2006). All naturally occurring acetogens are C1-fixing, anaerobic, autotrophic, and non-methanotrophic. Often, the microorganism of the invention is an acetogen. In a preferred embodiment, the microorganism of the invention is derived from an acetogen identified in Table 1.

An "ethanologen" is a microorganism that produces or is capable of producing ethanol. Often, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Often, the microorganism of the invention is an autotroph. In a preferred embodiment, the microorganism of the invention is derived from an autotroph identified in Table 1.

A "carboxydotroph" is a microorganism capable of utilizing CO as a sole source of carbon and energy. Often, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JAI-1 (DSM10061) (Abrini, *Arch Microbiol*, 161: 345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

As described above, however, the microorganism of the invention may also be derived from essentially any parental microorganism, such as a parental microorganism selected from the group consisting of *Clostridium acetobutylicum*, *Clostridium beijerinckii*, *Escherichia coli*, and *Saccharomyces cerevisiae*.

The invention provides microorganisms capable of producing ethylene glycol, glyoxylate, and glycolate as well as methods of producing ethylene glycol, glyoxylate, and glycolate comprising culturing the microorganism of the invention in the presence of a substrate, whereby the microorganism produces ethylene glycol.

A microorganism of the invention may comprise an enzyme that converts acetyl-CoA, such as acetyl-CoA produced by the Wood-Ljungdahl pathway, to pyruvate (reaction 1 of FIG. 1). This enzyme may be a pyruvate synthase (PFOR) [1.2.7.1] or an ATP:pyruvate, orthophosphate phosphotransferase [1.2.7.1]. In some embodiments, the enzyme that converts acetyl-CoA to pyruvate is an endogenous enzyme.

A microorganism of the invention may comprise an enzyme that converts pyruvate to oxaloacetate (reaction 2 of FIG. 1). This enzyme may be a pyruvate:carbon-dioxide ligase [ADP-forming] [6.4.1.1]. In some embodiments, the enzyme that converts pyruvate to oxaloacetate is an endogenous enzyme. In some embodiments, the enzyme that converts pyruvate to oxaloacetate is overexpressed.

A microorganism of the invention may comprise an enzyme that converts oxaloacetate to citryl-CoA (reaction 3 of FIG. 1). This enzyme may be a citryl-CoA lyase [4.1.3.34]. In some embodiments, the enzyme that converts oxaloacetate to citryl-CoA is an endogenous enzyme.

A microorganism of the invention may comprise an enzyme that converts citryl-CoA to citrate (reaction 4 of FIG. 1). This enzyme may be a citrate-CoA transferase [2.8.3.10]. In some embodiments, the enzyme that converts citryl-CoA to citrate is an endogenous enzyme.

A microorganism of the invention may comprise an enzyme that converts oxaloacetate to citrate (reaction 5 of FIG. 1). This enzyme may be a citrate [Si]-synthase [2.3.3.1], an ATP citrate synthase [2.3.3.8], or a citrate (Re)-synthase [2.3.3.3]. In some embodiments, the enzyme that converts oxaloacetate to citrate is an endogenous enzyme. In other embodiments, the enzyme that converts oxaloacetate to citrate is a heterologous enzyme. For example, in some embodiments, a microorganism of the invention comprises citrate synthase 1 [EC 2.3.3.16] from *B. subtilis*, such that the microorganism comprises a nucleotide sequence set forth in SEQ ID NO: 1, which encodes the amino acid sequence set forth in SEQ ID NO: 2. In some embodiments, a microorganism of the invention comprises citrate (Re)-synthase from *C. kluyveri*, such that the microorganism comprises a nucleotide sequence set forth in SEQ ID NO: 3, which encodes the amino acid sequence set forth in SEQ ID NO: 4. In some embodiments, a microorganism of the invention comprises citrate (Si)-synthase from *Clostridium* sp., such that the microorganism comprises a nucleotide sequence set forth in SEQ ID NO: 5, which encodes the amino acid sequence set forth in SEQ ID NO: 6. In some embodiments, a microorganism of the invention comprises citrate synthase 2 from *B. subtilis*, such that the microorganism comprises a nucleotide sequence set forth in SEQ ID NO: 7, which encodes the amino acid sequence set forth in SEQ ID NO: 8. In some embodiments, the enzyme that converts oxaloacetate to citrate is overexpressed.

A microorganism of the invention may comprise an enzyme that converts citrate to aconitate and aconitate to iso-citrate (reactions 6 of FIG. 1). This enzyme may be an aconitate hydratase [4.2.1.3]. In some embodiments, the enzyme that converts citrate to aconitate and aconitate to iso-citrate is an endogenous enzyme. In some embodiments, the enzyme that converts citrate to aconitate and aconitate to iso-citrate is overexpressed.

A microorganism of the invention may comprise an enzyme that converts isocitrate to glyoxylate (reaction 7 of FIG. 1). This enzyme may be an isocitrate lyase [4.1.3.1]. In some embodiments, a microorganism of the invention comprises isocitrate lyase from Z. mays, such that the microorganism comprises a nucleotide sequence set forth in SEQ ID NO: 9, which encodes the amino acid sequence set forth in SEQ ID NO: 10. In some embodiments, a microorganism of the invention comprises isocitrate lyase from E. coli, such that the microorganism comprises a nucleotide sequence set forth in SEQ ID NO: 11, which encodes the amino acid sequence set forth in SEQ ID NO: 12. In some embodiments A microorganism of the invention may comprise an enzyme that converts glyoxylate to glycolate (reaction 8 of FIG. 1). This enzyme may be a glycerate dehydrogenase [1.1.1.29], a glyoxylate reductase [1.1.1.26/79], or a glycolate dehydrogenase [1.1.99.14]. In some embodiments, the enzyme that converts glyoxylate to glycolate is an endogenous enzyme. In some embodiments, the enzyme that converts glyoxylate to glycolate is overexpressed.

A microorganism of the invention may comprise an enzyme that converts glycolate to glycoaldehyde (reaction 9 of FIG. 1). This enzyme may be a glycolaldehyde dehydrogenase [1.2.1.24], a lactaldehyde dehydrogenase [1.2.1.22], a succinate-semialdehyde dehydrogenase [1.2.1.3/4/5], a 2,5-dioxovalerate dehydrogenase [1.2.1.26], an aldehyde dehydrogenase [1.2.1.3/4/5], a betaine-aldehyde dehydrogenase [1.2.1.8], or an aldehyde ferredoxin oxidoreductase [1.2.7.5]. In some embodiments, the enzyme that converts glycolate to glycoaldehyde is an endogenous enzyme. In other embodiments, the enzyme that converts glycolate to glycoaldehyde is a heterologous enzyme. For example, in some embodiments, a microorganism of the invention comprises a gamma-aminobutyraldehyde dehydrogenase from E. coli, such that the microorganism comprises a nucleotide sequence set forth in SEQ ID NO: 49, which encodes the amino acid sequence set forth in SEQ ID NO: 50. In some embodiments, a microorganism of the invention comprises an aldehyde dehydrogenase from E. coli, such that the microorganism comprises a nucleotide sequence set forth in SEQ ID NO: 51, which encodes the amino acid sequence set forth in SEQ ID NO: 52. In some embodiments, a microorganism of the invention comprises an NADP-dependent succinate-semialdehyde dehydrogenase I from E. coli, such that the microorganism comprises a nucleotide sequence set forth in SEQ ID NO: 53, which encodes the amino acid sequence set forth in SEQ ID NO: 54. In some embodiments, a microorganism of the invention comprises a lactaldehyde dehydrogenase/glycolaldehyde dehydrogenase from G. oxydans, such that the microorganism comprises a nucleotide sequence set forth in SEQ ID NO: 55, which encodes the amino acid sequence set forth in SEQ ID NO: 56. In some embodiments, a microorganism of the invention comprises an aldehyde dehydrogenase A from P. fluorescens, such that the microorganism comprises a nucleotide sequence set forth in SEQ ID NO: 57 or SEQ ID NO: 59, which encodes the amino acid sequence set forth in SEQ ID NO: 58 or SEQ ID NO: 60, respectively. Additional non-limiting examples of enzymes that convert glycolate to glycoaldehyde can be found in GenBank Accession Nos. WP_003202098. WP_003182567, ACT39044, ACT39074, WP_041112005, and ACT40170. In some embodiments, the enzyme that converts glycolate to glycoaldehyde is overexpressed.

A microorganism of the invention may comprise an enzyme that converts glycoaldehyde to ethylene glycol (reaction 10 of FIG. 1). This enzyme may be a lactaldehyde reductase [1.1.1.77], an alcohol dehydrogenase [11.1.1.1], an alcohol dehydrogenase (NADP+) [11.1.2], a glycerol dehydrogenase [1.1.1.1.72], a glycerol-3-phosphate dehydrogenase [1.1.1.8], or an aldehyde reductase [1.1.1.21]. In some embodiments, the enzyme that converts glycoaldehyde to ethylene glycol is an endogenous enzyme. In some embodiments, the endogenous enzyme that converts glycoaldehyde to ethylene glycol is overexpressed. In other embodiments, the enzyme that converts glycoaldehyde to ethylene glycol is a heterologous enzyme. In some embodiments, a microorganism of the invention comprises a lactaldehyde reductase from C. saccharoperbutylacetonicum, such that the microorganism comprises a nucleotide sequence set forth in SEQ ID NO: 61, which encodes the amino acid sequence set forth in SEQ ID NO: 62. In some embodiments, a microorganism of the invention comprises a lactaldehyde reductase from C. ljungdahlii, such that the microorganism comprises a nucleotide sequence set forth in SEQ ID NO: 63, which encodes the amino acid sequence set forth in SEQ ID NO: 64. In some embodiments, a microorganism of the invention comprises a lactaldehyde reductase from E. coli, such that the microorganism comprises a nucleotide sequence set forth in SEQ ID NO: 65, which encodes the amino acid sequence set forth in SEQ ID NO: 66. In some embodiments, a microorganism of the invention comprises a lactaldehyde reductase from C. beijerinckii, such that the microorganism comprises a nucleotide sequence set forth in SEQ ID NO: 67, which encodes the amino acid sequence set forth in SEQ ID NO: 68. In some embodiments, the heterologous enzyme that converts glycoaldehyde to ethylene glycol is overexpressed.

A microorganism of the invention may comprise an enzyme that converts pyruvate to malate (reaction 11 of FIG. 1). This enzyme may be a malate dehydrogenase [1.1.1.37], a malate dehydrogenase (oxaloacetate-decarboxylating) [1.1.1.38], a malate dehydrogenase (decarboxylating) [1.1.1.39], a malate dehydrogenase (oxaloacetate-decarboxylating) (NADP+) [1.1.1.401, a malate dehydrogenase (NADP+) 11.1.1.82], a D-malate dehydrogenase (decarboxylating) [1.1.1.83], a dimethylmalate dehydrogenase [1.1.1.84], a 3-isopropylmalate dehydrogenase [1.1.1.85], a malate dehydrogenase [NAD(P)+] [1.1.1.299], or a malate dehydrogenase (quinone) [1.1.5.4]. In some embodiments, the enzyme that converts pyruvate to malate is an endogenous enzyme. In other embodiments, the enzyme that converts pyruvate to malate is a heterologous enzyme. For example, in some embodiments, a microorganism of the invention comprises a malate dehydrogenase from C. autoethanogenum, such that the microorganism comprises a nucleotide sequence set forth in SEQ ID NO: 23, which encodes the amino acid sequence set forth in SEQ ID NO: 24. In some embodiments, a microorganism of the invention comprises an NAD-dependent malic enzyme from C. autoethanogenum, such that the microorganism comprises a nucleotide sequence set forth in SEQ ID NO: 25, which encodes the amino acid sequence set forth in SEQ ID NO: 26.

A microorganism of the invention may comprise an enzyme that converts malate to glyoxylate (reaction 12 of FIG. 1). This enzyme may be a malate synthase [2.3.3.9] or an isocitrate lyase [4.1.3.1]. In some embodiments, the enzyme that converts malate to glyoxylate is a heterologous enzyme. For example, in some embodiments, a microorganism of the invention comprises a malate synthase G from *Sporosarcina* sp., such that the microorganism comprises a nucleotide sequence set forth in SEQ ID NO: 27 or SEQ ID NO: 33, which encodes the amino acid sequence set forth in SEQ ID NO: 28 or SEQ ID NO: 34, respectively. In some embodiments, a microorganism of the invention comprises a malate synthase G from *Bacillus* sp., such that the microorganism comprises a nucleotide sequence set forth in SEQ ID NO: 29 or SEQ ID NO: 35, which encodes the amino acid sequence set forth in SEQ ID NO: 30 or SEQ ID NO: 36, respectively. In some embodiments, a microorganism of the invention comprises a malate synthase from *S. coelicolor*, such that the microorganism comprises a nucleotide sequence set forth in SEQ ID NO: 31, which encodes the amino acid sequence set forth in SEQ ID NO: 32. In some embodiments, a microorganism of the invention comprises a malate synthase G from *B. infantis*, such that the microorganism comprises a nucleotide sequence set forth in SEQ ID NO: 37, which encodes the amino acid sequence set forth in SEQ ID NO: 38. In some embodiments, a microorganism of the invention comprises a malate synthase from *C. cochlearium*, such that the microorganism comprises a nucleotide sequence set forth in SEQ ID NO: 39, which encodes the amino acid sequence set forth in SEQ ID NO: 40. In some embodiments, a microorganism of the invention comprises a malate synthase G from *B. megaterium*, such that the microorganism comprises a nucleotide sequence set forth in SEQ ID NO: 41, which encodes the amino acid sequence set forth in SEQ ID NO: 42. In some embodiments, a microorganism of the invention comprises a malate synthase from *Paenibacillus* sp., such that the microorganism comprises a nucleotide sequence set forth in SEQ ID NO: 43, which encodes the amino acid sequence set forth in SEQ ID NO: 44. In some embodiments, a microorganism of the invention comprises a malate synthase from *Lysinibacillus* sp., such that the microorganism comprises a nucleotide sequence set forth in SEQ ID NO: 45, which encodes the amino acid sequence set forth in SEQ ID NO: 46. In some embodiments, a microorganism of the invention comprises a malate synthase from *B. cereus*, such that the microorganism comprises a nucleotide sequence set forth in SEQ ID NO: 47, which encodes the amino acid sequence set forth in SEQ ID NO: 48.

A microorganism of the invention may comprise an enzyme that converts pyruvate to phosphoenolpyruvate (reaction 13 of FIG. 1). This enzyme may be a pyruvate kinase [2.7.1.40], a pyruvate, phosphate dikinase [2.7.9.1], or a pyruvate, water dikinase [2.7.9.2]. In some embodiments, the enzyme that converts pyruvate to phosphoenolpyruvate is an endogenous enzyme.

A microorganism of the invention may comprise an enzyme that converts phosphoenolpyruvate to 2-phospho-D-glycerate (reaction 14 of FIG. 1). This enzyme may be a phosphopyruvate hydratase [4.2.1.11]. In some embodiments, the enzyme that converts phosphoenolpyruvate to 2-phospho-D-glycerate is an endogenous enzyme.

A microorganism of the invention may comprise an enzyme that converts 2-phospho-D-glycerate to 3-phospho-D-glycerate (reaction 15 of FIG. 1). This enzyme may be a phosphoglycerate mutase [5.4.2.11/12]. In some embodiments, the enzyme that converts 2-phospho-D-glycerate to 3-phospho-D-glycerate is an endogenous enzyme.

A microorganism of the invention may comprise an enzyme that converts 3-phospho-D-glycerate to 3-phosphonooxypyruvate (reaction 16 of FIG. 1). This enzyme may be a phosphoglycerate dehydrogenase [1.1.1.95]. In some embodiments, the enzyme that converts 3-phospho-D-glycerate to 3-phosphonooxypyruvate is an endogenous enzyme.

A microorganism of the invention may comprise an enzyme that converts 3-phosphonooxypyruvate to 3-phospho-L-serine (reaction 17 of FIG. 1). This enzyme may be a phosphoserine transaminase [2.6.1.52]. In some embodiments, the enzyme that converts 3-phosphonooxypyruvate to 3-phospho-L-serine is an endogenous enzyme.

A microorganism of the invention may comprise an enzyme that converts 3-phospho-L-serine to serine (reaction 18 of FIG. 1). This enzyme may be a phosphoserine phosphatase [3.1.3.3]. In some embodiments, the enzyme that converts 3-phospho-L-serine to serine is an endogenous enzyme.

A microorganism of the invention may comprise an enzyme that converts serine to glycine (reaction 19 of FIG. 1). This enzyme may be a glycine hydroxymethyltransferase [2.1.2.1]. In some embodiments, the enzyme that converts serine to glycine is an endogenous enzyme. In some embodiments, the enzyme that converts serine to glycine is overexpressed.

A microorganism of the invention may comprise an enzyme that converts glycine to glyoxylate (reaction 20 of FIG. 1). This enzyme may be an alanine-glyoxylate aminotransferase/transaminase [2.6.1.44], a serine-glyoxylate aminotransferase/transaminase [2.6.1.45], a serine-pyruvate aminotransferase/transaminase [2.6.1.51], a glycine-oxaloacetate aminotransferase/transaminase [2.6.1.35], a glycine transaminase [2.6.1.4], a glycine dehydrogenase [1.4.1.10], an alanine dehydrogenase [1.4.1.1], or a glycine dehydrogenase [1.4.2.1.]. In some embodiments, the enzyme that converts glycine to glyoxylate is an endogenous enzyme. In other embodiments, the enzyme that converts glycine to glyoxylate is a heterologous enzyme. For example, in some embodiments, a microorganism of the invention comprises serine-glyoxylate aminotransferase from *H. methylovorum*, such that the microorganism comprises a nucleotide sequence set forth in SEQ ID NO: 13, which encodes the amino acid sequence set forth in SEQ ID NO: 14. In some embodiments, a microorganism of the invention comprises alanine-glyoxvlate aminotransferase from *S. thiotaurini*, such that the microorganism comprises a nucleotide sequence set forth in SEQ ID NO: 15, which encodes the amino acid sequence set forth in SEQ ID NO: 16. In some embodiments, a microorganism of the invention comprises alanine-glyoxylate aminotransferase from *T. tepidarius*, such that the microorganism comprises a nucleotide sequence set forth in SEQ ID NO: 17, which encodes the amino acid sequence set forth in SEQ ID NO: 18. In some embodiments, a microorganism of the invention comprises a Class V aminotransferase from *C. acidurici*, such that the microorganism comprises a nucleotide sequence set forth in SEQ ID NO: 19, which encodes the amino acid sequence set forth in SEQ ID NO: 20. In some embodiments, a microorganism of the invention comprises a serine-pyruvate aminotransferase from *T. maritima*, such that the microorganism comprises a nucleotide sequence set forth in SEQ ID NO: 21, which encodes the amino acid sequence set forth in SEQ ID NO: 22. In some embodiments, the enzyme that converts glycine to glyoxylate is overexpressed.

A microorganism of the invention may comprise an enzyme that converts serine to hydroxypyruvate (reaction 21 of FIG. 1). This enzyme may be a serine-pyruvate transaminase [2.6.1.51], a serine-glyoxylate transaminase [2.6.1.45], an alanine dehydrogenase [1.4.1.1], an L-amino-acid dehydrogenase [1.4.1.5], a serine 2-dehydrogenase [1.4.1.7], an alanine transaminase [2.6.1.2], a glutamine-pyruvate transaminase [2.6.1.15], a D-amino-acid transaminase [2.6.1.21], an alanine-glyoxylate transaminase [2.6.1.44], or a serine-pyruvate transaminase [2.6.1.51]. In some embodiments, the enzyme that converts serine to hydroxypyruvate is an endogenous enzyme. In other embodiments, the enzyme that converts serine to hydroxypyruvate is a heterologous enzyme. Non-limiting examples of enzymes capable of converting serine to hydroxypyruvate can be found in GenBank Accession Nos. WP_009989311 and NP_511062.1. In some embodiments, the enzyme that converts serine to hydroxypyruvate is overexpressed.

A microorganism of the invention may comprise an enzyme that converts hydroxypyruvate to glycoaldehyde (reaction 22 of FIG. 1). This enzyme may be a hydroxypyruvate decarboxylase [4.1.1.40] or a pyruvate decarboxylase [4.1.1.1]. This enzyme may also be any other decarboxylase [4.1.1.-]. In some embodiments, the enzyme that converts hydroxypyruvate to glycoaldehyde is a heterologous enzyme. Non-limiting examples of enzymes capable of converting hydroxypyruvate to glycoaldehyde can be found in GenBank Accession Nos. CCG28866, SVF98953, PA0096, CAA54522, KRU13460, and KLA26356.

A microorganism of the invention may comprise an enzyme that converts D-glycerate to hydroxypyruvate (reaction 23 of FIG. 1). This enzyme may be a glyoxylate reductase [EC 1.1.1.26], a glycerate dehydrogenase [EC 1.1.1.29], or a hydroxypyruvate reductase [EC 1.1.1.81]. In some embodiments, the enzyme that converts D-glycerate to hydroxvpyruvate is a heterologous enzyme. Non-limiting examples of enzymes capable of converting D-glycerate to hydroxypyruvate can be found in GenBank Accession Nos. SUK16841, RPK22618, KPA02240, AGW90762, CAC 11987, Q9CA90, and Q9UBQ7.

A microorganism of the invention may comprise a complex of enzymes that converts 5,10-methylenetetrahydrofolate to glycine (reaction 24 of FIG. 1). 5,10-methylenetetrahydrofolate is a cofactor in the reductive branch of the Wood-Ljungdahl pathway and acts as a scaffold in the production of acetyl-CoA. This complex may be a glycine cleavage system comprising a glycine dehydrogenase [1.4.4.2], a dihydrolipoyl dehydrogenase [1.8.1.4], and an aminomethyltransferase (glycine synthase) [2.1.2.10]. In some embodiments, the enzymes of the complex that converts 5,10-methylenetetrahydrofolate to glycine are endogenous enzymes. In some embodiments, the enzymes of the glycine cleavage system are overexpressed.

A microorganism of the invention may comprise an enzyme that converts phosphoenolpyruvate to oxaloacetate (reaction 25 of FIG. 1). This enzyme may be a phosphoenolpyruvate carboxykinase (ATP) [4.1.1.49] or (GTP) [4.1.1.32]. In some embodiments, the enzyme that converts phosphoenolpyruvate to oxaloacetate is an endogenous enzyme. In other embodiments, the enzyme that converts phosphoenolpyruvate to oxaloacetate is a heterologous enzyme. In some embodiments, the enzyme that converts phosphoenolpyruvate to oxaloacetate is overexpressed.

In some embodiments, a microorganism comprising an enzyme that converts acetyl-CoA to pyruvate (reaction 1 of FIG. 1), an enzyme that converts pyruvate to oxaloacetate (reaction 2 of FIG. 1), an enzyme that converts oxaloacetate to citrate (reaction 5 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts oxaloacetate to citrate may be a citrate synthase from B. subtilis (SEQ ID NOs: 1-2). In a non-limiting example, the enzyme that converts iso-citrate to glyoxylate may be an isocitrate lyase from E. coli (SEQ ID NOs: 11-12). In a non-limiting example, the enzyme that converts glycolate to glycoaldehyde may be a glycolaldehyde dehydrogenase from G. oxydans (SEQ ID NOs: 55-56) or an aldehyde dehydrogenase from P. fluorescens (SEQ ID NOs: 57-58). One or more of the enzymes catalyzing reactions 2, 5, 6, 8, 9, and 10, as shown in FIG. 1, may be overexpressed. See, e.g., Example 1 and FIG. 3B.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to 2-phospho-D-glycerate (reaction 14 of FIG. 1), an enzyme that converts 2-phospho-D-glycerate to 3-phospho-D-glycerate (reaction 15 of FIG. 1), an enzyme that converts 3-phospho-D-glycerate to 3-phosphonooxypyruvate (reaction 16 of FIG. 1), an enzyme that converts 3-phosphonooxypyruvate to 3-phospho-L-serine (reaction 17 of FIG. 1), an enzyme that converts 3-phospho-L-serine to serine (reaction 18 of FIG. 1), an enzyme that converts serine to glycine (reaction 19 of FIG. 1), an enzyme that converts glycine to glyoxylate (reaction 20 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts glycine to glyoxylate may be an alanine-glyoxylate aminotransferase from S. thiotaurini (SEQ ID NOs: 15-16) or a class V aminotransferase from C. acidurici (SEQ ID NOs: 19-20). In a non-limiting example, the enzyme that converts glycolate to glycoaldehyde may be a glycolaldehyde dehydrogenase from G. oxydans (SEQ ID NOs: 55-56) or an aldehyde dehydrogenase from P. fluorescens (SEQ ID NOs: 57-58). One of more of the enzymes catalyzing the reactions of steps 19, 20, 8, 9, and 10, as shown in FIG. 1, may be overexpressed. See, e.g., Examples 2-4 and FIGS. 4B, 5B, and 6B.

In some embodiments, a microorganism comprising an enzyme that converts acetyl-CoA to pyruvate (reaction 1 of FIG. 1), an enzyme that converts pyruvate to oxaloacetate (reaction 2 of FIG. 1), an enzyme that converts oxaloacetate to citryl-CoA (reaction 3 of FIG. 1), an enzyme that converts citryl-CoA to citrate (reaction 4 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts iso-citrate to glyoxylate may be an isocitrate lyase from E. coli (SEQ ID NOs: 11-12). In a non-limiting example, the enzyme that converts iso-citrate to glyoxylate may be an isocitrate lyase from *E. coli* (SEQ ID NOs: 11-12). In a non-limiting example, the enzyme that converts glycolate to glycoaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing reactions 2, 6, 8, 9, and 10, as shown in FIG. 1, may be overexpressed.

In some embodiments, a microorganism comprising an enzyme that converts acetyl-CoA to pyruvate (reaction 1 of FIG. 1), an enzyme that converts pyruvate to malate (reaction 11 of FIG. 1), an enzyme that converts malate to glyoxylate (reaction 12 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts glycolate to glycoaldehyde may be a glycolaldehyde dehydrogenase from *G. oxydans* (SEQ ID NOs: 55-56) or an aldehyde dehydrogenase from *P. fluorescens* (SEQ ID NOs: 57-58). One of more of the enzymes catalyzing the reactions of steps 8, 9, and 10, as shown in FIG. 1, may be overexpressed.

In some embodiments, a microorganism comprising a complex of enzymes that converts 5,10-methylenetetrahydrofolate to glycine (reaction 24 of FIG. 1), an enzyme that converts glycine to glyoxylate (reaction 20 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts glycine to glyoxylate may be an alanine-glyoxylate aminotransferase from *S. thiotaurini* (SEQ ID NOs: 15-16) or a class V aminotransferase from *C. acidurici* (SEQ ID NOs: 19-20). In a non-limiting example, the enzyme that converts glycolate to glycoaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing the reactions of steps 8, 9, 10, 20, and 24 may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to oxaloacetate (reaction 25 of FIG. 1), an enzyme that converts oxaloacetate to citryl-CoA (reaction 3 of FIG. 1), an enzyme that converts citryl-CoA to citrate (reaction 4 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts iso-citrate to glyoxylate may be an isocitrate lyase from *E. coli* (SEQ ID NOs: 11-12). In a non-limiting example, the enzyme that converts glycolate to glycoaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing reactions 2, 6, 8, 9, 10, and 25, as shown in FIG. 1, may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to oxaloacetate (reaction 25 of FIG. 1), an enzyme that converts oxaloacetate to citrate (reaction 5 of FIG. 1), an enzyme that converts citrate to aconitate and aconitate to iso-citrate (reactions 6 of FIG. 1), an enzyme that converts isocitrate to glyoxylate (reaction 7 of FIG. 1), an enzyme that converts glyoxylate to glycolate (reaction 8 of FIG. 1), an enzyme that converts glycolate to glycoaldehyde (reaction 9 of FIG. 1), and an enzyme that converts glycoaldehyde to ethylene glycol (reaction 10 of FIG. 1) produces ethylene glycol. In a non-limiting example, the enzyme that converts oxaloacetate to citrate may be a citrate synthase from *B. subtilis* (SEQ ID NOs: 1-2). In a non-limiting example, the enzyme that converts iso-citrate to glyoxylate may be an isocitrate lyase from *E. coli* (SEQ ID NOs: 11-12). In a non-limiting example, the enzyme that converts glycolate to glycoaldehyde may be a glycolaldehyde dehydrogenase from *G. oxydans* (SEQ ID NOs: 55-56) or an aldehyde dehydrogenase from *P. fluorescens* (SEQ ID NOs: 57-58). One or more of the enzymes catalyzing reactions 5, 6, 8, 9, 10, and 25, as shown in FIG. 1, may be overexpressed.

In some embodiments, a microorganism comprising an enzyme that converts acetyl-CoA to pyruvate (reaction 1 of FIG. 1), an enzyme that converts pyruvate to phosphoenolpyruvate (reaction 13 of FIG. 1), an enzyme that converts phosphoenolpyruvate to 2-phospho-D-glycerate (reaction 14 of FIG. 1), an enzyme that converts 2-phospho-D-glycerate to 3-phospho-D-glycerate (reaction 15 of FIG. 1), an enzyme that converts 3-phospho-D-glycerate to 3-phosphonooxypyruvate (reaction 16 of FIG. 1), an enzyme that converts 3-phosphonooxypyruvate to 3-phospho-L-serine (reaction 17 of FIG. 1), an enzyme that converts 3-phospho-L-serine to serine (reaction 18 of FIG. 1), comprise an enzyme that converts serine to hydroxypyruvate (reaction 21 of FIG. 1), an enzyme that converts hydroxypyruvate to glycoaldehyde (reaction 22 of FIG. 1), and an enzyme that converts glycoaldehyde to ethylene glycol (reaction 10 of FIG. 1) produces ethylene glycol. The enzyme catalyzing the conversion of glycoaldehyde to ethylene glycol may be overexpressed.

In some embodiments, a microorganism comprising an enzyme that converts D-glycerate to hydroxypyruvate (reaction 23 of FIG. 1), an enzyme that converts hydroxypyruvate to glycoaldehyde (reaction 22 of FIG. 1), and an enzyme that converts glycoaldehyde to ethylene glycol (reaction 10 of FIG. 1) produces ethylene glycol. The enzyme catalyzing the conversion of glycoaldehyde to ethylene glycol may be overexpressed.

The enzymes of the invention may be codon optimized for expression in the microorganism of the invention. "Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in the microorganism of the invention. Although codon optimization refers to the underlying genetic sequence, codon optimization often results in improved translation and, thus, improved enzyme expression. Accordingly, the enzymes of the invention may also be described as being codon optimized.

One or more of the enzymes of the invention may be overexpressed. "Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate. As described above, one or more of the enzymes catalyzing reactions 2, 5, 6, 8, 9, 10, 19, 20, 24, or 25 of FIG. 1 may be overexpressed.

The enzymes of the invention may comprise a disruptive mutation. A "disruptive mutation" refers to a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

In some embodiments, the microorganism of the invention comprises a disruptive mutation in isocitrate dehydrogenase [1.1.1.41]. Isocitrate dehydrogenase converts isocitrate to 2-oxoglutarate. Disruption of isocitrate dehydrogenase, such as by deleting isocitrate dehydrogenase, results in increased levels of iso-citrate.

In some embodiments, the microorganism of the invention comprises a disruptive mutation in glycerate dehydrogenase [1.1.1.29]. Glycerate dehydrogenase converts glyoxylate to glycolate. Disruption of glycerate dehydrogenase, such as by deleting isocitrate dehydrogenase, results in increased levels of glyoxylate.

In some embodiments, the microorganism of the invention comprises a disruptive mutation in glycolate dehydrogenase [1.1.99.14]. Glycolate dehydrogenase converts glyoxylate to glycolate. Disruption of glycolate dehydrogenase, such as by deleting glycolate dehydrogenase, results in increased levels of glyoxylate.

In some embodiments, the microorganism of the invention comprises a disruptive mutation in aldehyde ferredoxin oxidoreductase [1.2.7.5]. Aldehyde ferredoxin oxidoreductase converts glycolate to glycoaldehyde. Disruption of aldehyde ferredoxin oxidoreductase, such as by deleting aldehyde ferredoxin oxidoreductase, results in increased levels of glycolate.

In some embodiments, the microorganism of the invention comprises a disruptive mutation in aldehyde dehydrogenase [1.2.1.3/1.2.3.4/1.2.3.5]. Aldehyde dehydrogenase converts glycolate to glycoaldehyde. Disruption of aldehyde dehydrogenase, such as by deleting aldehyde dehydrogenase, results in increased levels of glycolate.

Introduction of a disruptive mutation results in a microorganism of the invention that produces no target product or substantially no target product or a reduced amount of target product compared to the parental microorganism from which the microorganism of the invention is derived. For example, the microorganism of the invention may produce no target product or at least about 1%, 3%, 5%, 10%, 20%, 30%, 40%, 50%, 60%, 70%, 80%, 90%, or 95% less target product than the parental microorganism. For example, the microorganism of the invention may produce less than about 0.001, 0.01, 0.10, 0.30, 0.50, or 1.0 g/L target product.

Although exemplary sequences and sources for enzymes are provided herein, the invention is by no means limited to these sequences and sources—it also encompasses variants. The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate ferredoxin oxidoreductase promoter, an Rnf complex operon promoter, an ATP synthase operon promoter, or a phosphotransacetylase/acetate kinase operon promoter.

"Substrate" refers to a carbon and/or energy source for the microorganism of the invention. Often, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons. In other embodiments, however, the substrate may be a carbohydrate, such as sugar, starch, fiber, lignin, cellulose, or hemicellulose or a combination thereof. For example, the carbohydrate may be fructose, galactose, glucose, lactose, maltose, sucrose, xylose, or some combination thereof. In some embodiments, the substrate does not comprise (D)-xylose (Alkim, *Microb Cell Fact*, 14: 127, 2015). In some embodiments, the substrate does not comprise a pentose such as xylose (Pereira, *Metab Eng*, 34: 80-87, 2016). In some embodiments, the substrate may comprise both gaseous and carbohydrate substrates (mixotrophic fermentation).

The gaseous substrate generally comprises at least some amount of CO, such as about 1, 2, 5, 10, 20, 30, 40, 50, 60, 70, 80, 90, or 100 mol % CO. The gaseous substrate may comprise a range of CO, such as about 20-80, 30-70, or 40-60 mol % CO. Preferably, the gaseous substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the gaseous substrate may comprise a relatively low amount of CO, such as about 1-10 or 1-20 mol % CO. The microorganism of the invention typically converts at least a portion of the CO in the gaseous substrate to a product. In some embodiments, the gaseous substrate comprises no or substantially no (<1 mol %) CO.

The gaseous substrate may comprise some amount of $H_2$. For example, the gaseous substrate may comprise about 1, 2, 5, 10, 15, 20, or 30 mol % $H_2$. In some embodiments, the gaseous substrate may comprise a relatively high amount of $H_2$, such as about 60, 70, 80, or 90 mol % $H_2$. In further embodiments, the gaseous substrate comprises no or substantially no (<1 mol %) $H_2$.

The gaseous substrate may comprise some amount of $CO_2$. For example, the gaseous substrate may comprise about 1-80 or 1-30 mol % $CO_2$. In some embodiments, the gaseous substrate may comprise less than about 20, 15, 10, or 5 mol % $CO_2$. In another embodiment, the gaseous substrate comprises no or substantially no (<1 mol %) $CO_2$.

The gaseous substrate may also be provided in alternative forms. For example, the gaseous substrate may be dissolved in a liquid or adsorbed onto a solid support.

The gaseous substrate and/or C1-carbon source may be a waste gas or an off gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the gaseous substrate and/or C1-carbon source may be captured from the industrial process before it is emitted into the atmosphere, using any convenient method.

The gaseous substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the gaseous substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, fiber, lignin, cellulose, or hemicellulose.

In some embodiments, the overall energetics of CO and $H_2$ to ethylene glycol (MEG) are preferable to those from glucose to ethylene glycol, as shown below, wherein the more negative Gibbs free energy, $\Delta_r G'm$, values for CO and $H_2$ indicate a larger driving force towards ethylene glycol. Calculations of overall reaction delta G for the comparison of glucose vs CO as a substrate were performed using equilibrator (http://equilibrator.weizmann.ac.il/), which is a standard method for evaluating the overall feasibility of a pathway or individual steps in pathways in biological systems (Flamholz, E. Noor, A. Bar-Even, R. Milo (2012) eQuilibrator—the biochemical thermodynamics calculator Nucleic Acids Res 40:D770-5; Noor, A. Bar-Even, A. Flamholz, Y. Lubling, D. Davidi, R. Milo (2012) An integrated open framework for thermodynamics of reactions that combines accuracy and coverageBioinformatics 28:2037-2044; Noor. H. S. Haraldsdóttir, R. Milo, R. M. T. Fleming (2013) Consistent Estimation of Gibbs Energy Using Component Contributions PLoS Comput Biol 9(7): e1003098; Noor, A. Bar-Even, A. Flamholz, E. Reznik, W. Liebermeister, R. Milo (2014) Pathway Thermodynamics Highlights Kinetic Obstacles in Central Metabolism PLoS Comput Biol 10(2): e1003483). The calculations are as follows:

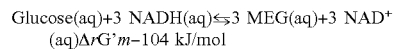
Glucose(aq)+3 NADH(aq)⇌3 MEG(aq)+3 NAD$^+$(aq)$\Delta_r$G'm−104 kJ/mol

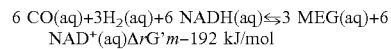
6 CO(aq)+3$H_2$(aq)+6 NADH(aq)⇌3 MEG(aq)+6 NAD$^+$(aq)$\Delta_r$G'm−192 kJ/mol Physiological Conditions:

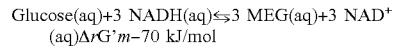
Glucose(aq)+3 NADH(aq)⇌3 MEG(aq)+3 NAD$^+$(aq)$\Delta_r$G'm−70 kJ/mol

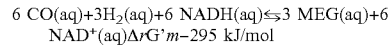
6 CO(aq)+3$H_2$(aq)+6 NADH(aq)⇌3 MEG(aq)+6 NAD$^+$(aq)$\Delta_r$G'm−295 kJ/mol In addition to ethylene glycol, glyoxylate, and/or glycolate, the microorganism of the invention may be cultured to produce one or more co-products products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In some embodiments, in addition to ethylene glycol, the microorganism of the invention also produces ethanol, 2,3-butanediol, and/or succinate. In certain embodiments, microbial biomass itself may be considered a product.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived. Ethylene glycol is not known to be produced by any naturally-occurring microorganism, such that it is a non-native product of all microorganisms.

"Selectivity" refers to the ratio of the production of a target product to the production of all fermentation products produced by a microorganism. The microorganism of the invention may be engineered to produce products at a certain selectivity or at a minimum selectivity. In one embodiment, a target product, such as ethylene glycol, accounts for at least about 5%, 10%, 15%, 20%, 30%, 50%, or 75% of all fermentation products produced by the microorganism of the invention. In one embodiment, ethylene glycol accounts for at least 10% of all fermentation products produced by the microorganism of the invention, such that the microorganism of the invention has a selectivity for ethylene glycol of at least 10%. In another embodiment, ethylene glycol accounts for at least 30% of all fermentation products produced by the microorganism of the invention, such that the microorganism of the invention has a selectivity for ethylene glycol of at least 30%.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of ethylene glycol. If necessary, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic microorganisms. In certain embodiments, the microorganism of the invention is a non-photosynthetic microorganism.

The method of the invention may further comprise separating the ethylene glycol from the fermentation broth. Ethylene glycol may be separated or purified from a fermentation broth using any method or combination of methods known in the art, including, for example, distillation, simulated moving bed processes, membrane treatment, evaporation, pervaporation, gas stripping, phase separation, ion exchange, or extractive fermentation, including for example, liquid-liquid extraction. In one embodiment, ethylene glycol may be concentrated from the fermentation broth using reverse osmosis and/or pervaporation (U.S. Pat. No. 5,552,023). Water may be removed by distillation and the bottoms (containing a high proportion of ethylene glycol) may then be recovered using distillation or vacuum distillation to produce a high purity ethylene glycol stream. Alternatively, with or without concentration by reverse osmosis and/or pervaporation, ethylene glycol may be further purified by reactive distillation with an aldehyde (Atul, *Chem Eng Sci.* 59: 2881-2890, 2004) or azeotropic distillation using a hydrocarbon (U.S. Pat. No. 2,218,234). In another approach, ethylene glycol may be trapped on an activated carbon or polymer absorbent from aqueous solution (with or without reverse osmosis and/or pervaporation) and recovered using a low boiling organic solvent (Chinn, Recovery of Glycols, Sugars, and Related Multiple —OH Compounds from Dilute-Aqueous Solution by Regenerable Adsorption onto Activated Carbons, University of California Berkeley, 1999). Ethylene glycol can then be recovered from the organic solvent by distillation. In certain embodiments, ethylene glycol is recovered from the fermentation broth by continuously removing a portion of the broth from the bioreactor, separating microbial cells from the broth (conveniently by filtration), and recovering ethylene glycol from the broth. Co-products, such as alcohols or acids may also be separated or purified from the broth. Alcohols may be recovered, for example, by distillation. Acids may be recovered, for example, by adsorption on activated charcoal. Separated microbial cells may be returned to the bioreactor in certain embodiments. The cell-free permeate remaining after target products have been removed is also preferably returned to the bioreactor, in whole or in part. Additional nutrients (such as B vitamins) may be added to the cell-free permeate to replenish the medium before it is returned to the bioreactor.

Recovery of diols from aqueous media has been demonstrated a number of ways. Simulated moving bed (SMB) technology has been used to recover 2,3-butanediol from an aqueous mixture of ethanol and associated oxygenates (U.S. Pat. No. 8,658,845). Reactive separation has also been demonstrated for effective diol recovery. In some embodiments, recovery of ethylene glycol is conducted by reaction of the diol-containing stream with aldehydes, fractionation and regeneration of the diol, final fractionation to recover a concentrated diol stream. See, e.g., U.S. Pat. No. 7,951,980.

The invention provides compositions comprising ethylene glycol produced by the microorganisms and according to the methods described herein. For example, the composition comprising ethylene glycol may be an antifreeze, preservative, dehydrating agent, or drilling fluid.

The invention also provides polymers comprising ethylene glycol produced by the microorganisms and according to the methods described herein. Such polymers may be, for example, homopolymers such as polyethylene glycol or copolymers such as polyethylene terephthalate. Methods for the synthesis of these polymers are well-known in the art. See, e.g., Herzberger et al., Chem Rev., 116(4): 2170-2243 (2016) and Xiao et al., Ind Eng Chem Res. 54(22): 5862-5869 (2015).

The invention further provides compositions comprising polymers comprising ethylene glycol produced by the microorganisms and according to the methods described herein. For example, the composition may be a fiber, resin, film, or plastic.

EXAMPLES

The following examples further illustrate the invention but, of course, should not be construed to limit its scope in any way.

Figure 2A:
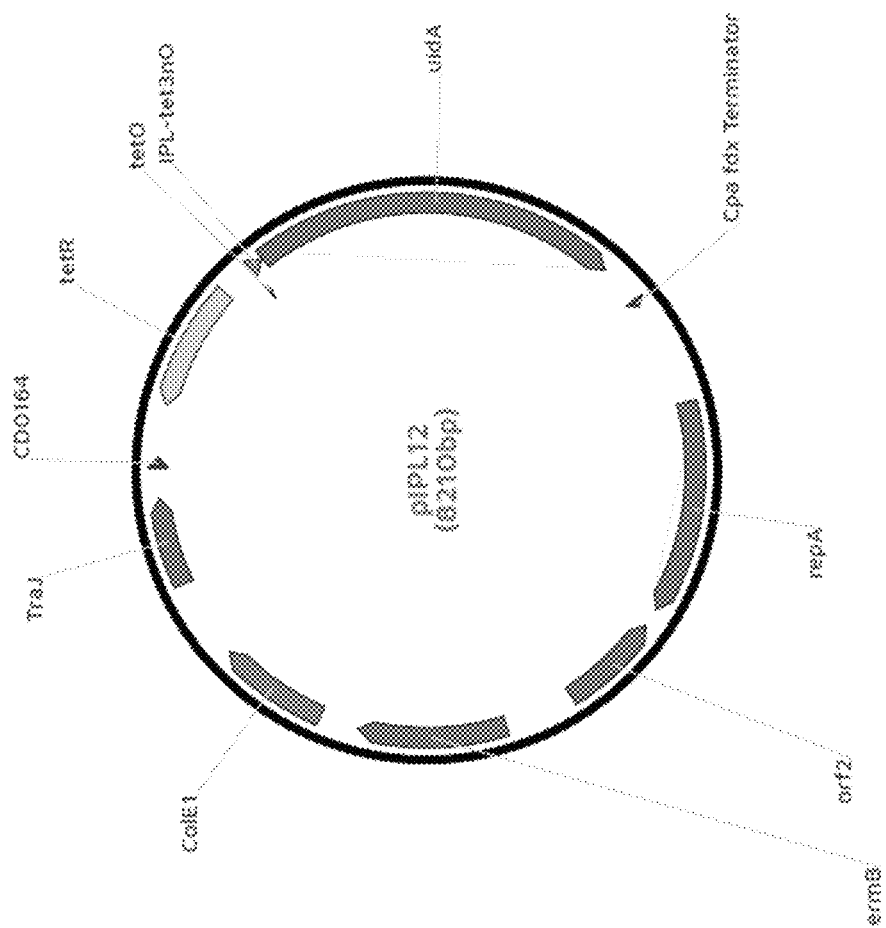
FIGS. 2A-2E are maps of plasmids used in Examples 1-4.
Figure 2B:
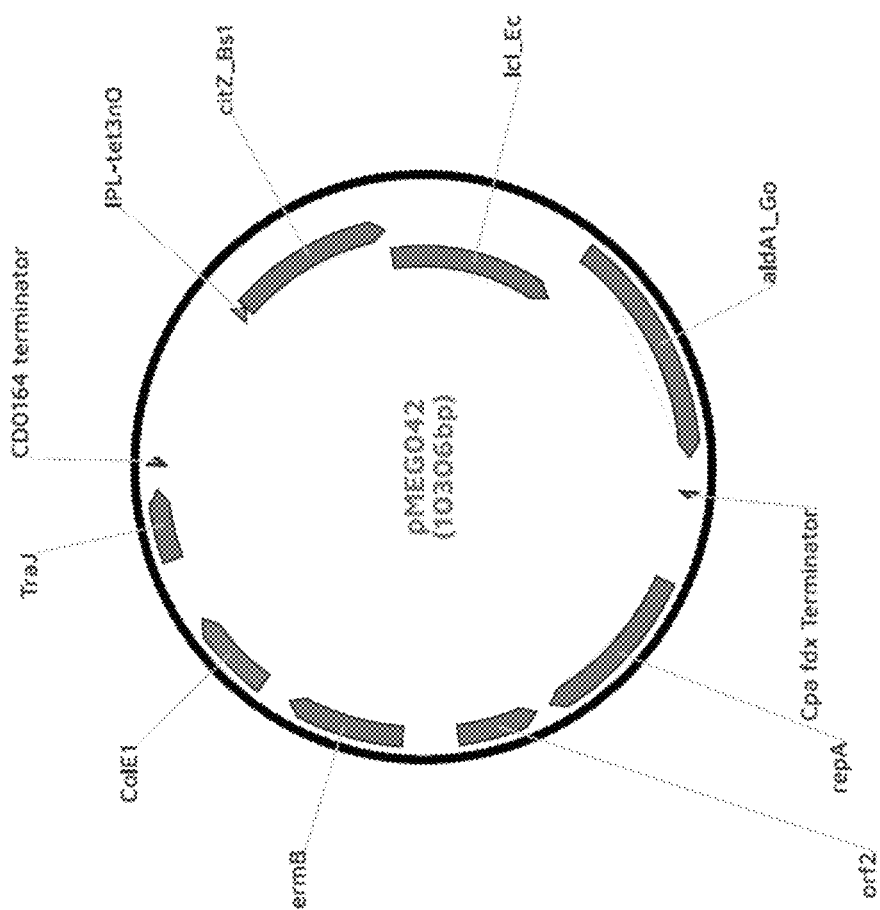

Example 1: Construction of Heterologous Expression Vector Comprising B. subtilis Citrate Synthase, E. coli Isocitrate Lyase, and G. oxydans Glycolaldehyde Dehydrogenase for Production of Ethylene Glycol from CO and/or $CO_2$ and $H_2$ in C. autoethanogenum Genes coding for citrate synthase from B. subtilis (citZ; SEQ ID NOs: 1-2), isocitrate lyase from E. coli (icl; SEQ ID NOs: 11-12), and glycolaldehyde dehydrogenase from G. oxydans (aldA1; SEQ ID NOs: 55-56) were codon-adapted and synthesized for expression in C. autoethanogenum. The adapted genes were cloned into an expression shuttle vector, pIPL12, using a standard BsaI golden gate cloning kit (New England Biolabs, Ipswich, Mass.), pIPL12 comprises an origin of replication for both E. coli and C. autoethanogenum, enabling it to replicate and be maintained in both species; pIPL12 also functions in most Clostridia, pIPL12 further comprises 23S rRNA (adenine(2058)-N(6))-methyltransferase Erm(B) conferring erythromycin/clarithromycin resistance for positive selection, TraJ for conjugative transfer from E. coli, and a promoter for expression of heterologous genes. See FIG. 2A. The expression vector created upon cloning of citZ, icl, and aldA1 into pIPL12 is referred to as pMEG042 herein (FIG. 2B).

TABLE 2

Oligos used to construct pMEG042 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 71 | citZ_BsI-F | CACACCAGGTCTCACATATGACAGCAACAAGGGGCC |
| 72 | citZ_BsI-R | CACACCAGGTCTCAATTGTAACACCTCCTTAATTAGTTATGCTCTTTCTTTTATAGGTACAAATTTTTG |
| 73 | Icl_Ec-F | CACACCAGGTCTCACAATGAAAACAAGAACTCAACAAATAG |
| 74 | Icl_Ec-R | CACACCAGGTCTCAGTGTTCCTCCTATGTGTTCTTAAAATTGAGATTCTTCAGTTGAACCTG |
| 75 | aldA1_Go-F | CACACCAGGTCTCAACACATATGACTGAAAAAAATAATTTATTCATAAATGGATC |
| 76 | aldA1_Go-R | CACACCAGGTCTCAGGTTATGCATTTAGATATATTGTTTTTGTCTGTACG |

The pMEG042 construct was transformed into C. autoethanogenum via conjugation. The expression vector was first introduced into the conjugative donor strain, E. coli HB101+R702 (CA434) (Williams et al. 1990) (the donor), using standard heat shock transformation. Donor cells were recovered in SOC media at 37° C. for 1 h before being plated onto LB media plates comprising 100 µg/mL spectinomycin and 500 µg/mL erythromycin and incubated at 37° C. overnight. The next day, 5 mL LB aliquots comprising 100 µg/mL spectinomycin and 500 µg/mL erythromycin were inoculated with several donor colonies and incubated at 37° C., shaking for approximately 4 h or until the culture was visibly dense but had not yet entered stationary phase. 1.5 mL of the donor culture was harvested by centrifugation at 4000 rpm and 20-25° C. for 2 min, and the supernatant was discarded. The donor cells were gently resuspended in 500 µL sterile PBS buffer and centrifuged at 4000 rpm for 2 min, and the PBS supernatant was discarded.

The pellet was introduced into an anaerobic chamber and gently resuspended in 200 µL during late exponential phase of a C. autoethanogenum culture (the recipient). C. autoethanogenum DSM10061 and DSM23693 (a derivate of DSM10061) were sourced from DSMZ (The German Collection of Microorganisms and Cell Cultures, Inhoffenstraße 7 B, 38124 Braunschweig, Germany). Strains were grown at 37° C. in PETC medium (See U.S. Pat. No. 9,738,875) at pH 5.6 using standard anaerobic techniques (Hungate 1969; Wolfe 1971).

The conjugation mixture (the mix of donor and recipient cells) was spotted onto PETC-MES+fructose agar plates and left to dry. When the spots were no longer visibly wet, the plates were introduced into a pressure jar, pressurized with syngas (50% CO, 10%0 $N_2$, 30% $CO_2$, 10% $H_2$) to 25-30 psi, and incubated at 37° C. for ~24 h. The conjugation mixture was then removed from the plates by gentle scraping using a 10 µL inoculation loop. The removed mixture was suspended in 200-300 µL PETC media. 100 µL aliquots of the conjugation mixture were plated onto PETC media agar plates supplemented 5 µg/mL clarithromycin to select for transformants bearing the plasmid.

Figure 3A:
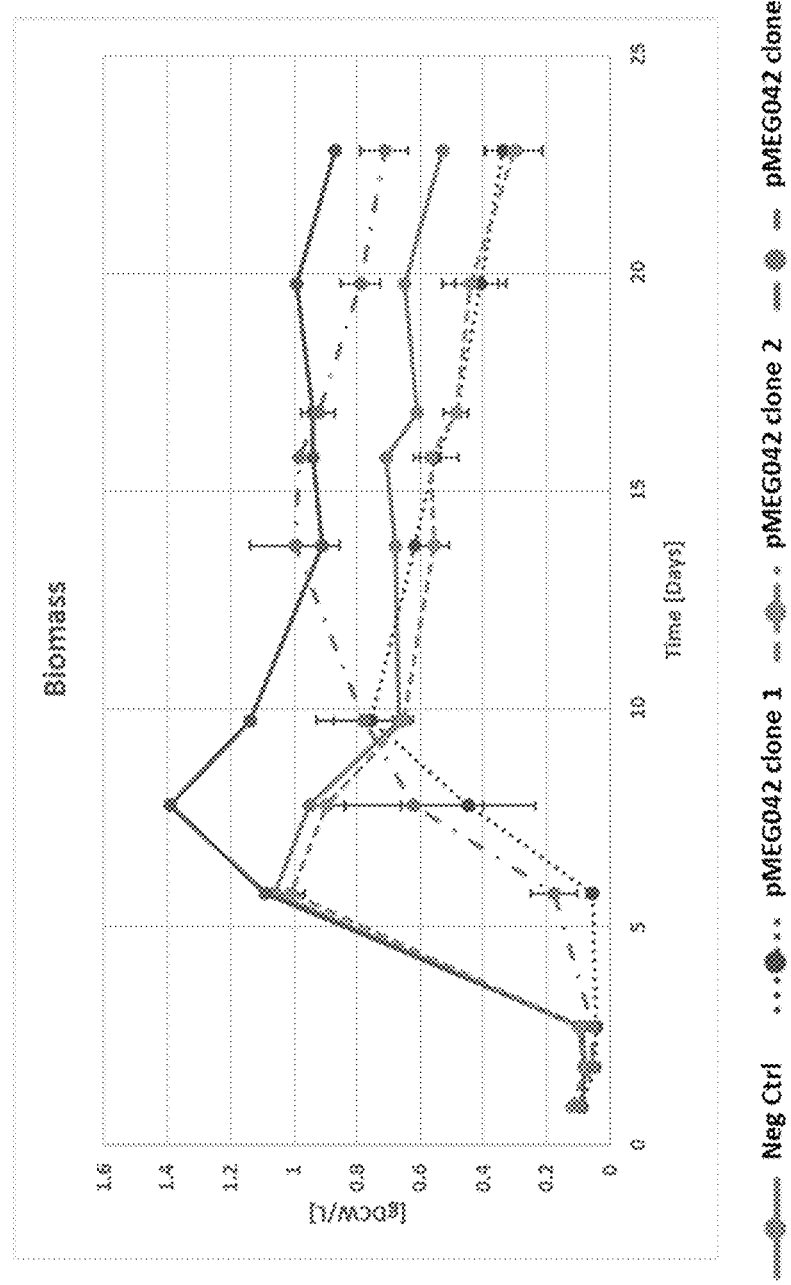
FIG. 3A shows biomass levels (g dry cell weight/L) of *C. autoethanogenum* expressing pMEG042 (clones 1-3) or *C. autoethanogenum* comprising an empty vector (negative control).
Figure 3B:
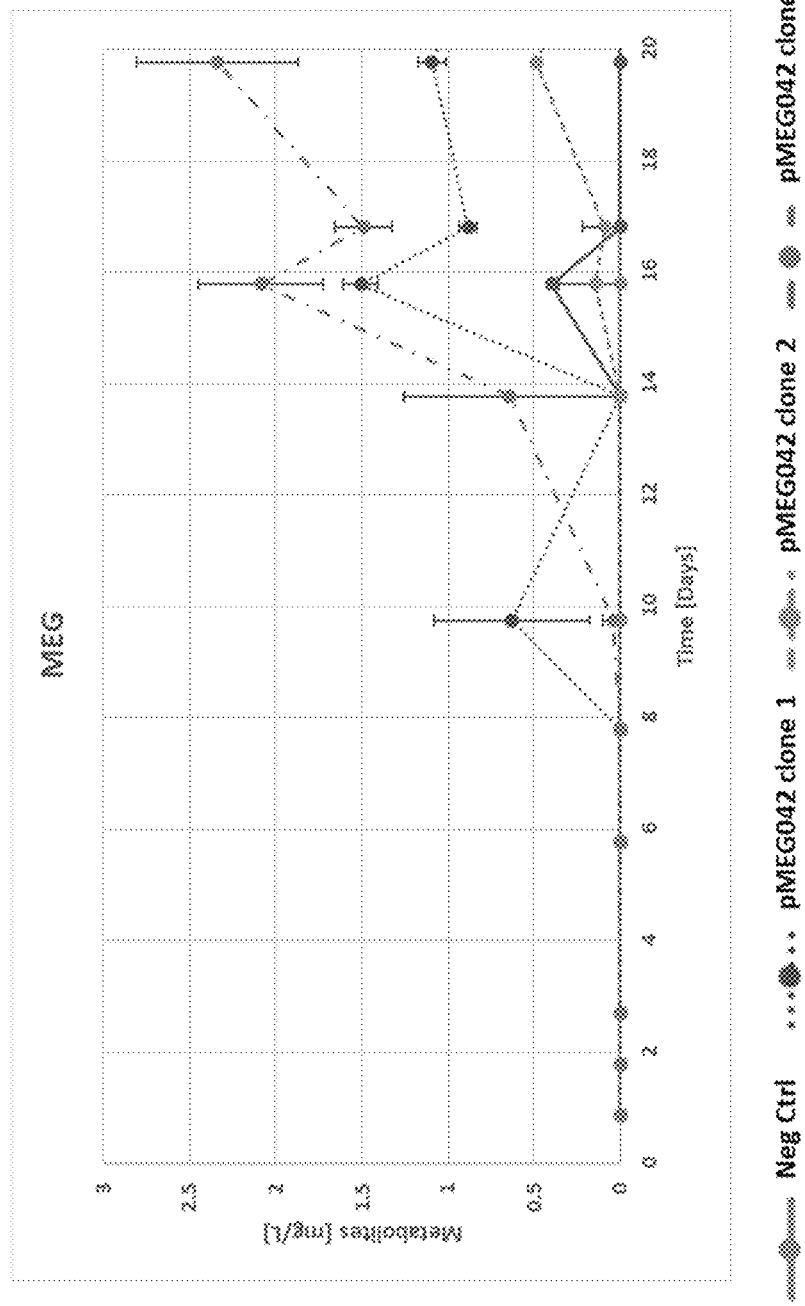
FIG. 3B shows ethylene glycol produced over time in *C. autoethanogenum* growing autotrophically and carrying expression vector pMEG042, as compared to the negative control (empty vector).
Figure 3C:
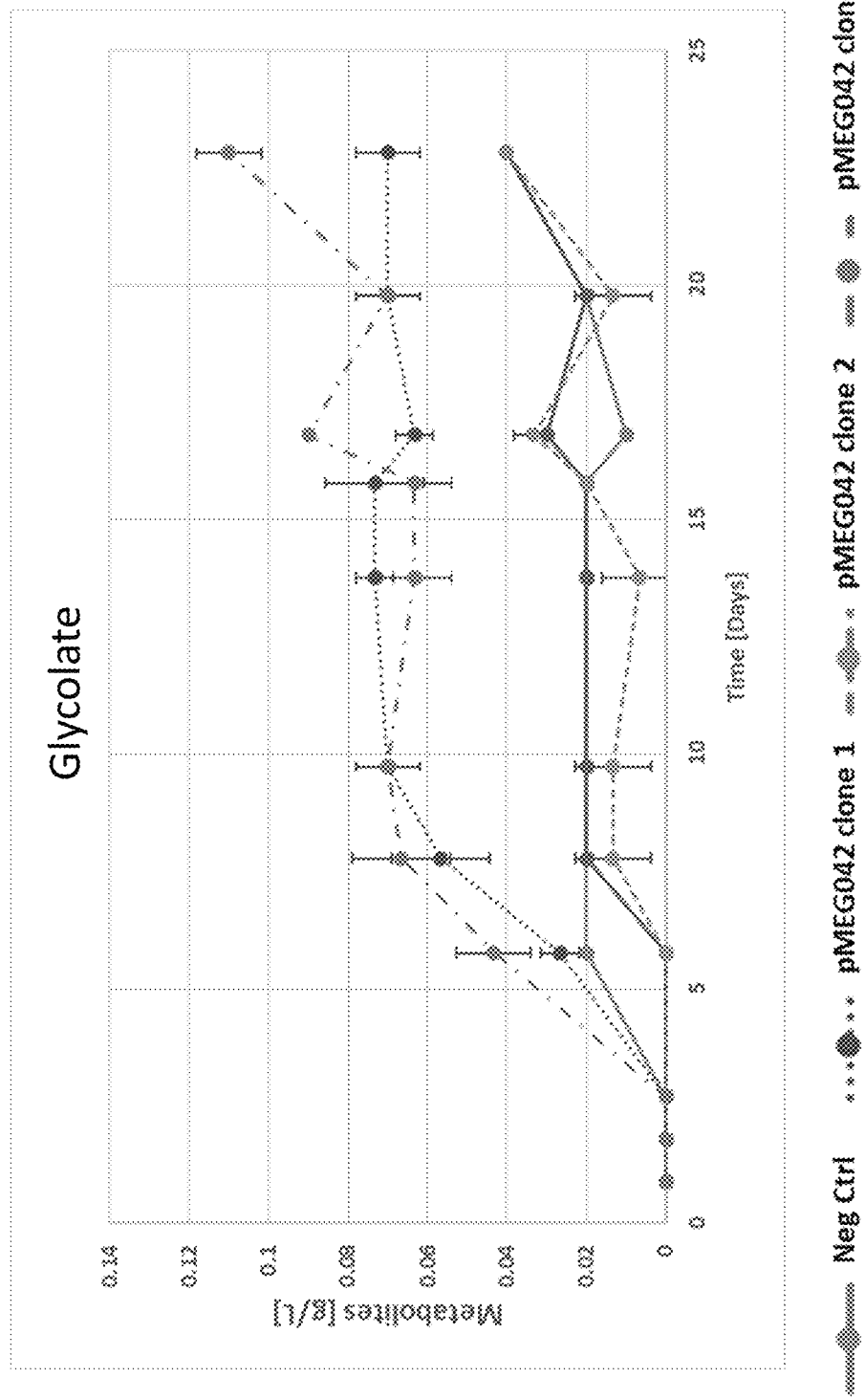
FIG. 3C shows glycolate produced over time in *C. autoethanogenum* growing autotrophically and carrying expression vector pMEG042. See Example 1.

Three distinct colonies of *C. autoethanogenum* bearing the pMEG042 plasmid were inoculated into 2 mL of PETC-MES media with 5 µg/mL clarithromycin and grown autotrophically at 37° C. with 50% CO, 10% $N_2$, 30% $CO_2$, 10% $H_2$ and 100 rpm orbital shaking with for three days. Cultures were diluted to $OD_{600}$ of 0.05 in 10 mL PETC-MES medium with 5 µg/mL clarithromycin in serum bottles and grown autotrophically at 37° C. with 50% CO, 10% $N_2$, 30% $CO_2$, 10% $H_2$ and 100 rpm orbital shaking for up to 20 days, sampling daily to measure biomass and metabolites (FIGS. 3A and 3B). Production of ethylene glycol was measured using gas chromatography mass spectrometry (GC-MS), and other metabolites were measured using high-performance liquid chromatography (HPLC), as described below.

Ethylene glycol concentrations were measured with a Thermo Scientific ISQ LT GCMS equipped an Agilent VF-WAXms column (15 m×0.25 µm×0.25 µm) and RSH autosampler. Samples were prepared by diluting 200 µL of broth with 200 µL of methanol. The samples were vortexed then centrifuged for 3 min at 14,000 rpm; 200 µL of the supernatant was transferred to a glass vial with insert. Samples were transferred to an autosampler for analysis using a 1.0 µL injection, a split ratio of 5 to 1, and an inlet temperature of 240° C. Chromatography was performed with an oven program of 80° C. with a 0.5 min hold to a ramp of 10° C./min to 150° C. to a ramp of 25° C./min to 220° C. with a 3 min final hold. The column flow rate was 4.0 mL/min with a 0.5 min hold then dropping to 1.5 ml/min at a rate of 100 ml/min/min using helium as the carrier gas. The MS ion source was kept at 260° C. with the transfer line set at 240° C. Quantitation was performed using a linear external standard calibration using 33.0 m/z as the quantitation peak and 31.0+62.0 m/z as the confirming peaks.

Ethanol, acetate, 2,3-butanediol, glyoxylate, and glycolate concentrations were measured by HPLC on an Agilent 1260 Infinity LC with Refractive Index (RI) detection at 35° C. Samples were prepared by heating for 5 min at 80*C, followed by a 3 min centrifugation at 14,000 rpm; the supernatant was transferred to a glass vial for analysis. Separation was carried out with a 10 µL injection on to a Phenomenex Rezex™ ROA-Organic Acid H+(8%) column (300 mm×7.8 mm×8 µm) at 0.7 mL/min and 35° C. under isocratic conditions, using 5 mM sulphuric acid mobile phase.

After approximately 3 days of autotrophic growth, the ethylene glycol precursor glycolate was observed, and after 10 days, production of ethylene glycol was observed (FIG. 3B).

Example 2: Construction of Heterologous Expression Vector Comprising *S. thiotaurini* Alanine-Glyoxylate Aminotransferase and *P. fluorescens* Aldehyde Dehydrogenase for Production of Ethylene Glycol from CO and/or CO and $H_2$ in *C. autoethanogenum*

Figure 2C:
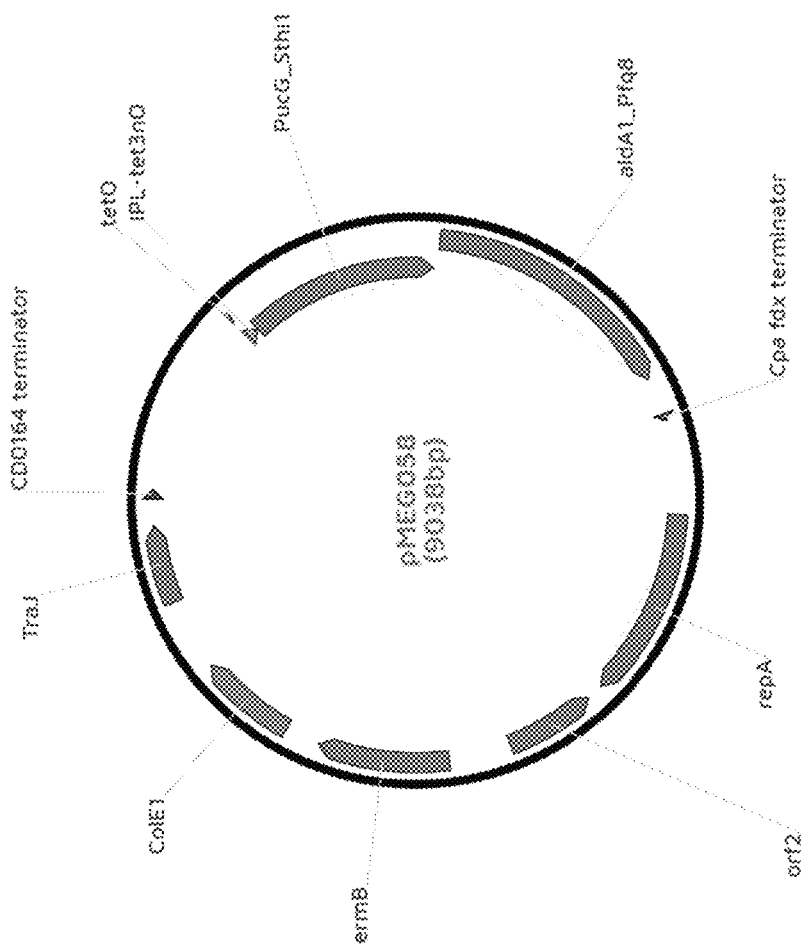

Genes coding for an alanine-glyoxylate aminotransferase from *S. thiotaurini* (pucG; SEQ ID NOs: 15-16) and aldehyde dehydrogenase from *P. fluorescens* Q8r1-96 (aldA1; SEQ ID NOs: 57-58) were codon-adapted and synthesized for expression in *C. autoethanogenum*. The codon-adapted genes were cloned into pIPL12 (FIG. 2A), and the resulting expression vector, pMEG058, was introduced into *C. autoethanogenum*, as described in Example 1. See FIG. 2C.

TABLE 3

Oligos used to construct pMEG058 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 77 | PucG_Sthi1-F | CACACCAGGTCTCACATATGCAATTTAGGCCTTTTAATCCACCA |
| 78 | PucG_Sthi1-R | CACACCAGGTCTCAGTGTTCCTCCTATGTGTTCTTATGCTTGCGCAAGTGCCT |
| 79 | aldA1_Pfq8-F | CACACCAGGTCTCAACACATATGTCTTCAGTGCCTGTATTCCAG |
| 80 | aldA1_Pfq8-R | CACACCAGGTCTCAGGTTAAGACTGGAGATATACTGCATGAG |

Figure 4A:
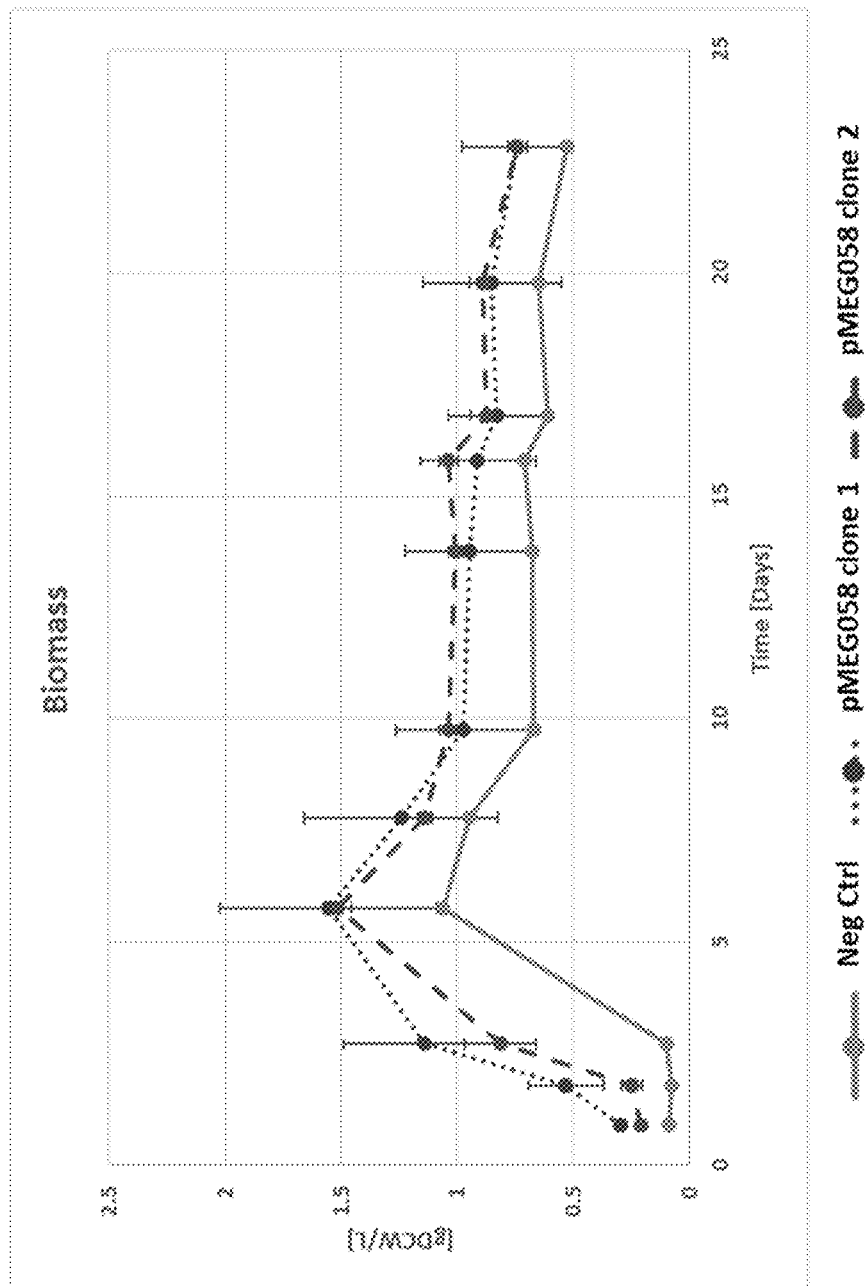
FIG. 4A shows biomass levels (g dry cell weight/L) of *C. autoethanogenum* expressing pMEG058 (clones 1-2) or *C. autoethanogenum* comprising an empty vector (negative control).
Figure 4B:
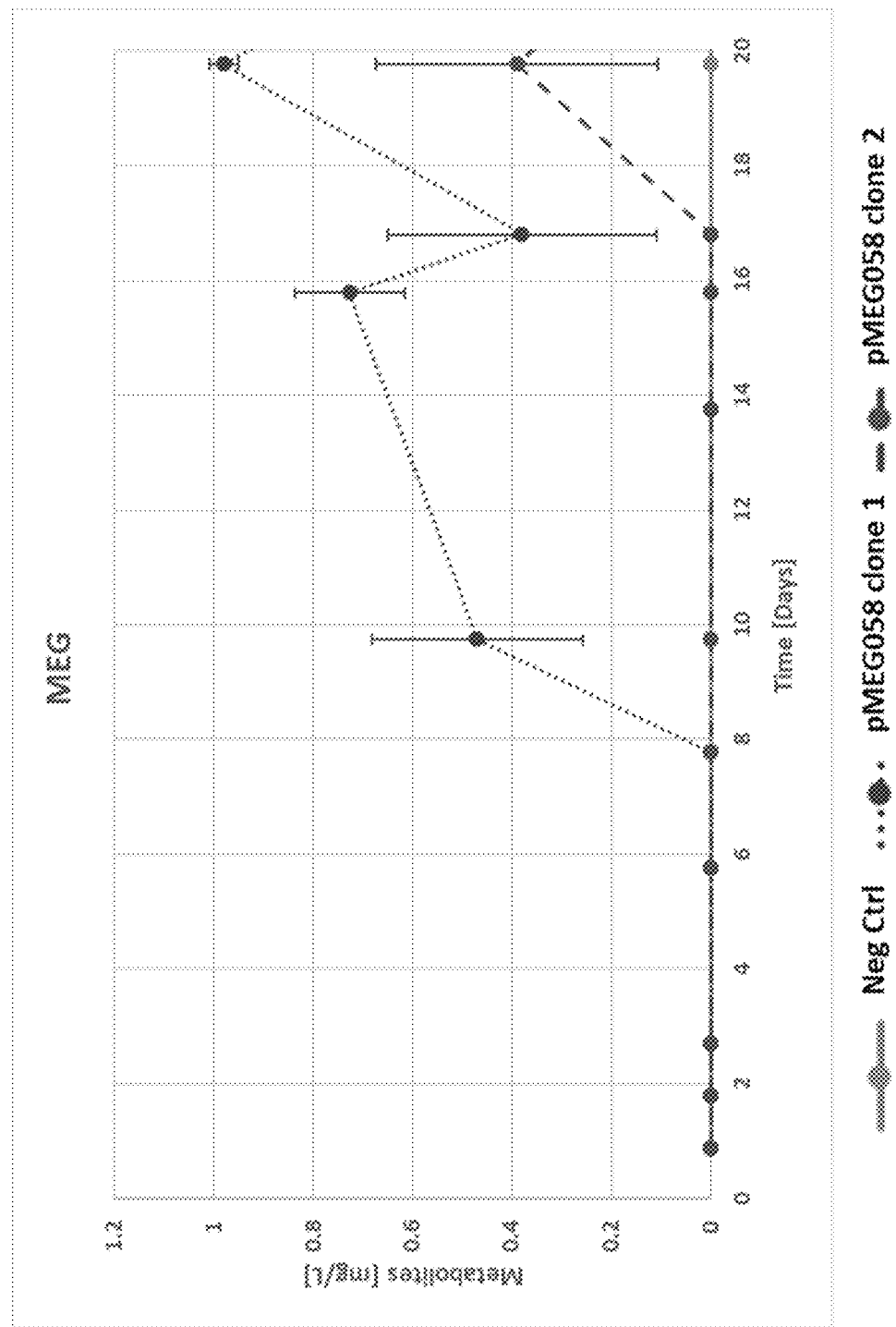
FIG. 4B shows ethylene glycol produced over time in *C. autoethanogenum* growing autotrophically and carrying expression vector pMEG058, as compared to the negative control (empty vector). See Example 2.

Two distinct colonies of *C. autoethanogenum* bearing the pMEG058 plasmid were inoculated into 2 mL of PETC-MES media with 5 µg/mL clarithromycin and grown autotrophically, as described in Example 1. See FIG. 4A. After approximately 3 days of autotrophic growth, glycolate was observed, and after 8 days production of ethylene glycol was observed (FIG. 4B).

Example 3: Construction of Heterologous Expression Vector Comprising *S. thiotaurini* Alanine-Glyoxylate Aminotransferase and *G. oxydans* Glycolaldehyde Dehydrogenase for Production of Ethylene Glycol from CO and/or $CO_2$ and $H_2$ in *C. autoethanogenum*

Figure 2D:
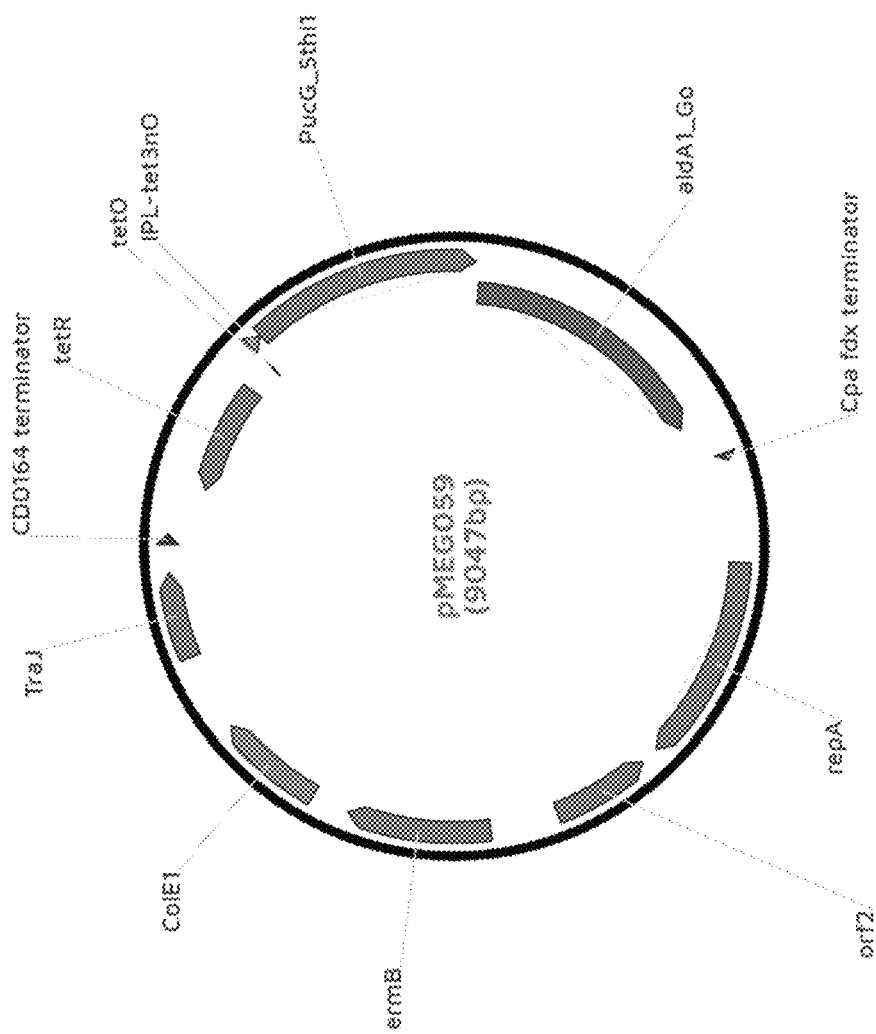

Genes coding for an alanine-glyoxylate aminotransferase from *S. thiotaurini* (pucG: SEQ ID NOs: 15-16) and glycolaldehyde dehydrogenase from *G. oxydans* (aldA1; SEQ ID NOs: 55-56) were codon-adapted and synthesized for expression in *C. autoethanogenum*. The codon-adapted genes were cloned into pIPL12 (FIG. 2A), and the resulting expression vector, pMEG059, was introduced into *C. autoethanogenum*, as described in Example 1. See FIG. 2D.

TABLE 4

Oligos used to construct pMEG059 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 77 | PucG_Sthi1-F | CACACCAGGTCTCACATATGCAATTTAGGCCTTTTAATCCACCA |
| 78 | PucG_Sthi1-R | CACACCAGGTCTCAGTGTTCCTCCTATGTGTTCTTATGCTTGCGCAAGTGCCT |
| 75 | aldA1_Go-F | CACACCAGGTCTCAACACATATGACTGAAAAAAATAATTTATTCATAAATGGATC |
| 76 | aldA1_Go-R | CACACCAGGTCTCAGGTTATGCATTTAGATATATTGTTTTTGTCTGTACG |

Figure 5A:
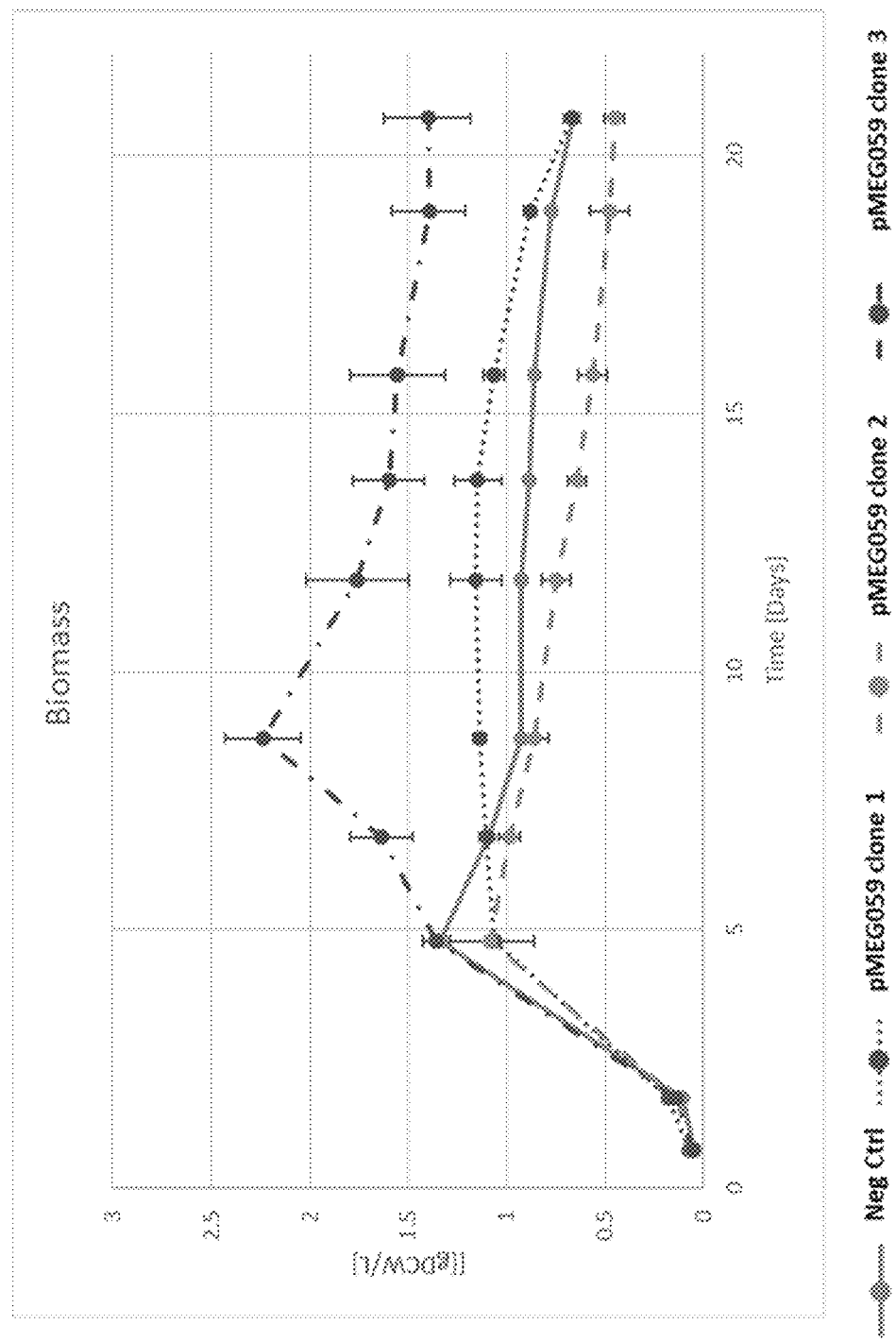
FIG. 5A shows biomass levels (g dry cell weight/L) of *C. autoethanogenum* expressing pMEG059 (clones 1-3) or *C. autoethanogenum* comprising an empty vector (negative control).
Figure 5B:
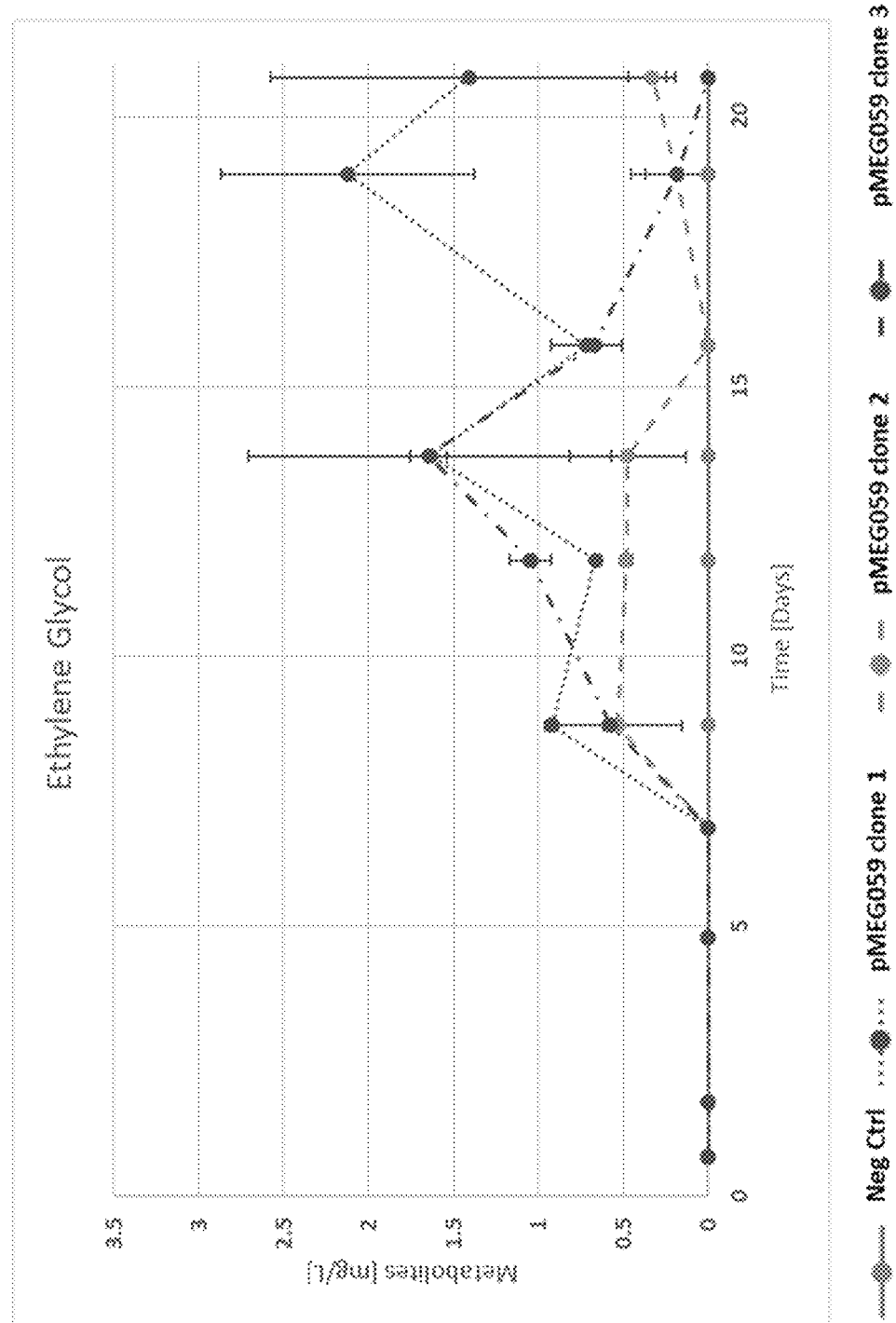
FIG. 5B shows ethylene glycol produced over time in *C. autoethanogenum* growing autotrophically and carrying expression vector pMEG059, as compared to the negative control (empty vector). See Example 3.

Two distinct colonies of *C. autoethanogenum* bearing the pMEG059 plasmid were inoculated into 2 mL of PETC-MES medium with 5 µg/mL clarithromycin and grown autotrophically, as described in Example 1. See FIG. 5A. After approximately 3 days of autotrophic growth, glycolate was observed, and after 10 days, production of ethylene glycol was observed (FIG. 5B).

Example 4: Construction of Heterologous Expression Vector Comprising Alanine-Glyoxylate Aminotransferase and Aldehyde Dehydrogenase for Production of Ethylene Glycol from CO and/or $CO_2$ and $H_2$ in *C. autoethanogenum*

Figure 2E:
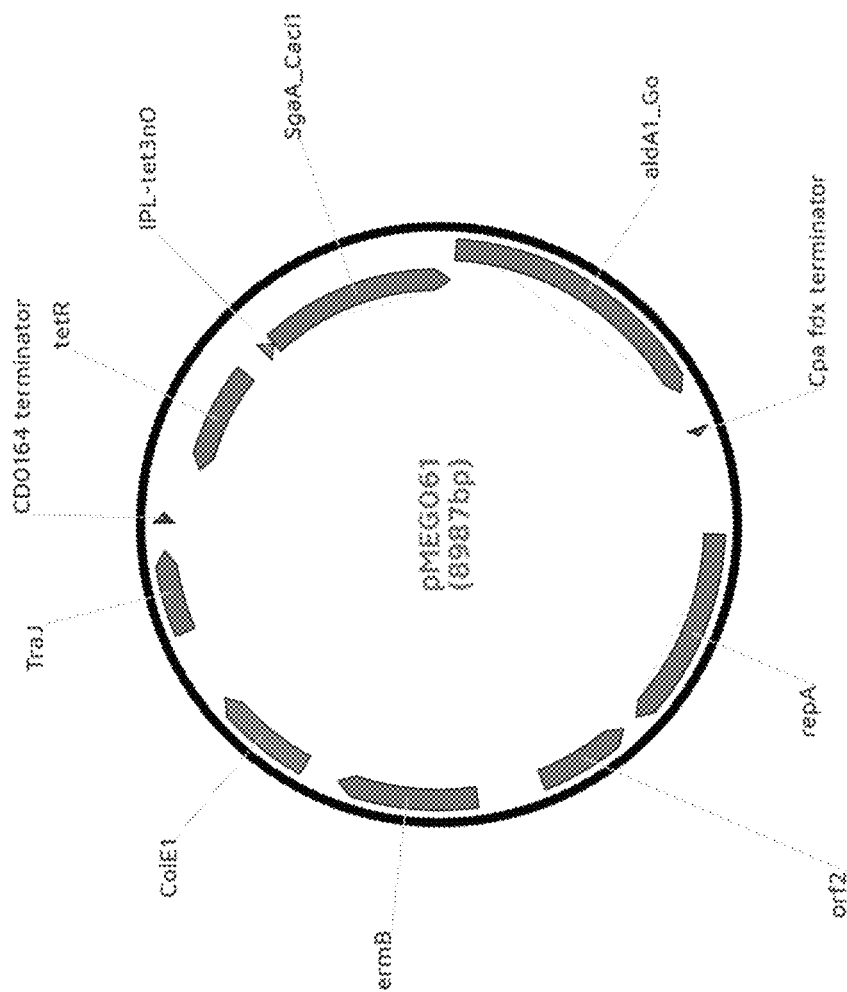

Genes coding for class V aminotransferase from C(*acidurici* (SgA; SEQ ID NOs: 19, 20) and aldehyde dehydrogenase from *P. fluorescens* Q8r1-96 (aldA1; SEQ ID NOs: 57-58) were codon-adapted and synthesized for expression in *C. autoethanogenum*. The codon-adapted genes were cloned into pIPL12 (FIG. 2A), and the resulting vector, pMEG061, was introduced into *C. autoethanogenum*, as described in Example 1. See FIG. 2E.

Figure 6A:
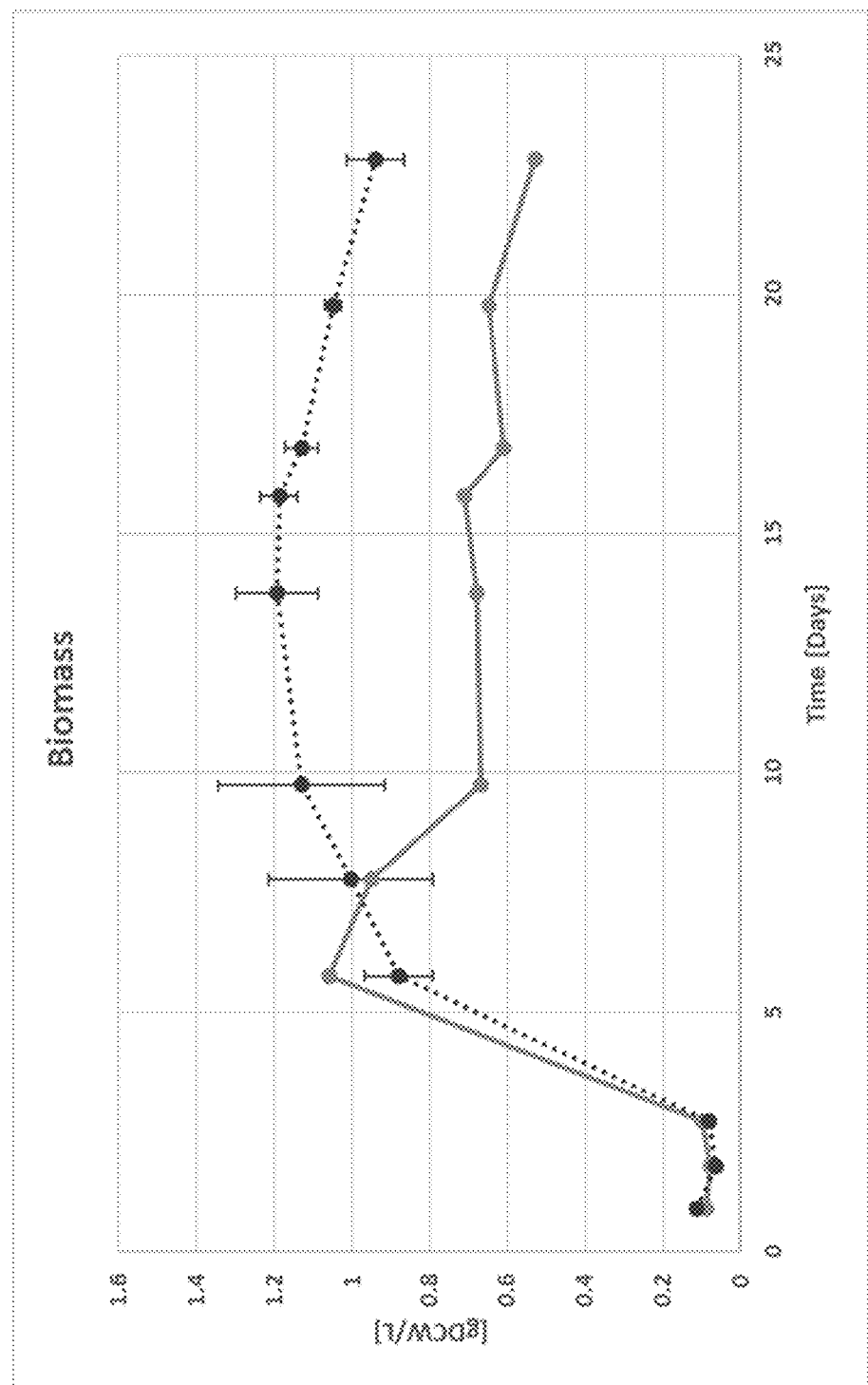
FIG. 6A shows biomass levels (g dry cell weight L) of *C. autoethanogenum* expressing pMEG061 (clones 1) or *C. autoethanogenum* comprising an empty vector (negative control).
Figure 6B:
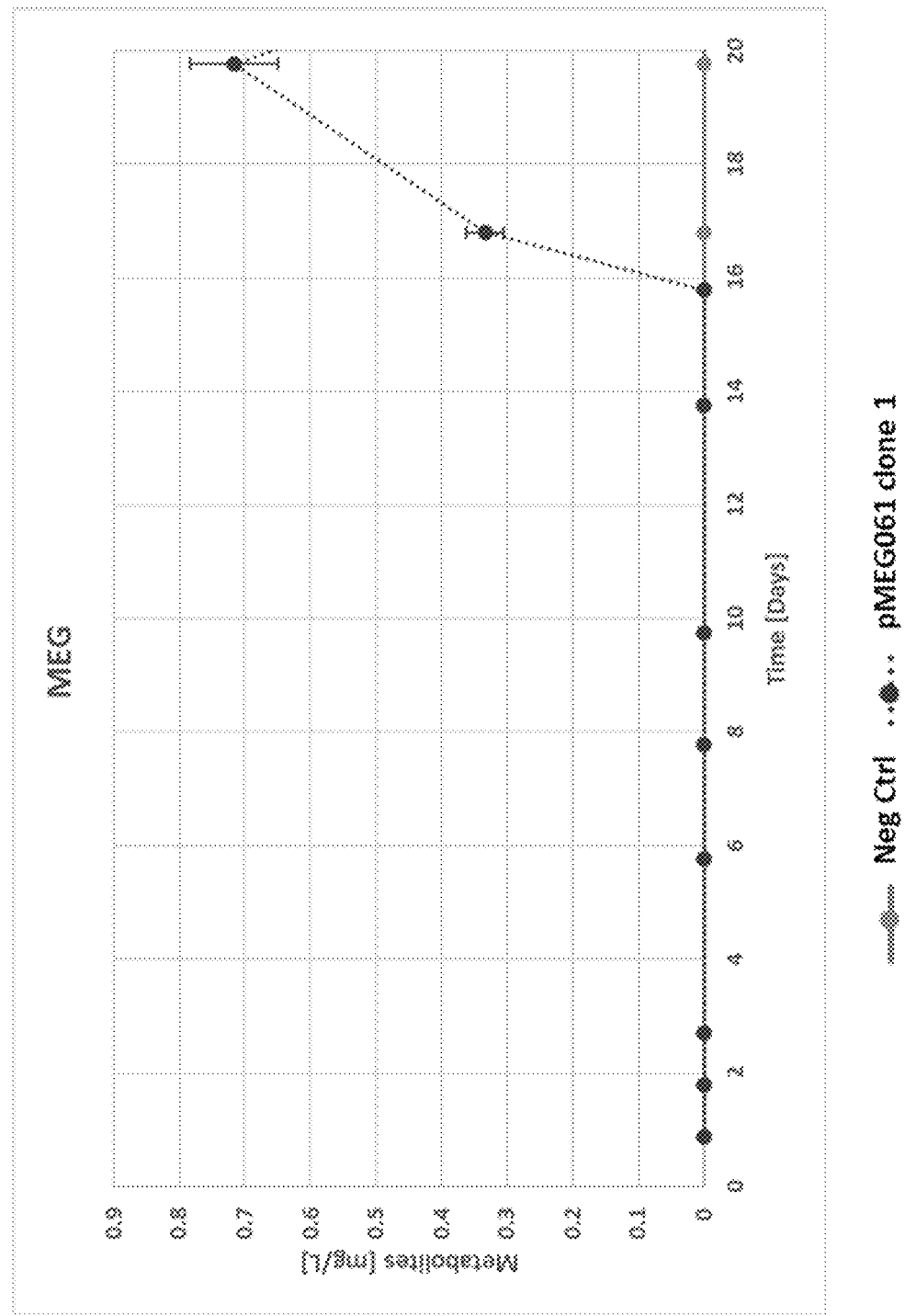
FIG. 6B shows ethylene glycol produced over time in *C. autoethanogenum* growing autotrophically and carrying expression vector pMEG061, as compared to the negative control (empty vector). See Example 4.

MES medium with 5 µg/mL clarithromycin and grown autotrophically, as described in Example 1. See FIG. 6A. After approximately 3 days of autotrophic growth, glycolate was observed, and after 16 days, production of ethylene glycol was observed (FIG. 6B).

Example 5: Modeling of Maximum Yields of Different Routes to Ethylene Glycol

A genome-scale metabolic model of *Clostridium autoethanogenum* like the one described by Marcellin, *Green Chem*, 18: 3020-3028, 2016 was utilized to predict maximum yields of different routes to ethylene glycol. Heterologous metabolic reactions were added to the wild type *Clostridium autoethanogenum* model structure to represent the incorporation of the non-native compound production pathway. Although the model used for the experimental work described herein is based on *Clostridium autoethanogenum*, the results can reasonably be expected to apply to other Wood-Ljungdahl microorganisms as well, given similarities in metabolism.

Ethylene glycol production was simulated using constraint-based computational modeling techniques flux bal-

TABLE 5

Oligos used to construct pMEG061 expression vector.

| SEQ ID NO | Name | Sequence |
|---|---|---|
| 69 | pIPL12-bb-F | CACACCAGGTCTCAAACCATGGAGATCTCGAGGCCTG |
| 70 | pIPL12-bb-R | CACACCAGGTCTCACATATGATAAGAAGACTCTTGGC |
| 81 | SgaA_Caci1-F | CACACCAGGTCTCACATATGAGAACTCCATTTATTATGAC |
| 82 | SgaA_Caci1-R | CACACCAGGTCTCAGTGTTCCTCCTATGTGTTCCTAATCTACAAAGTGCTTG |
| 79 | aldA1_Pfq8-F | CACACCAGGTCTCAACACATATGTCTTCAGTGCCTGTATTCCAG |
| 80 | aldA1_Pfq8-R | CACACCAGGTCTCAGGTTAAGACTGGAGATATACTGCATGAG |

Three distinct colonies of *C. autoethanogenum* bearing the pMEG061 plasmid were inoculated into 2 mL of PETCance analysis (FBA) and linear minimization of metabolic adjustment (LMOMA) (Maia, *Proceedings of the Genetic* and *Evolutionary Computation Conference Companion on—GECCO '17*, New York, N.Y., ACM Press, 1661-1668, 2017) using cobrapy version 0.8.2 (Ebrahim., COBRApy: COnstraints-Based Reconstruction and Analysis for Python, *BMC Syst Biol.* 7: 74, 2013), with optlang version 1.2.3 (Jensen, Optlang: An Algebraic Modeling Language for Mathematical Optimization," The Journal of Open Source Software, 2, doi: 10.21105/joss.00139, 2017) as the solver interface and Gurobi Optimizer version 7.0.2 as the optimization solver.

Modeling revealed a predicted yield of 0.37 mol ethylene glycol/mol CO by the pathways described herein in Examples 1-4. This is more than double the predicted yield by the hypothetical pathways described by Islam et al. *Metab Eng*, 41: 173-181, 2017, which require gluconeogenesis; the highest predicted yields were found to be ~0.44 g ethylene glycol/g CO, which equals ~0.18 mol ethylene glycol/mol CO.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A genetically engineered carboxydotrophic acetogenic microorganism capable of producing ethylene glycol or a precursor of ethylene glycol from a gaseous substrate, wherein the microorganism comprises a nucleic acid encoding a heterologous enzyme capable of converting glycolate to glycolaldehyde and one or more of:
   i) a nucleic acid encoding a heterologous enzyme capable of converting oxaloacetate to citrate;
   ii) a nucleic acid encoding a heterologous enzyme capable of converting glycine to glyoxylate; and
   iii) a nucleic acid encoding a heterologous enzyme capable of converting iso-citrate to glyoxylate, wherein:
   a) the heterologous enzyme capable of converting oxaloacetate to citrate is a citrate [Si]-synthase having the EC number 2.3.3.1, an ATP citrate synthase having the EC number 2.3.3.8; or a citrate (Re)-synthase having the EC number 2.3.3.3;
   b) the heterologous enzyme capable of converting glycine to glyoxylate is an alanine-glyoxylate transaminase having the EC number 2.6.1.44, a serine-glyoxylate transaminase having the EC number 2.6.1.45, a serine-pyruvate transaminase having the EC number 2.6.1.51, a glycine-oxaloacetate transaminase having the EC number 2.6.1.35, a glycine transaminase having the EC number 2.6.1.4, an alanine dehydrogenase having the EC number 1.4.1.1, or a glycine dehydrogenase having the EC number 1.4.2.1; and/or
   c) the heterologous enzyme capable of converting iso-citrate to glyoxylate is an isocitrate lyase having the EC number 4.1.3.1, and wherein the heterologous enzyme capable of converting glycolate to glycolaldehyde is a glycolaldehyde dehydrogenase having the EC number 1.2.1.21, a lactaldehyde dehydrogenase having the EC number 1.2.1.22, a succinate-semialdehyde dehydrogenase having the EC number 1.2.1.24, a 2,5-dioxovalerate dehydrogenase having the EC number 1.2.1.26, a betaine-aldehyde dehydrogenase having the EC number 1.2.1.8, or an aldehyde ferredoxin oxidoreductase having the EC number 1.2.7.5.

2. The microorganism of claim 1, wherein the microorganism produces ethylene glycol or the precursor of ethylene glycol through one or more intermediates selected from the group consisting of 5,10-methylenetetrahydrofolate, oxaloacetate, citrate, malate, and glycine.

3. The microorganism of claim 1, wherein one or more of the heterologous enzymes are derived from a genus selected from the group consisting of Bacillus, Clostridium, Escherichia, Gluconobacter, Hyphomicrobium, Lysinibacillus, Paenibacillus, Pseudomonas, Sedimenticola, Sporosarcina, Streptomyces, Thermithiobacillus, Thermotoga, and Zea.

4. The microorganism of claim 3, wherein one or more of the heterologous enzymes are codon-optimized for expression in the microorganism.

5. The microorganism of claim 1, wherein the microorganism further comprises one or more of a nucleic acid encoding: an enzyme capable of converting acetyl-CoA to pyruvate having the EC number 1.2.7.1; an enzyme capable of converting pyruvate to oxaloacetate having the EC number 6.4.1.1; an enzyme capable of converting pyruvate to malate having the EC number 1.1.1.37, 1.1.1.38, 1.1.1.39, 1.1.1.40, 1.1.1.82, 1.1.1.83, 1.1.1.84, 1.1.1.85, 1.1.1.299, or 1.1.5.4; an enzyme capable of converting pyruvate to phosphoenolpyruvate having the EC number 2.7.1.40 or 2.7.9.2; an enzyme capable of converting oxaloacetate to citryl-CoA having the EC number 4.1.3.34; an enzyme capable of converting citryl-CoA to citrate having the EC number 2.8.3.10; an enzyme capable of converting citrate to aconitate and aconitate to iso-citrate having the EC number 4.2.1.3; an enzyme capable of converting phosphoenolpyruvate to oxaloacetate having the EC number 4.1.1.49 or 4.1.1.32; an enzyme capable of converting phosphoenolpyruvate to 2-phospho-D-glycerate having the EC number 4.2.1.11; an enzyme capable of converting 2-phospho-D-glycerate to 3-phospho-D-glycerate having the EC number 5.4.2.11/12; an enzyme capable of converting 3-phospho-D-glycerate to 3-phosphonooxypyruvate having the EC number 1.1.1.95; an enzyme capable of converting 3-phosphonooxypyruvate to 3-phospho-L-serine having the EC number 2.6.1.52; an enzyme capable of converting 3-phospho-L-serine to serine having the EC number 3.1.3.3; an enzyme capable of converting serine to glycine having the EC number 2.1.2.1; an enzyme capable of converting 5,10-methylenetetrahydrofolate to glycine having the EC number 1.4.4.2, 1.81.4, or 2.1.2.10; an enzyme capable of converting serine to hydroxypyruvate having the EC number 2.6.1.51, 2.6.1.45, 1.4.1.1, 1.4.1.5, 1.4.1.7, 2.6.1.2, 2.6.1.15. 2.6.1.21, or 2.6.1.44; an enzyme capable of converting D-glycerate to hydroxypyruvate having the EC number 1.1.1.29 or 1.1.1.81; an enzyme capable of converting malate to glyoxylate having the EC number 2.3.3.9 or 4.1.3.1; an enzyme capable of converting glyoxylate to glycolate having the EC number 1.1.1.29, 1.1.1.26/79, or 1.1.99.14; an enzyme capable of converting hydroxypyruvate to glycolaldehyde having the EC number 4.1.1.40 or 4.1.1.1; and an enzyme capable of converting glycolaldehyde to ethylene glycol having the EC number 1.1.1.77, 1.1.1.1, 1.1.1.2, 1.1.1.72, 1.1.1.8, or 1.1.1.21.

6. The microorganism of claim 3, wherein the microorganism overexpresses:
   i) the heterologous enzyme capable of converting oxaloacetate to citrate;
   ii) the heterologous enzyme capable of converting glycine to glyoxylate; and/or
   iii) the heterologous enzyme capable of converting glycolate to glycoaldehyde.

7. The microorganism of claim 5, wherein the microorganism overexpresses:
   i) the enzyme capable of converting pyruvate to oxaloacetate having the EC number 6.4.1.1;
   ii) the enzyme capable of converting citrate to aconitate and aconitate to iso-citrate having the EC number 4.2.1.3;
   iii) the enzyme capable of converting phosphoenolpyruvate to oxaloacetate having the EC number 4.1.1.49 or 4.1.1.32;
   iv) the enzyme capable of converting serine to glycine having the EC number 2.1.2.1;
   v) the enzyme capable of converting 5,10-methylenetetrahydrofolate to glycine having the EC number 1.4.4.2, 1.81.4, or 2.1.2.10;
   vi) the enzyme capable of converting glyoxylate to glycolate having the EC number 2.3.3.9; and/or
   vii) the enzyme capable of converting glycolaldehyde to ethylene glycol having the EC number 1.1.1.77, 1.1.1.1, 1.1.1.2, 1.1.1.72, 1.1.1.8, or 1.1.1.21.

8. The microorganism of claim 1, wherein the microorganism comprises a disruptive mutation in one or more of isocitrate dehydrogenase, glycerate dehydrogenase, glycolate dehydrogenase, glycerate dehydrogenase, glycolate dehydrogenase, aldehyde ferredoxin oxidoreductase, and aldehyde dehydrogenase.

9. The microorganism of claim 1, wherein the microorganism is a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*.

10. The microorganism of claim 1, wherein the microorganism is derived from a parental microorganism selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlit, Clostridium magnum, Clostridium ragsdalei, Clostridium scatologenes, Eubacterium limosum, Moorella thermautotrophica, Moorella thermoacetica, Oxobacter pfennigii, Sporomua ovata, Sporomuaa silvacetica, Sporomusa sphaeroides*, and *Thermoanaerobacter kiuvi*.

11. The microorganism of claim 10, wherein the microorganism is derived from a parental bacterium selected from the group consisting of *Clostridium autoethanogenum, Clostridium ljungdahlii*, and *Clostridium ragsdalei*.

12. The microorganism of claim 1, wherein the microorganism comprises a native or heterologous Wood-Ljungdahl pathway.

13. The microorganism of claim 1, wherein the precursor of ethylene glycol is glyoxylate or glycolate.

14. A method of producing ethylene glycol or a precursor of ethylene glycol comprising culturing the microorganism of claim 1 in a nutrient medium in the presence of a gaseous substrate, whereby the microorganism produces ethylene glycol or the precursor of ethylene glycol.

15. The method of claim 14, wherein the gaseous substrate comprises one or more of CO, $CO_2$, and $H_2$.

16. The method of claim 14, wherein the precursor of ethylene glycol is glyoxylate or glycolate.

17. The method of claim 14, further comprising separating ethylene glycol or the precursor of ethylene glycol from the nutrient medium.

18. The method of claim 14, wherein the microorganism further produces one or more of ethanol, 2,3-butanediol, and succinate.

* * * * *